United States Patent
Vince et al.

(10) Patent No.: US 9,394,338 B2
(45) Date of Patent: Jul. 19, 2016

(54) GLUTATHIONE ANALOGS AND USES THEREOF

(75) Inventors: Robert Vince, St. Paul, MN (US); Swati Sudhakar More, St. Paul, MN (US)

(73) Assignee: REGENTS OF THE UNIVERSITY OF MINNESOTA, Minneapolis, MN (US)

(*) Notice: Subject to any disclaimer, the term of this patent is extended or adjusted under 35 U.S.C. 154(b) by 0 days.

(21) Appl. No.: 14/131,655

(22) PCT Filed: Jul. 6, 2012

(86) PCT No.: PCT/US2012/045835
§ 371 (c)(1),
(2), (4) Date: Jan. 8, 2014

(87) PCT Pub. No.: WO2013/009647
PCT Pub. Date: Jan. 17, 2013

(65) Prior Publication Data
US 2014/0154192 A1 Jun. 5, 2014

Related U.S. Application Data

(60) Provisional application No. 61/505,898, filed on Jul. 8, 2011.

(51) Int. Cl.
| | | |
|---|---|---|
| A61K 38/00 | (2006.01) | |
| C07K 5/02 | (2006.01) | |
| A61K 8/64 | (2006.01) | |
| A61Q 17/04 | (2006.01) | |
| A61Q 19/08 | (2006.01) | |
| C07K 7/02 | (2006.01) | |

(52) U.S. Cl.
CPC ... *C07K 5/02* (2013.01); *A61K 8/64* (2013.01); *A61Q 17/04* (2013.01); *A61Q 19/08* (2013.01); *C07K 5/0215* (2013.01); *C07K 7/02* (2013.01); *A61K 38/00* (2013.01)

(58) Field of Classification Search
None
See application file for complete search history.

(56) References Cited

U.S. PATENT DOCUMENTS

| | | |
|---|---|---|
| 2004/0047919 A1 | 3/2004 | Srivastava et al. |
| 2005/0142124 A1 | 6/2005 | Kaiser |
| 2006/0099244 A1 | 5/2006 | Guilford |
| 2007/0004639 A1 | 1/2007 | Kane et al. |
| 2007/0258938 A1 | 11/2007 | Roy et al. |

FOREIGN PATENT DOCUMENTS

WO WO 2007/005990 A2 1/2007

OTHER PUBLICATIONS

Calcagni et. al. Arch. Pharm. Pharm. Med. Chem., (Weinheim, Germany) (1996), 329(11), 498-502.*
Nagasawa et. al. Mechanisms of Ageing and Development, 120 (2000) 127-139.*
Burg et al. Peptidomimetic Glutathione Analogues as Novel γ-GT Stable GST Inhibitors, Bioorganic & Medicinal Chemistry 10 (2002) 195-205.*
CAS registry RN186097-67-6, 2002.*
Behrens, "Coenzymes for Glyoxalase", *J. Biol. Chem. 141*, 503-508 (1941).
Burg et al., "Peptidomimetic Glutathione Analogues as Novel γGT Stable GST Inhibitors", *Bioorganic & Medicinal Chemistry 10*, 195-205 (2002).
Calcagni et al., "Synthesis and Activity of the Glutathione Analogue γ-(L-γ-Oxaglutamyl)-L-cysteinyl-glycine", *Arch. Pharm. Pharm. Med. Chem.*, vol. 329 (11), 498-502 (1996).
Chen et al., "Role for glyoxalase-I in Alzheimer's disease", *PNAS* vol. 18, 7687-7692 (2004).
Hata et al., "Reaction of aziridinecarboxylic acids with thiols in aqueous solution the formation of beta-amino acid", *Tetrahedron* vol. 43 (17), 3881-3888 (1987).
Kobayashi et al., "Protective Effects of Glutathione Isopropyl Ester on the Sensitivity of Cultured Cells to UVB Irradiation", *Biol. Pharm. Bull.* 18 (9), 1219-1222 (1995).
Markesbery, "Oxidative stress hypothesis in Alzheimer's disease", *Free Radical Biology and Medicine*, vol. 23, 134-147 (1997).
Montine et al., "Antioxidants significantly affect the formation of different classes of isoprostanes and neuroprostanes in rat cerebral synaptosomes", *Biochemical Pharmacology* 65, 611-617 (2003).
More et al., "A metabolically stable tight-binding transition-state inhibitor of glyoxalase-I", *Bioorganic & Medicinal Chemistry Letters 16*, 6039-6042 (2006).
More et al., "Design, Synthesis and Biological Evaluation of Glutathione Peptidomimetics as Components of Anti-Parkinson Prodrugs", *J. Med. Chem. 51*, 4581-4588 (2008).
More et al., "Supporting Information, Design, Synthesis and Biological Evaluation of Glutathione Peptidomimetics as Components of Antiparkinson Prodrugs", *J. Med. Chem.* 51 (15), S1-S14 (2008).
More et al., "Inhibition of glyoxalase I: the first low-nanomolar tight-binding inhibitors", *J. Med. Chem. 52*, 4650-4656 (2009).
More et al., "Potential of a γ-Glutamyl-Transpeptidase-Stable Glutathione Analogue against Amyloid-β Toxicity", *ACS Chemical Neuroscience 3*, 204-210 (2012).

(Continued)

*Primary Examiner* — Jeanette Lieb
(74) *Attorney, Agent, or Firm* — Viksnins Harris & Padys PLLP

(57) ABSTRACT

The invention provides compounds of formula (I): (I) or salts thereof, wherein R1, R2, R3 Z, and X have any of the values defined herein, as well as compositions comprising such compounds. The compounds and compositions are useful for treating neurodegenerative disorders.

(I)

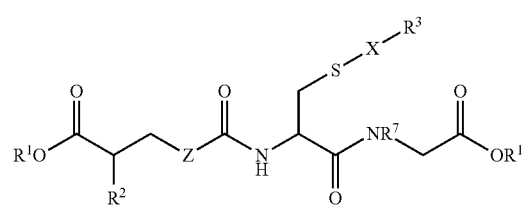

23 Claims, 10 Drawing Sheets

(56) References Cited

OTHER PUBLICATIONS

Patent Cooperation Treaty, International Searching Authority, Search Report and Written Opinion for PCT/US2012/045835, 16 pages, Sep. 27, 2012.

Pileblad et al., "Increase in rat brain glutathione following intracerebroventricular administration of gamma-glutamylcysteine", *Biochem. Pharmacol.* 44 (5), 895-903 (1992).

Queisser et al., "Hyperglycemia Impairs Proteasome Function by Methylglyoxal", *Diabetes 59*, 670-678 (2009).

Reitman et al., "Thiazoline ring induction in N-acetylglutathione", *Biochim. Biophys. Acta 208*, 157-159 (1970).

Trinchese et al., "Progressive age-related development of Alzheimer-like pathology in APP/PS1 mice", *Ann. Neurol.* 55 (6), 801-814 (2004).

Vince et al., "Studies on the inhibition of glyoxalase I by S-substituted glutathiones", *J. Med. Chem.* 14 (5), 402-404 (1971).

Wang et al., "Cell lysis with dimethyl sulphoxide produces stable homogeneous solutions in the dichlorofluorescein oxidative stress assay", *Free Radic. Res.* 42 (5), 435-441 (2008).

\* cited by examiner

GLUTATHIONE ANALOGS AND USES THEREOF

CROSS-REFERENCE TO RELATED APPLICATION(S)

This patent application claims the benefit of priority of U.S. application Ser. No. 61/505,898, filed Jul. 8, 2011, which application is herein incorporated by reference.

BACKGROUND OF THE INVENTION

Alzheimer's Disease (AD) is the seventh leading cause of death in the United States. With 5.3 million people currently suffering from the disease, the total expenditure on treatment is as high as 172 billion dollars per year. The AD-afflicted brain shows markedly high indicators of oxidative stress, an umbrella term that describes concentration of species causing oxidative protein, lipid and DNA modification. Examples of such stressors are $Fe^{2+}$, which can abstract an electron from dioxygen to form Reactive Oxygen Species (ROS). Glutathione (GSH) is the primary thiol reductant utilized by physiological pathways that counteract ROS. Unfortunately, GSH administration does not result in significant systemic elevation of GSH levels because of intestinal and hepatic γ-GT. Accordingly, new treatments are needed to treat neurodegenerative disorders, such as AD.

SUMMARY OF THE INVENTION

Accordingly there is provided a compound of the invention, which is a compound of formula (I):

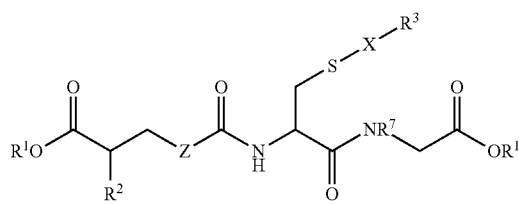

(I)

wherein:
each $R^1$ is independently H, $(C_1-C_6)$alkyl, $(C_3-C_8)$cycloalkyl, aryl$(C_1-C_6)$alkyl, or heteroaryl$(C_1-C_6)$alkyl;
each $R^{1a}$ is independently H, $(C_1-C_6)$alkyl, $(C_3-C_8)$cycloalkyl, aryl$(C_1-C_6)$alkyl, or heteroaryl$(C_1-C_6)$alkyl;
$R^2$ is OH, $NH_2$, —O—C(=O)—$R^{1a}$, —NH—C(=O)—$R^{1a}$ or —NH—C(=O)O—$R^{1a}$;
Z is —$CH_2$—, —NH—, —O—, or —S—;
X is —S— or absent, $R^3$ is H, $(C_1-C_6)$alkyl, —$(CH_2)$CH$(NHR^6)CO_2H$ or

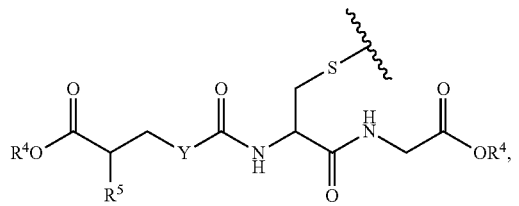

and $R^7$ is H; or X is absent, and $R^3$ and $R^7$ together with the atoms to which they are attached form a heterocycle, wherein the heterocycle is optionally substituted with one or more groups selected from oxo (=O), $(C_1-C_6)$alkyl, $(C_3-C_8)$cycloalkyl, aryl$(C_1-C_6)$alkyl and heteroatyl$(C_1-C_6)$alkyl;
each $R^4$ is independently H, $(C_1-C_6)$alkyl, $(C_3-C_8)$cycloalkyl, aryl$(C_1-C_6)$alkyl, or heteroaryl$(C_1-C_6)$alkyl;
$R^5$ is OH, $NH_2$, —O—C(=O)—$R^{1a}$, —NH—C(=O)—$R^{1a}$ or —NH—C(=O)O—$R^{1a}$;
$R^6$ is H, $(C_1-C_6)$alkyl or —C(=O)—$R^1$; and
Y is —$CH_2$—, —O—, —S— or NH;
or a salt thereof;
provided the compound of formula I is not a compound of formula:

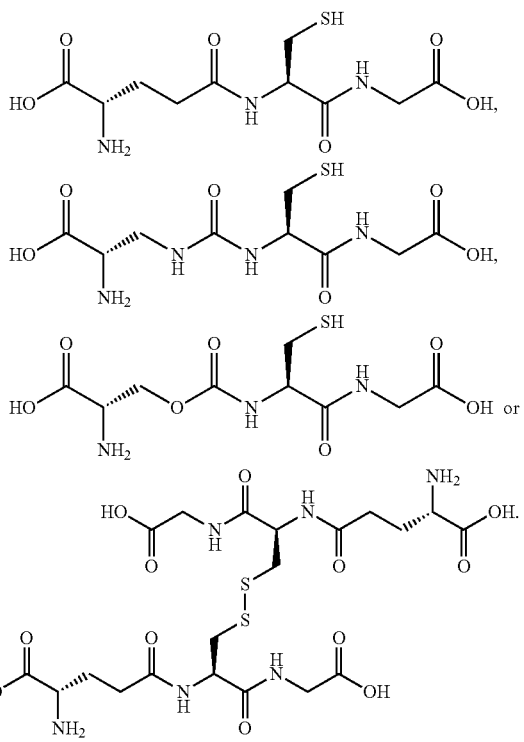

In certain embodiments there is provided a compound of the invention, which is a compound of formula (I'):

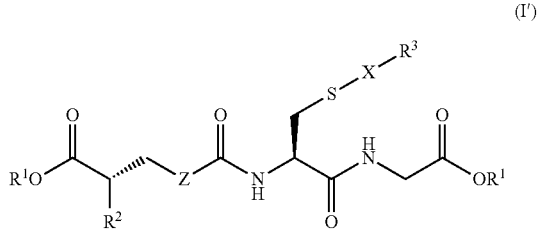

(I')

wherein:
each $R^1$ is independently H, $(C_1-C_6)$alkyl, $(C_3-C_8)$cycloalkyl, aryl$(C_1-C_6)$alkyl, or heteroaryl$(C_1-C_6)$alkyl;
$R^2$ is OH or $NH_2$, or O—C(=O)—$R^1$ or NH—C(=O)—$R^1$;
X is —S— or absent;
Z is —$CH_2$—, —NH—, —O—, or —S—;

$R^3$ is H or:

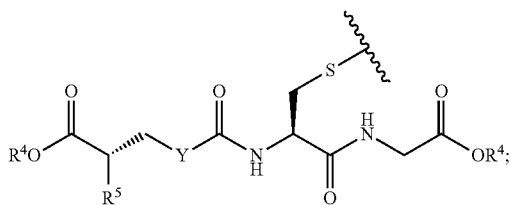

each $R^4$ is independently H, $(C_1-C_6)$alkyl, $(C_3-C_8)$cycloalkyl, aryl$(C_1-C_6)$alkyl, or heteroaryl$(C_1-C_6)$alkyl;

$R^5$ is OH or $NH_2$, or $O-C(=O)-R^1$ or $NH-C(=O)-R^1$; and

Y is $CH_2-$, $-O-$, or $S-$;

or a salt thereof;

provided that Z is not $-CH_2-$ when each $R^1$ is H, $R^2$ is $NH_2$, X is absent, and $R^3$ is H; and provided that Z is not $-NH-$ when each $R^1$ is H, $R^2$ is $NH_2$, X is absent, and $R^3$ is H; and provided that Z is not $-O-$ when each $R^1$ is H, $R^2$ is $NH_2$, X is absent, and $R^3$ is H.

In certain embodiments, the invention provides a method for treating Alzheimer's Disease, amyotrophic lateral sclerosis (ALS), diabetes, acetaminophen toxicity or stroke in a mammal, comprising administering a compound of formula I, (I)

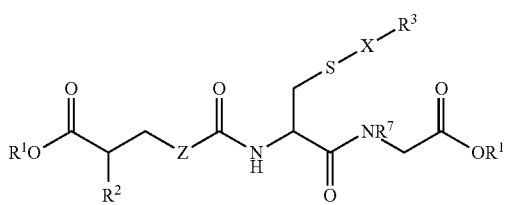

wherein:

each $R^1$ is independently H, $(C_1-C_6)$alkyl, $(C_3-C_8)$cycloalkyl, aryl$(C_1-C_6)$alkyl, or heteroaryl$(C_1-C_6)$alkyl;

each $R^{1a}$ is independently H, $(C_1-C_6)$alkyl, $(C_3-C_8)$cycloalkyl, aryl$(C_1-C_6)$alkyl, or heteroaryl$(C_1-C_6)$alkyl;

$R^2$ is OH, $NH_2$, $-O-C(=O)-R^{1a}$, $-NH-C(=O)-R^{1a}$ or $-NH-C(=O)O-R^{1a}$;

Z is $-CH_2-$, $-NH-$, $-O-$, or $-S-$;

X is $-S-$ or absent, $R^3$ is H, $(C_1-C_6)$alkyl, $-(CH_2)CH(NHR^6)CO_2H$ or

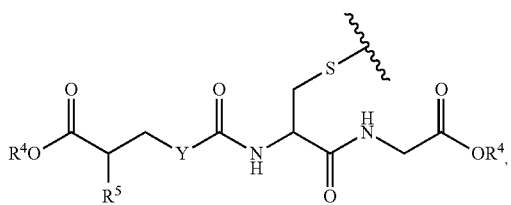

and $R^7$ is H; or X is absent, and $R^3$ and $R^7$ together with the atoms to which they are attached form a heterocycle, wherein the heterocycle is optionally substituted with one or more groups selected from oxo (=O), $(C_1-C_6)$alkyl, $(C_3-C_8)$cycloalkyl, aryl$(C_1-C_6)$alkyl and heteroaryl$(C_1-C_6)$alkyl;

each $R^4$ is independently H, $(C_1-C_6)$alkyl, $(C_3-C_8)$cycloalkyl, aryl$(C_1-C_6)$alkyl, or heteroaryl$(C_1-C_6)$alkyl;

$R^5$ is OH, $NH_2$, $-O-C(=O)-R^{1a}$, $-NH-C(=O)-R^{1a}$ or $-NH-C(=O)O-R^{1a}$;

$R^6$ is H, $(C_1-C_6)$alkyl or $-C(=O)-R^1$; and

Y is $-CH_2-$, $-O-$, $-S-$ or NH;

or a pharmaceutically acceptable salt thereof to the mammal.

In certain embodiments, the invention provides a method for treating Alzheimer's Disease, amyotrophic lateral sclerosis (ALS), diabetes, acetaminophen toxicity or stroke in a mammal, comprising administering a compound of formula I', (I')

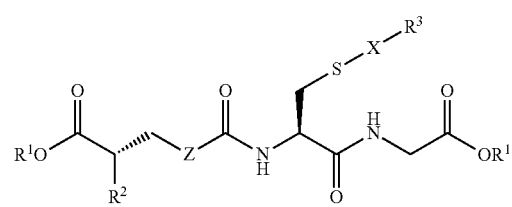

wherein:

each $R^1$ is independently H, $(C_1-C_6)$alkyl, $(C_3-C_8)$cycloalkyl, aryl$(C_1-C_6)$alkyl, or heteroaryl$(C_1-C_6)$alkyl;

$R^2$ is OH or $NH_2$, or $O-C(=O)-R^1$ or $NH-C(=O)-R^1$

X is $S-$ or absent;

Z is $-CH_2-$, $-NH-$, $-O-$, or $-S-$;

$R^3$ is H or:

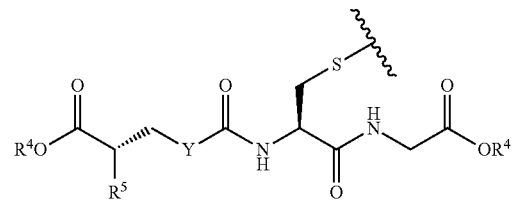

each $R^4$ is independently H, $(C_1-C_6)$alkyl, $(C_3-C_8)$cycloalkyl, aryl$(C_1-C_6)$alkyl, or heteroaryl$(C_1-C_6)$alkyl;

$R^5$ is OH or $NH_2$, or $O-C(=O)-R^1$ or $NH-C(=O)-R^1$; and

Y is $-CH_2-$, $-O-$, or $-S-$;

or a pharmaceutically acceptable salt thereof, to the mammal.

In certain embodiments, Z is not $-CH_2-$ when each $R^1$ is H, $R^2$ is $NH_2$, X is absent, and $R^3$ is H; and Z is not $-NH-$ when each $R^1$ is H, $R^2$ is $NH_2$, X is absent, and $R^3$ is H; and Z is not $-O-$ when each $R^1$ is H, $R^2$ is $NH_2$, X is absent, and $R^3$ is H.

In certain embodiments, Z is not $-CH_2-$ when each $R^1$ is H, $R^2$ is $NH_2$, X is absent, and $R^3$ is H; and Z is not $-NH-$ when each $R^1$ is H, $R^2$ is $NH_2$, X is absent, and $R^3$ is H; and Z is not $-O-$ when each $R^1$ is H, $R^2$ is $NH_2$, X is absent, and $R^3$ is H; and Y is not $CH_2$ when Z is $-CH_2-$, each $R^1$ and $R^4$ is H, each $R^2$ and $R^5$ is $NH_2$ and X is absent.

In certain embodiments there is provided a compound of the invention, which is a compound of formula I':

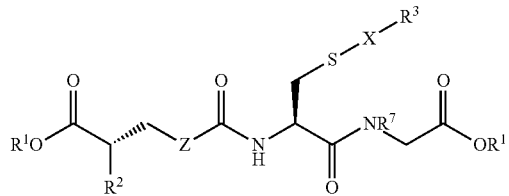

(I')

wherein:
each $R^1$ is independently H, $(C_1$-$C_6)$alkyl, $(C_3$-$C_8)$cycloalkyl, aryl$(C_1$-$C_6)$alkyl, or heteroaryl$(C_1$-$C_6)$alkyl;
each $R^{1a}$ is independently H, $(C_1$-$C_6)$alkyl, $(C_3$-$C_8)$cycloalkyl, aryl$(C_1$-$C_6)$alkyl, or heteroaryl$(C_1$-$C_6)$alkyl;
$R^2$ is OH, $NH_2$, —O—C(=O)—$R^{1a}$, —NH—C(=O)—$R^{1a}$ or —NH—C(=O)O—$R^{1a}$;
Z is —$CH_2$—, —NH—, —O—, or —S—;
X is —S— or absent, $R^3$ is H, $(C_1$-$C_6)$alkyl, —$(CH_2)$CH$(NHR^6)CO_2H$ or

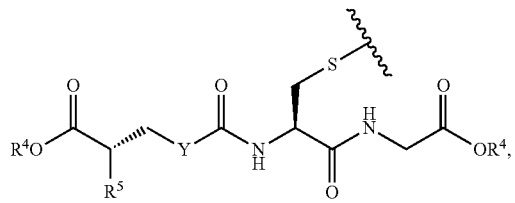

and $R^7$ is H; or X is absent, and $R^3$ and $R^7$ together with the atoms to which they are attached form a heterocycle, wherein the heterocycle is optionally substituted with one or more groups selected from oxo (=O), $(C_1$-$C_6)$alkyl, $(C_3$-$C_8)$cycloalkyl, aryl$(C_1$-$C_6)$alkyl and heteroaryl$(C_1$-$C_6)$alkyl;
each $R^4$ is independently H, $(C_1$-$C_6)$alkyl, $(C_3$-$C_8)$cycloalkyl, aryl$(C_1$-$C_6)$alkyl, or heteroaryl$(C_1$-$C_6)$alkyl;
$R^5$ is OH, $NH_2$, —O—C(=O)—$R^{1a}$, —NH—C(=O)—$R^{1a}$ or —NH—C(=O)O—$R^{1a}$;
$R^6$ is H, $(C_1$-$C_6)$alkyl or —C(=O)—$R^1$; and
Y is —$CH_2$—, —O—, —S— or NH;
or a salt thereof;
provided that Z is not —$CH_2$— when each $R^1$ is H, $R^2$ is $NH_2$, X is absent, and $R^3$ is H; and provided that Z is not —NH— when each $R^1$ is H, $R^2$ is $NH_2$, X is absent, and $R^3$ is H; and provided that Z is not —O— when each $R^1$ is H, $R^2$ is $NH_2$, X is absent, and $R^3$ is H; and provided Y is not $CH_2$ when Z is —$CH_2$—, each $R^1$ and $R^4$ is H, each $R^2$ and $R^5$ is $NH_2$ and X is absent.

In certain embodiments, each $R^1$ is independently H, methyl, cyclopentyl, benzyl, or thienylmethyl.
In certain embodiments, each $R^1$ is independently H, $(C_1$-$C_6)$alkyl or $(C_3$-$C_8)$cycloalkyl.
In certain embodiments, each $R^1$ is independently H, methyl, cyclopentyl, tert-butyl, isopropyl, benzyl, or thienylmethyl.
In certain embodiments, each $R^1$ is independently H, methyl, cyclopentyl, tert-butyl or isopropyl.
In certain embodiments, $R^2$ is OH.
In certain embodiments, $R^2$ is OH or $NH_2$.
In certain embodiments, $R^2$ is O—C(=O)—$R^1$ or NH—C(=O)—$R^1$.
In certain embodiments, $R^2$ is $NH_2$.
In certain embodiments, $R^2$ is $NH_2$, —NH—C(=O)—$R^{1a}$ or NH—C(=O)O—$R^{1a}$.
In certain embodiments, each $R^{1a}$ is independently $(C_1$-$C_6)$alkyl.
In certain embodiments, $R^2$ is $NH_2$, —NHC(=O)$CH_3$ or —NHC(=O)CO(CH_3)_3$.
In certain embodiments, X is —S—.
In certain embodiments, X is absent.
In certain embodiments, Z is —$CH_2$—.
In certain embodiments, Z is —NH—.
In certain embodiments, Z is —O—.
In certain embodiments, Z is —S—.
In certain embodiments, Z is —NH—, —O—, or —S—.
In certain embodiments, Z is —NH— or —O—.
In certain embodiments, $R^7$ is H.
In certain embodiments, $R^3$ is H.
In certain embodiments, $R^3$ is:

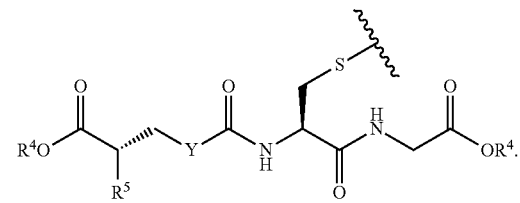

In certain embodiments, $R^3$ is H, $(C_1$-$C_6)$alkyl or

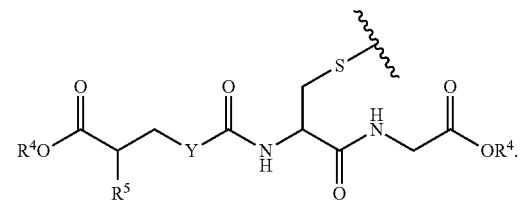

In certain embodiments, $R^3$ is H, $(C_1$-$C_6)$alkyl or

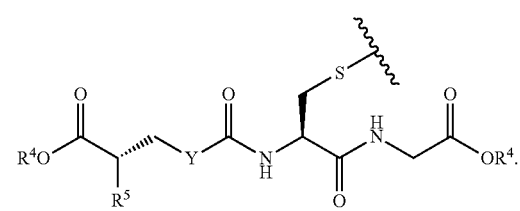

In certain embodiments, $R^3$ is H, tert-butyl or

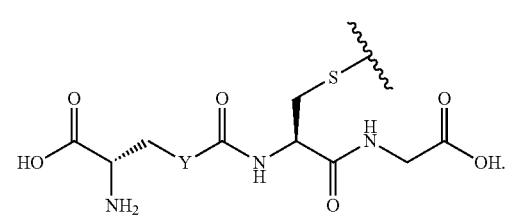

In certain embodiments, there is provided a compound of the invention, which is a compound of formula Ia:

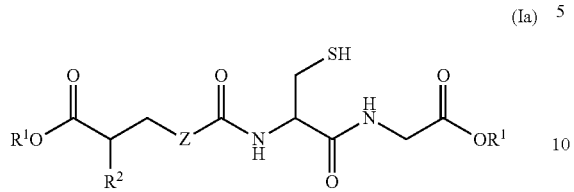
(Ia)

or a salt thereof

In certain embodiments, there is provided a compound of the invention, which is a compound of formula Ia':

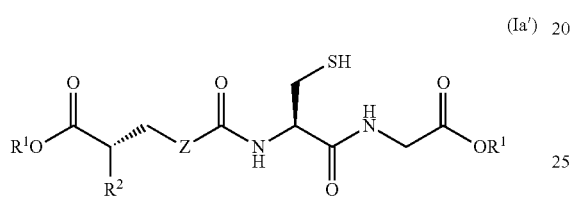
(Ia')

or a salt thereof

In certain embodiments, each $R^4$ is independently H, methyl, cyclopentyl, benzyl, or thienylmethyl.

In certain embodiments, $R^5$ is OH.

In certain embodiments, $R^5$ is OH or $NH_2$.

In certain embodiments, $R^5$ is O—C(=O)—$R^1$ or NH—C(=O)—$R^1$.

In certain embodiments, each $R^5$ is $NH_2$.

In certain embodiments, Y is —$CH_2$—.

In certain embodiments, Y is —O—.

In certain embodiments, Y is —S—.

In certain embodiments, the invention provides a compound of formula Ib:

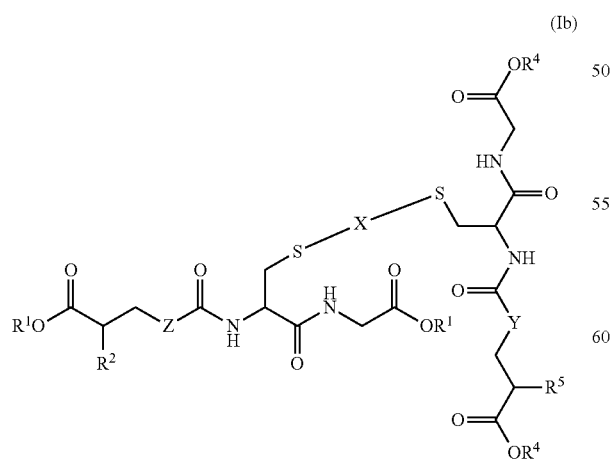
(Ib)

or a salt thereof.

In certain embodiments, the invention provides a compound of formula Ib':

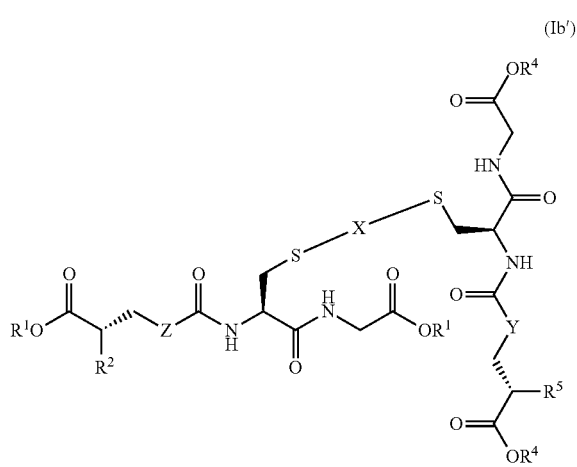
(Ib')

or a salt thereof.

In certain embodiments, $R^4$ is H, ($C_1$-$C_6$)alkyl or ($C_3$-$C_8$)cycloalkyl; $R^5$ is $NH_2$, —NH—C(=O)—$R^{1a}$ or —NH—C(=O)O—$R^{1a}$; and Y is —NH—, —O—, or —S—.

In certain embodiments, $R^4$ is H; $R^5$ is $NH_2$; and Y is —NH—.

In certain embodiments, there is provided a compound of the invention, which is a compound of formula Id:

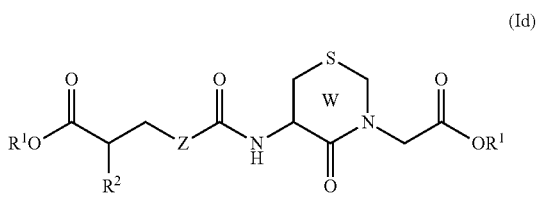
(Id)

wherein the heterocycle W is optionally substituted with one or more groups selected from oxo (=O), ($C_1$-$C_6$)alkyl, ($C_3$-$C_8$)cycloalkyl, aryl($C_1$-$C_6$)alkyl and heteroaryl($C_1$-$C_6$)alkyl, or a salt thereof.

In certain embodiments, there is provided a compound of the invention, which is a compound of formula Id':

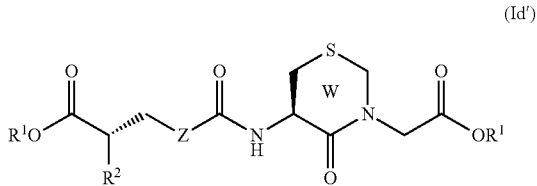
(Id')

wherein the heterocycle W is optionally substituted with one or more groups selected from oxo (=O), ($C_1$-$C_6$)alkyl, ($C_3$-$C_8$)cycloalkyl, aryl($C_1$-$C_6$)alkyl and heteroaryl($C_1$-$C_6$)alkyl, or a salt thereof.

In certain embodiments, there is provided a compound of the invention, which is a compound of formula Ie:

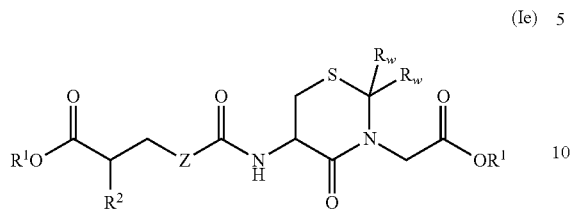
(Ie)

wherein each $R_w$ is optionally H or $(C_1-C_6)$alkyl, or a salt thereof.

In certain embodiments, there is provided a compound of the invention, which is a compound of formula Ie':

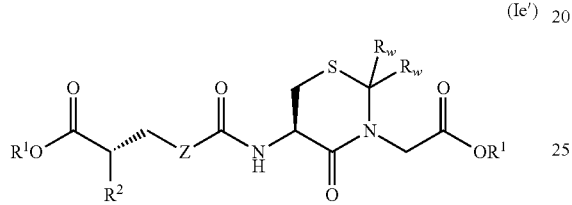
(Ie')

wherein each $R_w$ is optionally H or $(C_1-C_6)$alkyl, or a salt thereof.

In certain embodiments, there is provided a compound of the invention, which is a compound of formula If:

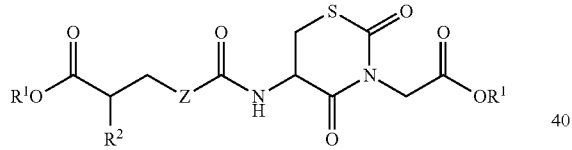
(If)

or a salt thereof.

In certain embodiments, there is provided a compound of the invention, which is a compound of formula If':

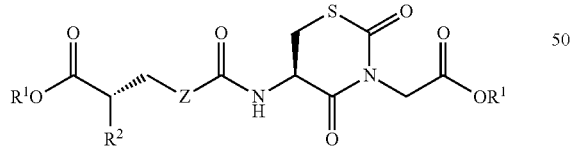
(If')

or a salt thereof.

In certain embodiments, the invention provides a compound of formula:

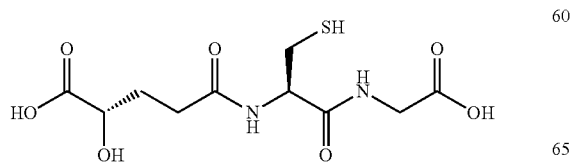

or a salt thereof.

In certain embodiments, the invention does not include a compound of formula:

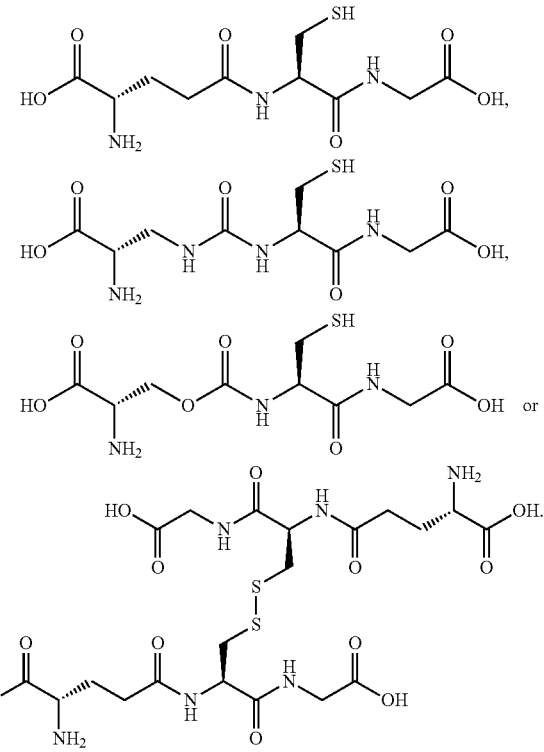

In certain embodiments, the invention does not include a compound of formula:

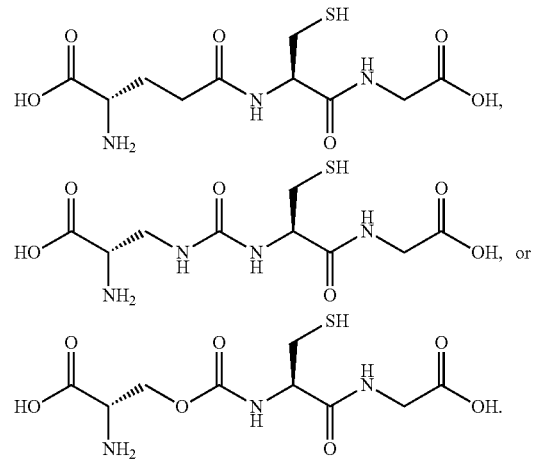

In certain embodiments, the invention does not include a compound of formula:

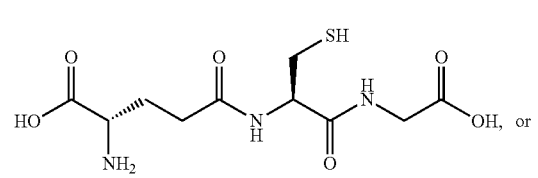

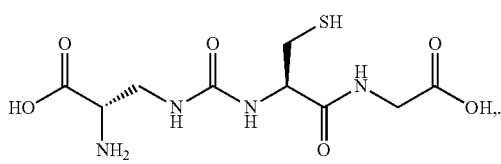
In certain embodiments, the invention does not include a compound of formula:
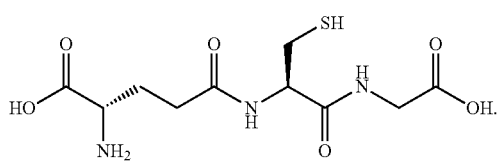 [SMILES: N[C@@H](CCC(=O)N[C@@H](CS)C(=O)NCC(=O)O)C(=O)O]
In certain embodiments, the invention does not include a compound of formula:
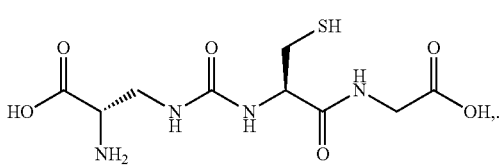
In certain embodiments, the invention provides a compound of formula:
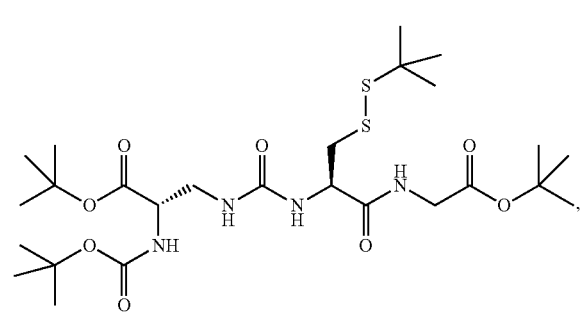
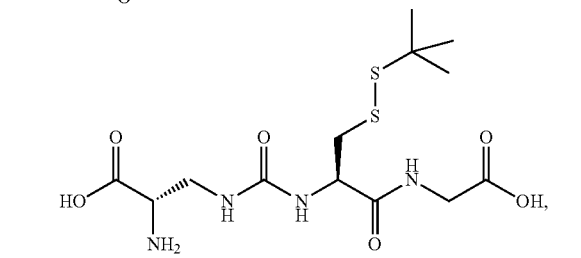
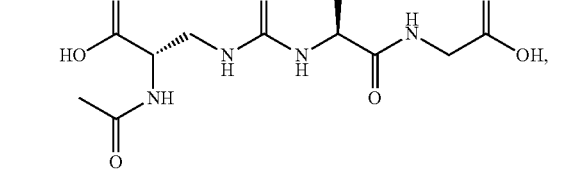
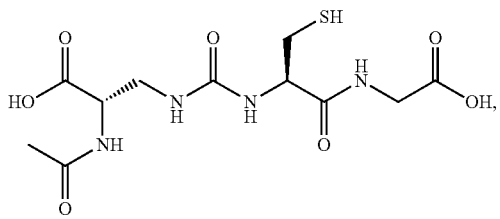

13
-continued

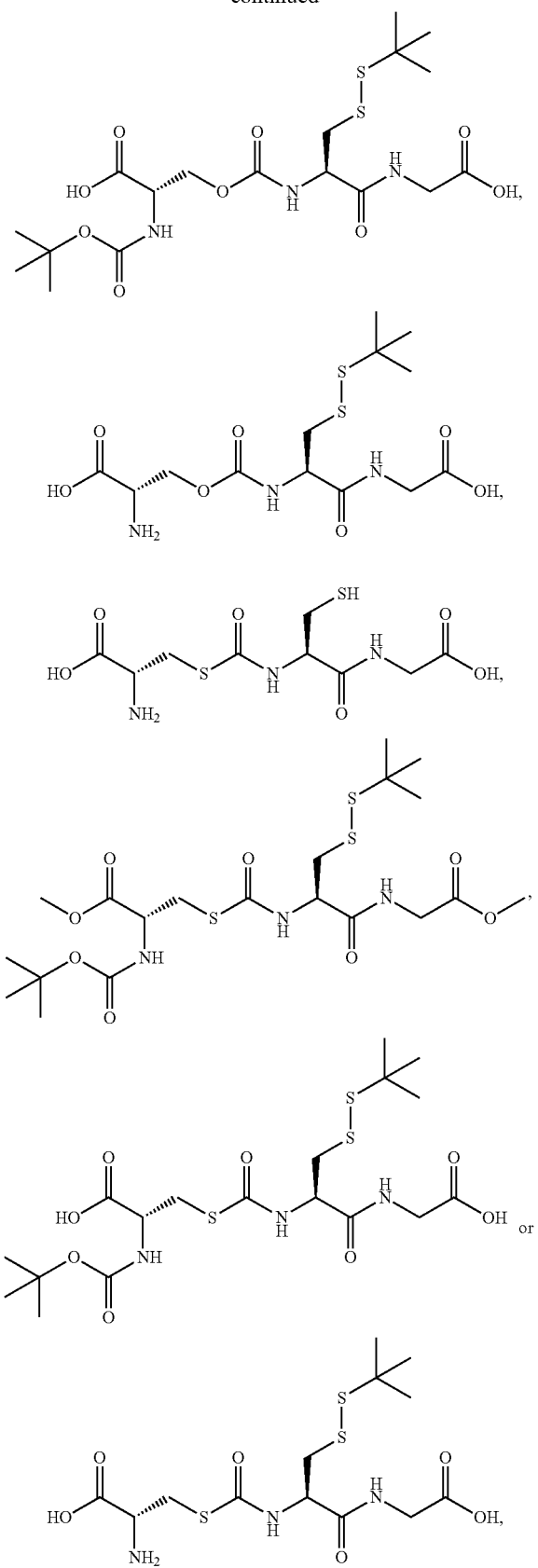

or a salt thereof.

14

In certain embodiments, the invention provides a compound of formula:

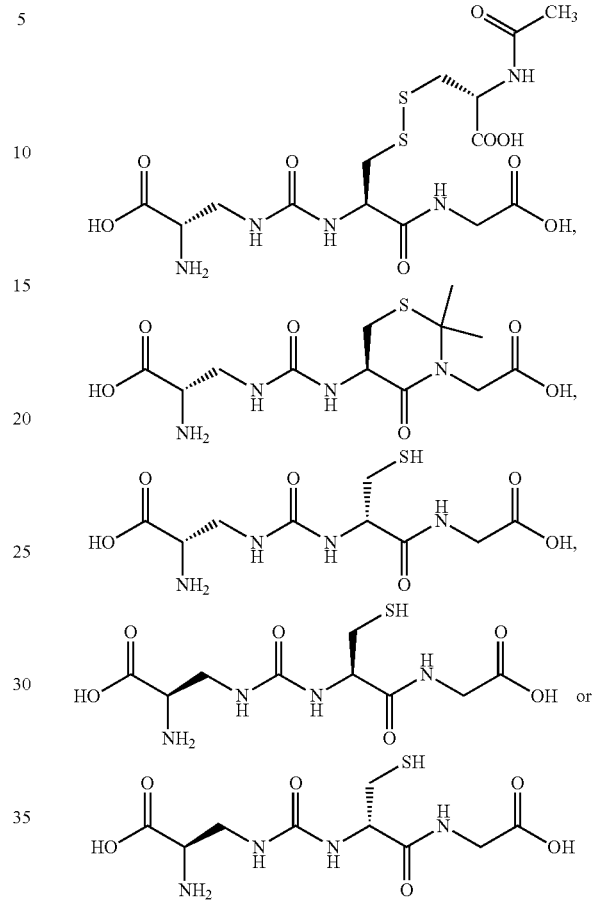

or a salt thereof.

In certain embodiments, the invention provides a pharmaceutical composition comprising a compound of formula I as described herein, or a pharmaceutically acceptable salt thereof, and a pharmaceutically acceptable diluent or carrier.

In certain embodiments, the composition is in the form of a dermatological composition.

In certain embodiments, the invention provides a method for treating a neurodegenerative disorder in a mammal, comprising administering a compound of formula I as described herein, or a pharmaceutically acceptable salt thereof, to the mammal.

In certain embodiments, the neurodegenerative disorder is Parkinson's Disease.

In certain embodiments, the method treats a reperfusion injury.

In certain embodiments, the invention provides compound described herein for use in therapy.

In certain embodiments, the invention provides compound described herein treating a neurodegenerative disorder.

In certain embodiments, the invention provides compound described herein for treating Alzheimer's Disease, amyotrophic lateral sclerosis (ALS), diabetes, acetaminophen toxicity or a stroke.

In certain embodiments, the method or use is for treating Alzheimer's Disease.

In certain embodiments, the method or use is for treating amyotrophic lateral sclerosis (ALS).

In certain embodiments, the method or use is for treating diabetes.

In certain embodiments, the method or use is for treating acetaminophen toxicity.

In certain embodiments, the method or use is for treating a stroke.

In certain embodiments, the invention provides a compound of formula I or a pharmaceutically acceptable salt thereof for the therapeutic or prophylactic treatment of a neurodegenerative disorder provided the compound is not glutathione.

In certain embodiments, the invention provides a compound of formula I, or a pharmaceutically acceptable salt thereof for the manufacture of a medicament for the treatment of a neurodegenerative disorder in a mammal provided the compound is not glutathione.

In certain embodiments, the invention provides a compound of formula I or a pharmaceutically acceptable salt thereof for the prophylactic or therapeutic treatment of Alzheimer's Disease, amyotrophic lateral sclerosis (ALS), diabetes, acetaminophen toxicity or a stroke.

In certain embodiments, the invention provides a compound of formula I or a pharmaceutically acceptable salt thereof for the manufacture of a medicament for the treatment of Alzheimer's Disease, amyotrophic lateral sclerosis (ALS), diabetes, acetaminophen toxicity or a stroke in a mammal.

In certain embodiments, the invention provides a compound of formula I, or a salt thereof for topical administration.

In certain embodiments, the invention provides a compound of formula I for a composition in the form of a cosmetic, sunscreen or anti-wrinkling composition.

In certain embodiments, the invention provides a compound of formula I for a method for producing an anti-oxidant effect in a mammal in need thereof comprising administering an effective amount of compound of formula I, or a salt thereof, to the mammal.

In certain embodiments, the invention provides a compound of formula I wherein the compound of formula I or a salt thereof is administered in the form of a cosmetic, sunscreen or anti-wrinkling composition.

The invention also provides processes and intermediates disclosed herein that are useful for preparing compounds of formula (I) or salts thereof.

DETAILED DESCRIPTION

Figure 1:
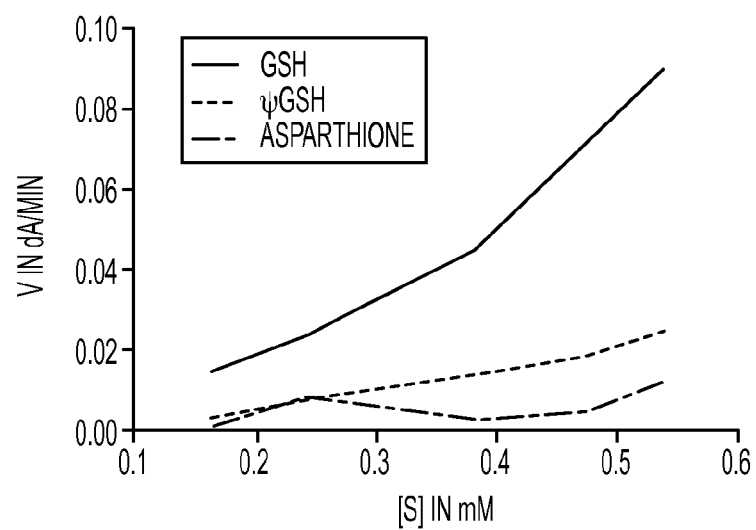
FIG. 1. Glyoxalase I enzyme kinetics assay. GSH (upper trace) or ΨGSH (middle trace) at various concentrations was incubated with MG at 30° C. in phosphate buffer (0.05 M, pH 6.6) for 6 min to allow formation of the hemimercaptal 2, followed by the addition of yeast Glx-I. The enzyme reaction was monitored for 180 sec by measuring the increase in absorption at 240 nm. Rates of enzymatic reaction were plotted against substrate concentrations. Data shown here is representative of three independent experiments.

Alzheimer's Disease (AD) is the seventh leading cause of death in the United States. With 5.3 million people currently suffering from the disease, the total expenditure on treatment is as high as 172 billion dollars per year. Exceptions aside, AD is a disease of aging whose causative factors are incompletely delineated; nevertheless, its pathology is well-defined. In the absence of other disease states, adult onset dementia is an empirical indicator of AD. Prominent microscopic markers are extracellular Senile Plaques (SP, amyloidosis) and intracellular NeuroFibrillary Tangles (NFTs). Both of these neuropathologies are shown to negatively affect synaptic function. The AD-afflicted brain shows markedly high indicators of oxidative stress, an umbrella term that describes concentration of species causing oxidative protein, lipid and DNA modification. Examples of such stressors are $Fe^{2+}$, which can abstract an electron from dioxygen to form Reactive Oxygen Species (ROS) such as the superoxide radical ($O_2$) and hydrogen peroxide as well as dicarbonyl species such as methylglyoxal (MG) and glyoxal. Condensation of glucose and dicarbonyl compounds with amino groups of proteins is also an oxidative stressor, as the Schiff bases can then rearrange and/or react further to form irreversibly modified proteins (Advanced Glycosylation End products, AGEs).

SPs are aggregates of the 42-amino acid amyloid-β peptide (Aβ), derived in turn from the Amyloid Precurssor Protein (APP), a structural and functional component of synapses. β and γ-Secretases cleave APP into Aβ, which is in turn metabolized by a range of zinc metalloproteinases. Products of APP cleavage, including Aβ, participate in regulation of excitatory neurotransmission and may fulfill other hitherto unknown electrophysiological roles. While production of Aβ is a normal physiological event, conformational changes in Aβ that lead to its aggregation have no known physiological roles. Among the three interchanging solution conformations of Aβ viz., a random coil, an α-helix or a β-sheet, the latter possesses a dramatically higher tendency to aggregate. Aβ in an antiparallel β-sheet conformation nucleates fibrillogenesis, with other monomers assuming similar conformation to result initially in soluble aggregates. Higher order aggregation eventually forms fibrils and progressively renders the growing aggregate insoluble. Nucleation is shown to be rate-limiting for Aβ aggregation. MG-modified Aβ peptides known to more potently nucleate aggregate formation than the unmodified peptides. AGEs upregulate APP expression through increase in ROS concentrations, adding to their propensity to cause Aβ aggregate formation. NFTs are made of stable aggregated bifilar helices (paired helical fragments, PHF) derived from the microtubule stabilizing τ-proteins. Phosphorylation and covalent (AGE) modification of the lysine residues in the tubilin-binding motif of τ-proteins promote its detachment from tubulin and subsequent aggregation. Aβ fibrils are known to induce τ-phosphorylation, decrease microtubule binding of τ-proteins, thereby promoting NFT formation. ROS thus influence the formation of both of these abnormal protein aggregates.

Glutathione (GSH) is the primary thiol reductant utilized by physiological pathways that counteract ROS. GSH levels are dynamically maintained through its consumption by detoxifying enzymes, e.g., glutathione peroxidase (GSHPx) and by metabolic enzymes, e.g., γ-glutamyl transpeptidase (γ-GT), its de novo synthesis involving glutamate cysteine ligase (GCL), glutathione synthetase (GSS) and regeneration mediated by glutathione reductase (GR). Aging tissue shows upregulation of GSHPx, Glx-I and GR, but reduced GCL activity either through downregulation of expression or through impairment of the enzyme's catalytic subunit. GSH levels are invariably depleted in aging and AD-afflicted brain. Whether GSH depletion is secondary to AD development or is a contributory factor is indeterminate, nevertheless, elevation of GSH levels as a means to counteract the oxidative damage in AD is a well-supported hypothesis. Unfortunately, GSH administration does not result in significant systemic elevation of GSH levels because of intestinal and hepatic γ-GT.

Currently, there is no known drug that mimics the antioxidant and other metabolic properties of GSH while being stable to gamma-glutamyl transpeptidase. Where existing technologies merely supplement existing antioxidant molecules in the body without addressing the root causes of their deficiency, described herein is the use of a GSH analog that can substitute for GSH while providing a molecular framework that contains a metabolically stable gammaglutamylcysteine linkage. It quenches the reactive dicarbonyls such as methylglyoxal due to its glyoxalase I substrate activity, thus fighting the root cause of oxidative stress generation in neurodegenerative disorders like Alzheimer's.

It has been demonstrated that a metabolically stable GSH analog, "pseudo-GSH", is superior to GSH in preventing Alzheimer's-related beta-amyloid toxicity toward neuronal cells. The utilization of the same cell uptake system by GSH and pseudo-GSH, which is also expressed at the blood brain bather was demonstrated. Additionally, the new GSH analog is a substrate of enzyme glyoxalase I.

The following definitions are used, unless otherwise described: halo is fluoro, chloro, bromo, or iodo. Alkyl, alkoxy, alkenyl, alkynyl, etc. denote both straight and branched groups; but reference to an individual radical such as propyl embraces only the straight chain radical, a branched chain isomer such as isopropyl being specifically referred to. Aryl denotes a phenyl radical or an ortho-fused bicyclic carbocyclic radical having about nine to ten ring atoms in which at least one ring is aromatic. Heteroaryl encompasses a radical of a monocyclic aromatic ring containing five or six ring atoms consisting of carbon and one to four heteroatoms each selected from the group consisting of non-peroxide oxygen, sulfur, and N(X) wherein X is absent or is H, O, $(C_1-C_4)$alkyl, phenyl or benzyl, as well as a radical of an ortho-fused bicyclic heterocycle of about eight to ten ring atoms comprising one to four heteroatoms each selected from the group consisting of non-peroxide oxygen, sulfur, and N(X).

The term "heterocycle" or "heterocyclic" or "heterocyclyl" as used herein refers to a single saturated or partially unsaturated ring (e.g. 3, 4, 5, 6, 7 or 8-membered ring) from about 1 to 7 carbon atoms and from about 1 to 3 heteroatoms selected from the group consisting of oxygen, nitrogen and sulfur in the rings. The sulfur and nitrogen atoms may also be present in their oxidized forms.

It will be appreciated by those skilled in the art that compounds of the invention having a chiral center may exist in and be isolated in optically active and racemic forms. Some compounds may exhibit polymorphism. It is to be understood that the present invention encompasses any racemic, optically-active, polymorphic, or stereoisomeric form, or mixtures thereof, of a compound of the invention, which possess the useful properties described herein, it being well known in the art how to prepare optically active forms (for example, by resolution of the racemic form by recrystallization techniques, by synthesis from optically-active starting materials, by chiral synthesis, or by chromatographic separation using a chiral stationary phase.

It is to be understood that for compounds of the invention when a bond is drawn in a non-stereochemical manner (e.g. flat) the atom to which the bond is attached includes all stereochemical possibilities. It is also to be understood that when a bond is drawn in a stereochemical manner (e.g. bold, bold-wedge, dashed or dashed-wedge) the atom to which the stereochemical bond is attached has the stereochemistry as shown unless otherwise noted.

Accordingly, in one embodiment, a compound of the invention may be greater than 50% a single enantiomer. In another embodiment, a compound of the invention may be at least 51% a single enantiomer. In another embodiment, a compound of the invention may be at least 60% a single enantiomer. In another embodiment, a compound of the invention may be at least 70% a single enantiomer. In another embodiment, a compound of the invention may be at least 80% a single enantiomer. In another embodiment, a compound of the invention may be at least 90% a single enantiomer. In another embodiment, a compound of the invention may be at least 95% a single enantiomer. In another embodiment, a compound of the invention may be at least 98% a single enantiomer. In another embodiment, a compound of the invention may be at least 99% a single enantiomer. In another embodiment, a compound of the invention may be greater than 50% a single diasteromer. In another embodiment, a compound of the invention may be at least 51% a single diasteromer. In another embodiment, a compound of the invention may be at least 60% a single diastereomer. In another embodiment, a compound of the invention may be at least 70% a single diastereomer. In another embodiment, a compound of the invention may be at least 80% a single diastereomer. In another embodiment, a compound of the invention may be at least 90% a single diastereomer. In another embodiment, the compounds of the invention are at least 95% a single diastereomer. In another embodiment, a compound of the invention may be at least 98% a single diastereomer. In another embodiment, a compound of the invention may be at least 99% a single diastereomer.

Specific values listed below for radicals, substituents, and ranges, are for illustration only; they do not exclude other defined values or other values within defined ranges for the radicals and substituents Specifically, $(C_1-C_6)$alkyl can be methyl, ethyl, propyl, isopropyl, butyl, iso-butyl, sec-butyl, pentyl, 3-pentyl, or hexyl; $(C_3-C_6)$cycloalkyl can be cyclopropyl, cyclobutyl, cyclopentyl, or cyclohexyl; $(C_3-C_8)$cycloalkyl$(C_1-C_6)$alkyl can be cyclopropylmethyl, cyclobutylmethyl, cyclopentylmethyl, cyclohexylmethyl, 2-cyclopropylethyl, 2-cyclobutylethyl, 2-cyclopentylethyl, or 2-cyclohexylethyl; aryl can be phenyl, indenyl, or naphthyl; and heteroaryl can be furyl, imidazolyl, triazolyl, triazinyl, oxazoyl, isoxazoyl, thiazolyl, isothiazoyl, pyrazolyl, pyrrolyl, pyrazinyl, tetrazolyl, pyridyl, (or its N-oxide), thienyl, pyrimidinyl (or its N-oxide), indolyl, isoquinolyl (or its N-oxide) or quinolyl (or its N-oxide).

Processes for preparing compounds of formula I are provided as further embodiments of the invention and are illustrated by the following procedures in which the meanings of the generic radicals are as given above unless otherwise qualified.

In cases where compounds are sufficiently basic or acidic, a salt of a compound of formula I can be useful as an intermediate for isolating or purifying a compound of formula I. Additionally, administration of a compound of formula I as a pharmaceutically acceptable acid or base salt may be appropriate. Examples of pharmaceutically acceptable salts are organic acid addition salts formed with acids which form a physiological acceptable anion, for example, tosylate, methanesulfonate, acetate, citrate, malonate, tartarate, succinate, benzoate, ascorbate, α-ketoglutarate, and α-glycerophosphate. Suitable inorganic salts may also be formed, including hydrochloride, sulfate, nitrate, bicarbonate, and carbonate salts.

Pharmaceutically acceptable salts may be obtained using standard procedures well known in the art, for example by reacting a sufficiently basic compound such as an amine with a suitable acid affording a physiologically acceptable anion. Alkali metal (for example, sodium, potassium or lithium) or alkaline earth metal (for example calcium) salts of carboxylic acids can also be made.

The compounds of formula I can be formulated as pharmaceutical compositions and administered to a mammalian host, such as a human patient in a variety of forms adapted to the chosen route of administration, e.g., orally or parenterally, intranasally by intravenous, intramuscular, topical or subcutaneous routes or in suppository form.

Thus, the present compounds may be systemically administered, e.g., orally, in combination with a pharmaceutically acceptable vehicle such as an inert diluent or an assimilable edible carrier. They may be enclosed in hard or soft shell gelatin capsules, may be compressed into tablets, or may be incorporated directly with the food of the patient's diet. For oral therapeutic administration, the active compound may be combined with one or more excipients and used in the form of ingestible tablets, buccal tablets, troches, capsules, elixirs, suspensions, syrups, wafers, and the like. Such compositions and preparations should contain at least 0.1% of active compound. The percentage of the compositions and preparations may, of course, be varied and may conveniently be between about 2 to about 60% of the weight of a given unit dosage form. The amount of active compound in such therapeutically useful compositions is such that an effective dosage level will be obtained.

The tablets, troches, pills, capsules, and the like may also contain the following: binders such as gum tragacanth, acacia, corn starch or gelatin; excipients such as dicalcium phosphate; a disintegrating agent such as corn starch, potato starch, alginic acid and the like; a lubricant such as magnesium stearate; and a sweetening agent such as sucrose, fructose, lactose or aspartame or a flavoring agent such as peppermint, oil of wintergreen, or cherry flavoring may be added. When the unit dosage form is a capsule, it may contain, in addition to materials of the above type, a liquid carrier, such as a vegetable oil or a polyethylene glycol. Various other materials may be present as coatings or to otherwise modify the physical form of the solid unit dosage form. For instance, tablets, pills, or capsules may be coated with gelatin, wax, shellac or sugar and the like. A syrup or elixir may contain the active compound, sucrose or fructose as a sweetening agent, methyl and propylparabens as preservatives, a dye and flavoring such as cherry or orange flavor. Of course, any material used in preparing any unit dosage form should be pharmaceutically acceptable and substantially non-toxic in the amounts employed. In addition, the active compound may be incorporated into sustained-release preparations and devices.

The active compound may also be administered intravenously, intraperitoneally or intramuscularly by infusion or injection. Solutions of the active compound or its salts can be prepared in water, optionally mixed with a nontoxic surfactant. Dispersions can also be prepared in glycerol, liquid polyethylene glycols, triacetin, and mixtures thereof and in oils. Under ordinary conditions of storage and use, these preparations contain a preservative to prevent the growth of microorganisms.

The pharmaceutical dosage forms suitable for injection or infusion can include sterile aqueous solutions or dispersions or sterile powders comprising the active ingredient which are adapted for the extemporaneous preparation of sterile injectable or infusible solutions or dispersions, optionally encapsulated in liposomes. In all cases, the ultimate dosage form should be sterile, fluid and stable under the conditions of manufacture and storage. The liquid carrier or vehicle can be a solvent or liquid dispersion medium comprising, for example, water, ethanol, a polyol (for example, glycerol, propylene glycol, liquid polyethylene glycols, and the like), vegetable oils, nontoxic glyceryl esters, and suitable mixtures thereof. The proper fluidity can be maintained, for example, by the formation of liposomes, by the maintenance of the required particle size in the case of dispersions or by the use of surfactants. The prevention of the action of microorganisms can be brought about by various antibacterial and antifungal agents, for example, parabens, chlorobutanol, phenol, sorbic acid, thimerosal, and the like. In many cases, it will be preferable to include isotonic agents, for example, sugars, buffers or sodium chloride. Prolonged absorption of the injectable compositions can be brought about by the use in the compositions of agents delaying absorption, for example, aluminum monostearate and gelatin.

Sterile injectable solutions are prepared by incorporating the active compound in the required amount in the appropriate solvent with various of the other ingredients enumerated above, as required, followed by filter sterilization. In the case of sterile powders for the preparation of sterile injectable solutions, the preferred methods of preparation are vacuum drying and the freeze drying techniques, which yield a powder of the active ingredient plus any additional desired ingredient present in the previously sterile-filtered solutions.

Useful dosages of the compounds of formula I can be determined by comparing their in vitro activity, and in vivo activity in animal models. Methods for the extrapolation of effective dosages in mice, and other animals, to humans are known to the art; for example, see U.S. Pat. No. 4,938,949.

The amount of the compound, or an active salt or derivative thereof, required for use in treatment will vary not only with the particular salt selected but also with the route of administration, the nature of the condition being treated and the age and condition of the patient and will be ultimately at the discretion of the attendant physician or clinician.

In general, however, a suitable dose will be in the range of from about 0.5 to about 100 mg/kg, e.g., from about 10 to about 75 mg/kg of body weight per day, such as 3 to about 50 mg per kilogram body weight of the recipient per day, preferably in the range of 6 to 90 mg/kg/day, most preferably in the range of 15 to 60 mg/kg/day. In certain embodiments, the suitable dosage will be up to about 2 g/kg, which may be formulated in unit dosage form.

The compound is conveniently formulated in unit dosage form; for example, containing 5 to 1000 mg, conveniently 10 to 750 mg, most conveniently, 50 to 500 mg of active ingredient per unit dosage form. In one embodiment, the invention provides a composition comprising a compound of the invention formulated in such a unit dosage form.

The desired dose may conveniently be presented in a single dose or as divided doses administered at appropriate intervals, for example, as two, three, four or more sub-doses per day. The sub-dose itself may be further divided, e.g., into a number of discrete loosely spaced administrations; such as multiple inhalations from an insufflator or by application of a plurality of drops into the eye.

The compounds of formula I can be formulated as dermatological compositions and applied to a mammalian host, such as a human by a topical route. For topical administration, the present compounds may be applied in pure form, i.e., when they are liquids. However, it will generally be desirable to administer them to the skin as compositions or formulations, in combination with a dermatologically acceptable carrier, which may be a solid or a liquid. Useful solid carriers include finely divided solids such as talc, clay, microcrystalline cellulose, silica, alumina and the like. Useful liquid carriers include water, alcohols or glycols or water-alcohol/glycol blends, in which the present compounds can be dissolved or dispersed at effective levels, optionally with the aid of non-toxic surfactants. Adjuvants such as fragrances and additional antimicrobial agents can be added to optimize the properties for a given use. The resultant liquid compositions can be applied from absorbent pads, used to impregnate bandages and other dressings, or sprayed onto the affected area using pump-type or aerosol sprayers. Thickeners such as synthetic polymers, fatty acids, fatty acid salts and esters, fatty alcohols, modified celluloses or modified mineral materials can also be employed with liquid carriers to form spreadable pastes, gels, ointments, soaps, and the like, for application directly to the skin of the user. Cosmetic compositions, may contain conventional ingredients known to those of ordinary skill in the art, such as those described in Kirk-Othmer, Encyclopedia of Chemical Technology, Third Edition (1979), Vol. 7, pages 143-176. In addition, topical preparations and cosmetic formulations may be prepared as described in U.S. Pat. Nos. 4,199,576, 4,136,165, and 4,248,861. Examples of additional useful dermatological compositions which can be used to deliver the compounds of the invention to the skin are known to the art; for example, see Jacquet et al. (U.S. Pat. No. 4,608,392), Geria (U.S. Pat. No. 4,992,478), Smith et al. (U.S. Pat. No. 4,559,157) and Wortzman (U.S. Pat. No. 4,820,508). The CTFA Cosmetic Ingredient Handbook, Second Edition (1992) describes a wide variety of non-limiting cosmetic and pharmaceutical ingredients commonly used in the skin care industry, which are suitable for use in the articles of the present invention.

The percentage of the compositions and preparations may be varied. In general, a suitable dermatological composition will typically comprise a compound of formula I or a mixture thereof and may conveniently be between about 2-12% of the weight of a dermatological composition. The amount of active compound in such dermatological useful compositions is such that an effective level of compound will be obtained and/or maintained for the desired duration of action.

The compounds of formula I may be useful as glutathione substitutes. Accordingly, the compounds of formula I may be useful for a variety applications wherein glutathione has been implicated to have utility. These applications include but are not limited to those applications wherein the use of glutathione imparts a unique property (e.g. anti-oxidant properties). For example, the compounds of formula I may be useful in topical applications such as cosmetics, sunscreens, creams, ointments (e.g. anti-wrinkling ointments) and the like wherein a property such as an anti-oxidant property is desirable.

As glutathione substitutes the compounds of formula I may also be useful in maintaining or improving neural health, for example, by providing an anti-oxidant property. In addition, the compounds of formula I may also be useful as additives to health foods or as nutraceuticals.

Compounds of formula I may also be useful as rescue agents against toxins or poisons that act by virtue of producing oxidative damage to organs. For example, Ψ-GSH is demonstrated to be useful as rescue agent against acetaminophen (ACP) toxicity.

Compounds of formula I, due to their ability to substitute for GSH, may be useful in countering acutely induced oxidative and alkylative damage. An example is acute bronchiolitis obliterans in popcorn factory workers, caused by the flavoring agent, diacetyl.

Toxicity resulting from exposure to radioactivity (expressed as oxidative DNA modification and protein oxidation) has been countered in part by NAC, which acts by virtue of buttressing GSH levels. Compounds of formula I, by directly substituting for GSH, may be more direct in their address of such toxicities. Similarly, respiratory distress syndromes caused by exposure to volatile electrophiles such as perfluoroisobutene that may occur either occupationally or recreationally due to accidental or planned pyrolysis of polytetrafluoroethene are countered by NAC. Compounds for formula I may be similarly useful.

Deficiency in general leukocyte (lymphocytic or nonspecific neutrophilic) responses in AIDS patients arises in part due to depleted GSH levels. NAC has been previously utilized to counter GSH deficiency. Compounds of formula I, by virtue of their ability to substitute for GSH, may be similarly useful.

Other ailments whose direct or indirect symptoms partly result from GSH depletion or from oxidating insult, such as clinical manifestations of influenza, cancer, heart-disease, Sjogren's syndrome and myoclonous epilepsy, may be ameliorated by treatment with compounds of formula I.

Oxidative insult due to pyrolysis products inhaled during the smoking of cigarette or other fumes causes inflammation of respiratory and oral mucosa. NAC has demonstrated efficacy in countering such harmful effects of smoking; therefore, compounds of formula I that act more directly than NAC may be expected to be useful in such situations.

Erdosteine and other thiols are useful as mucolytic agents due to their thiol functionality. GSH insufflations itself has been utilized to penetrate and reduce respiratory mucosal viscocity. Compounds of formula I have all of the structural characteristics of the aforementioned clinical agents, and therefore may be utile in such cases (Gregory S. Kelly, N. D., "Clinical application of N-acetylcysteine" Alternative Medicine Review, Volume 3, Issue 2, pages 114-127, 1998).

EXAMPLE 1

Evaluation of Ψ-GSH

The glutathione surrogate (Ψ-GSH) may substitute for GSH while possessing resistance to γ-GT mediated metabolism. The compound Ψ-GSH may be resistant to γ-GT by virtue of the substitution of the γ-glutamyl-cysteine amide with a urea isostere. A γ-GT-resistant glutathione analogue may in turn be expected to possess longer residence time in the cell, conferring upon the analog improved apparent potency over GSH for antioxidant activity. Successful substitution of GSH includes fulfillment of principal GSH abilities and functions. The following properties of GSH may be important properties for a viable GSH replacement 1) BBB penetration, e.g., via recognition by the active transport machinery for GSH; 2) ability to function as a GSH surrogate for the Glx-I mediated detoxification of MG into lactate; 3) ability to protect cells against direct oxidative insults (e.g., $H_2O_2$ and MG) and 4) ability to protect cells against exposure to Aβ.

The structure of Ψ-GSH is provided below.

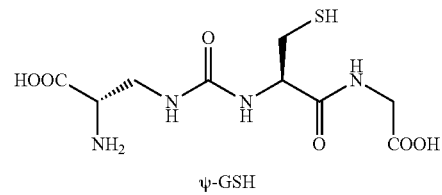 [SMILES: N[C@@H](CNC(=O)N[C@@H](CS)C(=O)NCC(=O)O)C(=O)O]

ψ-GSH

Ψ-GSH was synthesized from the previously reported protected peptide 1. (More et al., J. Med. Chem. 2008, 51, 4581-4588) The t-butyl carbamate and t-butyl ester protecting groups were removed concomitantly in TFA, followed by reductive removal of the S-StBu protecting group (Scheme 1). Ψ-GSH obtained after chromatography over C-18 bonded silica gel was found to be 96% pure by HPLC and its structure was intact according to $^1H$ and $^{13}C$ NMR spectra.

Scheme 1. Synthesis of Ψ-GSH

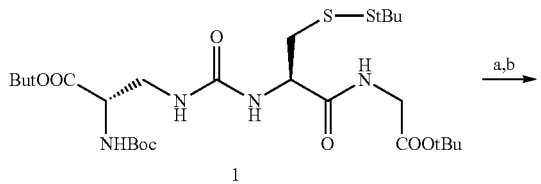

1

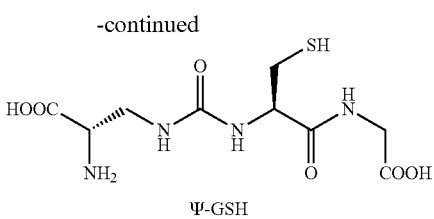

Ψ-GSH

Reagents and conditions: (a) TFA/CH$_2$Cl$_2$ (1:1), 91%; (i) Bu$_3$P, iPrOH/H$_2$O, 94%

No appreciable degradation of Ψ-GSH was observed during its incubation with γ-GT for up to 24 h, while GSH was completely degraded by γ-GT within 30 minutes. This was in accordance with observations with the properties of similar previously reported analogs and derivatives of Ψ-GSH. Formation of the γ-glutamyl cysteine amide bond is a rate-limiting step in the synthesis of GSH, a fact that compounds the GCL deficiency in aging and Alzheimer's disease afflicted tissue. Provision of a γ-glutamyl cysteine motif in such cases would address that important deficiency. Supplementation with γ-glutamyl cysteine has been found to yield an antioxidant effect and increase GSH levels. However, such a dipeptide does not address the problem of continual γ-GT mediated GSH metabolism. Ψ-GSH is rendered immune to such a drawback due to demonstrated resilience to γ-GT.

Glx-I was found to recognize Ψ-GSH and mediate its addition to MG to form hemimercaptal 2. The slopes for initial velocity vs. substrate concentration were 0.0498±0.0040 for Ψ-GSH and 0.1954±0.0216 for GSH (FIG. 1). In comparison, the corresponding slope the best known alternative cofactor for the Glx-I reaction, asparthione, had a value of 0.0132±0.0136. (Behrens, J Biol. Chem. 1941, 503-508) Ψ-GSH is thus not just a viable substrate for the Glx-I detoxification pathway; it is a better substrate than any other known alternative substrates. Its relatively slower rate of reaction when compared to GSH would be well-compensated by increased residence time of Ψ-GSH.

Scheme 2. Glx-I mediated formation of 2.

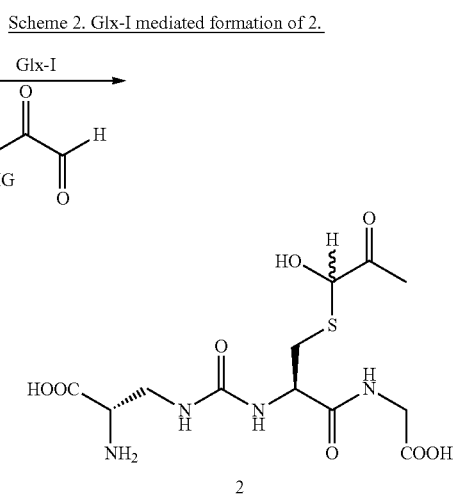

Figure 2:
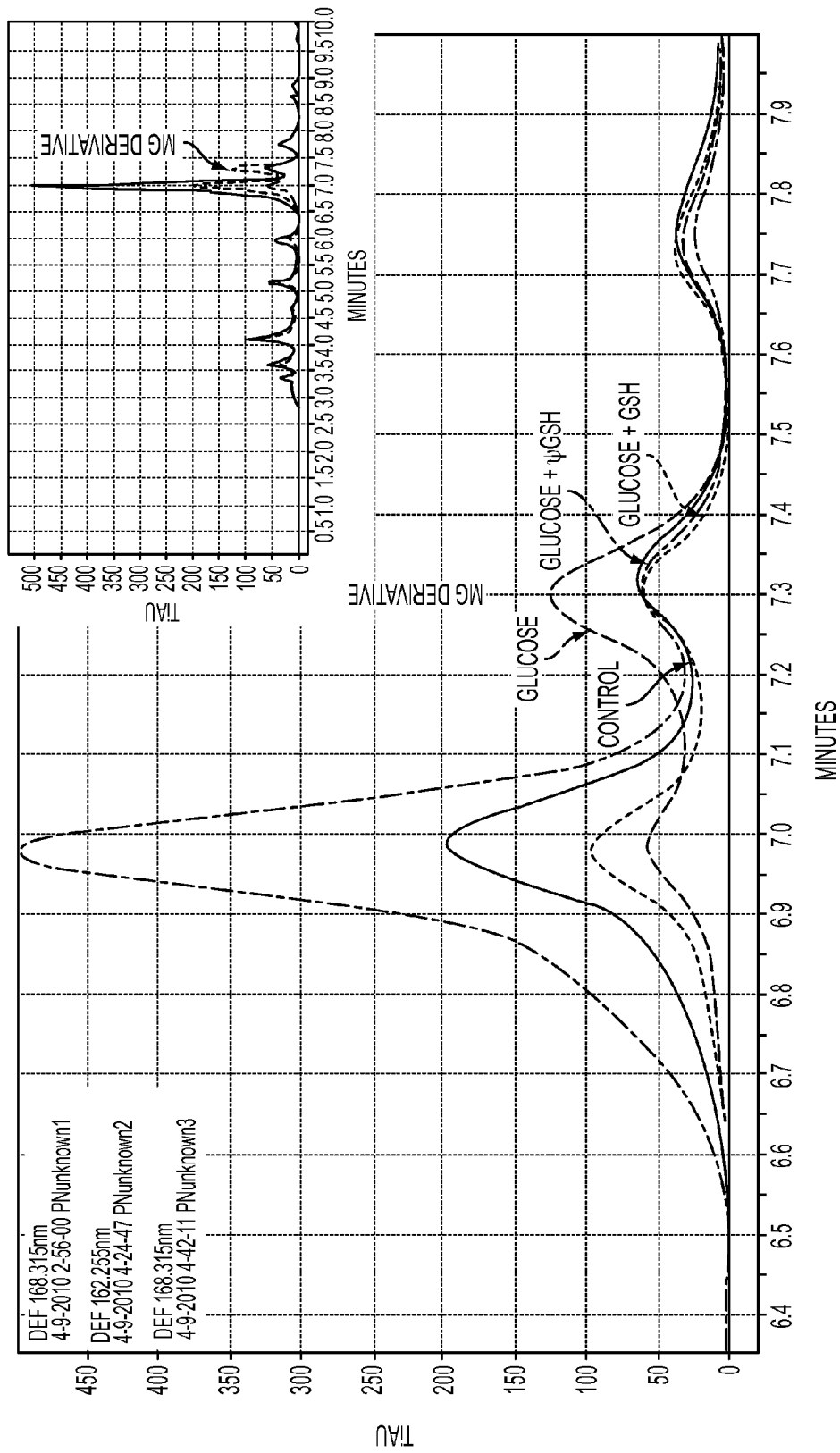
FIG. 2. Effect of GSH and ΨGSH on intracellular levels of methylglyoxal. SH-SY-5Y cells were treated with glucose (50 mM) for 72 h in the presence and absence of GSH or ΨGSH (500 μM). Intracellular concentrations of MG were quantified by HPLC after derivatization with 1,2-diaminobenzene as described in Materials and Methods. The results of this experiment demonstrated that GSH and ΨGSH caused reduction in MG levels to similar extents.

MG-scavenging activity of Ψ-GSH was next examined in a cell-based assay. A 2.1-fold increase in the production of MG in SH-SY-5Y cells over untreated controls could be induced by incubation with 50 mM of glucose for three days (FIG. 2). Pre-incubation of these cells either with GSH or Ψ-GSH before glucose exposure prevented glucose-induced intracellular MG accumulation. Importantly, Ψ-GSH inhibited MG accumulation to an extent comparable to that of GSH; perhaps stemming from its higher stability despite being a poorer substrate than GSH. Hyperglycemia-induced intracellular MG accumulation has shown to be involved in diabetes-related cellular damage; this is an area where Glx-I substrates such as Ψ-GSH could prove utile apart from its potential application in Alzheimer's disease. (Queisser et al., Diabetes 2009, 59, 670-678)

Figure 3:
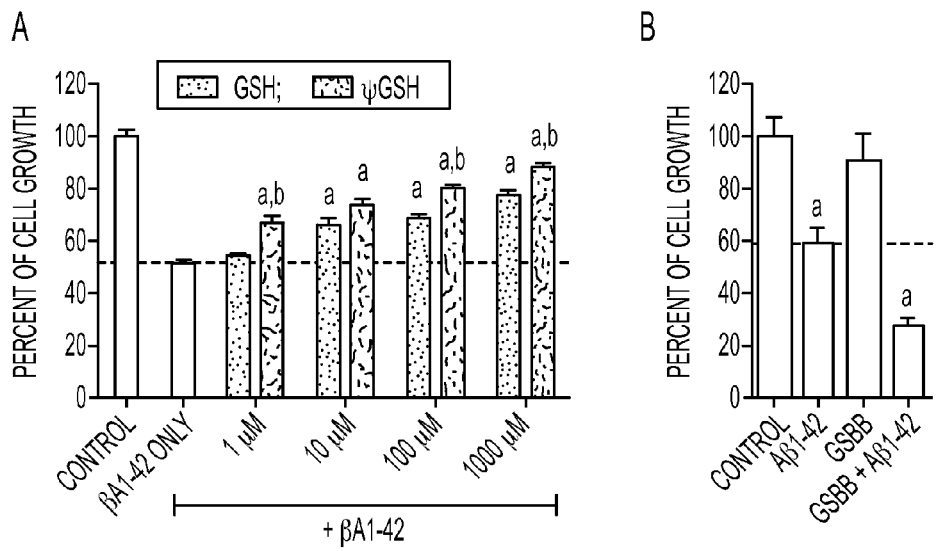
FIG. 3. Protection against Aβ 1-42 cytotoxicity by GSH and ΨGSH. The percent cell death caused in SH-SY-5Y cells by 24 h exposure to Aβ1-42 (20 μM) exposure was determined by the standard MTT assay as described in Materials and Methods. The decrease in cytotoxicity of Aβ1-42 was observed by pre-incubation of cells with (A) GSH or ΨGSH and (B) GSBB (1 mM) for 24 hours and was dose-dependent with respect to their concentrations. Data are expressed as the (mean±SEM) of three independent experiments (a, significantly higher than βA 1-42 only group, $p<0.0001$; b, significantly higher than corresponding GSH treatment group, $p<0.05$).

Aβ elicits its cytotoxicity at least in part through its ability to provoke intracellular ROS formation, as it has been shown that antioxidants can prevent Aβ-induced cell death in vitro. Treatment of SH-SY-5Y cells with 20 μM Aβ (1-42) caused significant (48.2%) loss of cell viability, evidenced through decrease in cell number and mitochondrial activity (FIG. 3A). Pretreatment of the cells with GSH or Ψ-GSH for 24 h caused dose-dependent resistance to Aβ toxicity. Concentrations of 10 μM of both compounds fully protected the cells, with the protection obtained with Ψ-GSH being significantly higher statistically ($p<0.05$) than that with GSH. Of particular note is the length of Ψ-GSH-induced cytoprotection that was five days, as opposed to that with GSH, which was significant only until day 3. The higher duration of protection conferred by Ψ-GSH could be due to its higher stability to γ-GSH mediated metabolism.

The mechanism of Aβ-induced cell damage may encompass any number and types of ROS. The significance of MG in the toxicity induced by Aβ was evaluated by preventing intracellular detoxification of MG through inhibition of Glx-I with an inhibitor, —S-p-bromobenzylglutathione (GSBB). (Vince et al., J. Med. Chem. 1971, 14, 402-404) Incubation of SH-SY-5Y cells with 1 mM GSBB caused 10% cell death. Percentage cell viability after treatment with Aβ alone and in combination with GSBB was 58.95 and 23.60, respectively (FIG. 3B; $p<0.0001$). It therefore appears that MG is an important ROS generator in Aβ induced cell damage.

Figure 4:
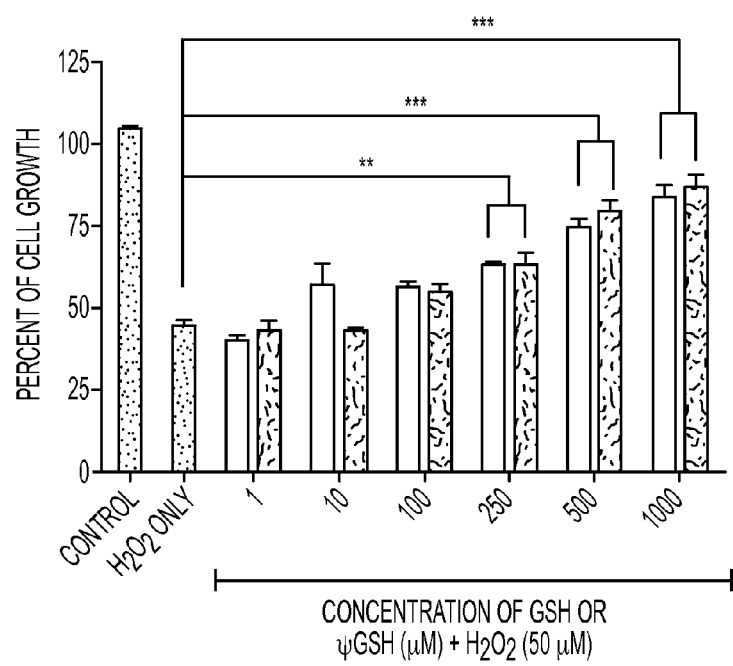
FIG. 4. Reduction in the cytotoxicity of $H_2O_2$ in the presence of GSH and ΨGSH. Pre-treatment of SH-SY-5Y cells with GSH or ΨGSH (1 mM) for 24 h prior to $H_2O_2$ (50 μM) exposure for 30 min showed a significant protection against peroxide toxicity. The protection observed due to GSH and ΨGSH was comparable and dose-dependent with respect to their concentrations. The data are expressed as the (mean±SEM) of three independent experiments ( $p<0.001$; * $p<0.0001$).
Figure 5:
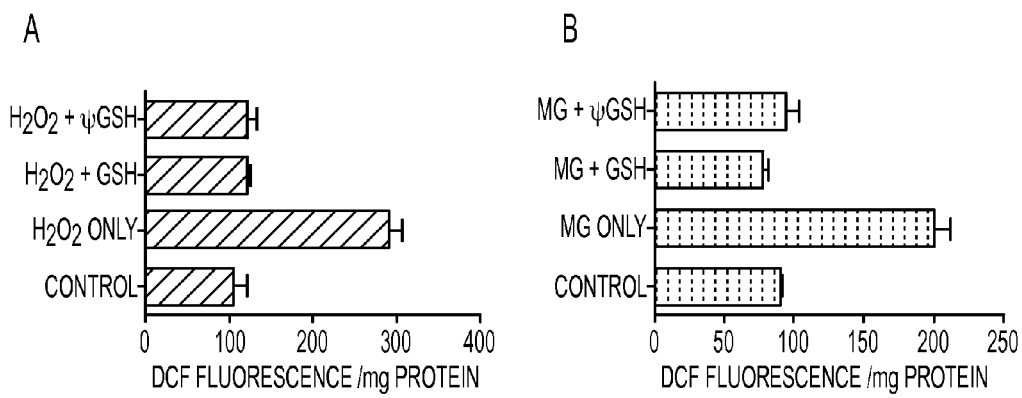
FIG. 5. Measurement of ROS using DCFH-DA. Oxidative stress was induced in SH-SY-5Y cells by exposure to (A) $H_2O_2$ (500 μM) for 90 min or (B) MG (1 mM) for 180 min at 37° C. in the presence or absence of GSH or ΨGSH (250 μM). Increase in fluorescence of DCF was regarded as an indicator of oxidative stress as described in Materials and Methods. Both GSH and ΨGSH were efficient at reducing the ROS generated by peroxide and MG. The data are represented as the (mean±SEM) of two independent experiments ($p<0.0001$).

One of the pathways through which Aβ causes intracellular ROS accumulation is through production of H$_2$O$_2$ in the presence of Cu(II). Damage caused by H$_2$O$_2$ contributes to the loss of synaptic function. GSH can directly neutralize H$_2$O$_2$ either through chemical reduction or by functioning as the sacrificial reductant in the GSHPx mediated reduction of H$_2$O$_2$. The ability of Ψ-GSH to protect cells against peroxide was next evaluated. A dose-dependent protection of SH-SY-5Y cells was obtained by preincubation with either GSH or Ψ-GSH before exposure to peroxide (FIG. 4). The activity of Ψ-GSH was comparable to that of GSH. Intracellular ROS concentration in response to H$_2$O$_2$ (500 μM) exposure was found to be 2.8-fold over control cells ($p<0.0001$). Co-incubation of H$_2$O$_2$ with GSH or Ψ-GSH (250 μM) led to reduction in ROS to the levels in control cells (FIG. 5A). Similar results were obtained with ROS generated by MG treatment (1 mM, 180 min; FIG. 5B), which was neutralized effectively by GSH or Ψ-GSH. These results demonstrate comparable antioxidant potency of ΨGSH to that of GSH.

Figure 6:
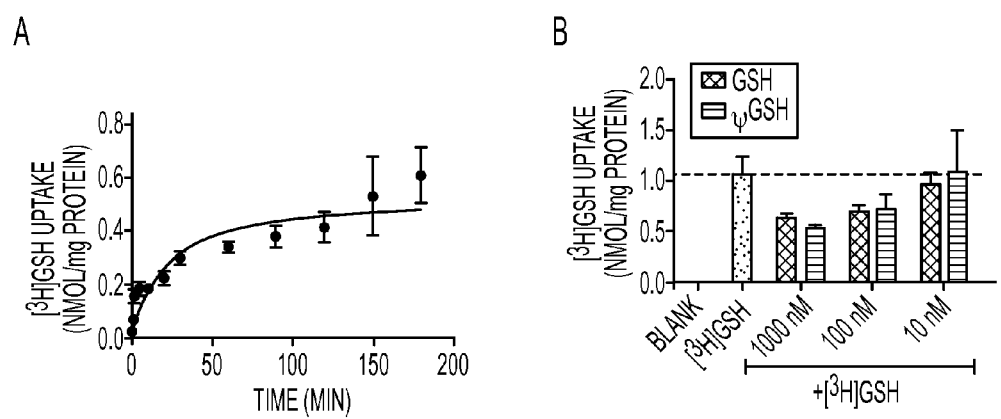
FIG. 6. (A) Uptake kinetics of [$^3$H]GSH in SH-SY-5Y cells. SH-SY-5Y cells were exposed to [$^3$H]GSH (100 nM) at 37° C. for various time intervals and intracellular radioactivity was measured using scintillation counter. The net uptake was normalized to protein content in each well as described in Materials and Methods. The data are represented as the (mean±SEM) of three independent experiments. (B) Inhibition of [$^3$H]GSH uptake by ΨGSH. Uptake of [$^3$H]GSH (1000 nM) in the presence and absence of GSH and ΨGSH (10, 100 and 1000 nM) was determined in SH-SY-5Y cells as described in Materials and Methods. The inhibition of [$^3$H] GSH uptake by ΨGSH was comparable to that by cold GSH. The data are represented as the (mean±SEM) of three independent experiments ($p<0.0001$).

The ability of Ψ-GSH to traverse the blood brain barrier (BBB), which has active transport machinery for GSH was examined. GSH uptake transporters are located on the luminal side and display broad substrate specificity. The uptake of [$^3$H]-GSH by SH-SY-5Y cells at a concentration of 100 nM of [$^3$H]-GSH was determined in the presence of 1 μM, 100 nM and 10 nM of Ψ-GSH (FIG. 6). GSH uptake was found to be inhibited in a dose-dependent manner by Ψ-GSH, the magnitude of which was comparable with that obtained in the presence of similar concentrations of cold GSH. This ascertains that the membrane transport mechanism for GSH is capable of recognizing Ψ-GSH.

The studies in this report support the hypothesis of a metabolically stable GSH analog being a viable GSH replacement. Ψ-GSH is recognized by the GSH transporter in the BBB. Ψ-GSH is successfully utilized by the cellular machinery that detoxifies MG, a major component of oxidative stress in Alzheimers' disease. In that regard, Ψ-GSH is a better substrate than all known alternative substrates for Glx-I, making it a valuable enzymological tool. It possesses the ability of GSH to counteract AO-induced intracellular ROS. As anticipated, Ψ-GSH is stable to γ-GT making its use as an antioxidant potentially more practical than GSH or glutamylcysteine. This stability to γ-GT enables it to protect cells against AO-induced toxicity for a significantly longer period when compared to GSH.

Drugs and Reagents. Radiolabeled [$^3$H]-GSH was purchased from Perkin Elmer Life Sciences (Waltham, Mass., USA). All other chemicals were purchased from Sigma (St. Louis, Mo., USA). Yeast glyoxalase I was purchased from Sigma. Aβ1-42 was purchased from American Peptide Company (Sunnyvale, Calif., USA). For all experiments, Aβ1-42 was dissolved in 100% 1,1,1,3,3,3-hexafluoro-2-propanol (HFIP) to a concentration of 1 mg/mL, sonicated in a water bath for 10 min and dried under vacuum. The HFIP-treated Aβ1-42 was dissolved in dimethylsulfoxide (DMSO) to a final concentration of 1 mM and stored at −20° C. Asparthione and S-(p-bromobenzyl)-glutathione were synthesized using a combination of previously published methods. (More et al., J. Med. Chem. 2009, 52, 4650-4656; Pileblad et al., Biochem. Pharmacol. 1992, 44, 895-903). The cell culture media MEM, F12, and fetal bovine serum (FBS) were obtained from Invitrogen (Carlsbad, Calif.).

General Synthetic Procedures. All commercial chemicals were used as supplied unless otherwise indicated. Dry solvents (THF, Et$_2$O, CH$_2$Cl$_2$ and DMF) were dispensed under argon from an anhydrous solvent system with two columns packed with neutral alumina or molecular sieves. Flash chromatography was performed with Silica-P flash silica gel (silicycle, 230-400 mesh) with indicated mobile phase. All reactions were performed under inert atmosphere of ultra-pure argon with oven-dried glassware. $^1$H and $^{13}$C NMR spectra were recorded on a Varian 300 MHz spectrometer. High resolution mass data were acquired on a Bruker Bio TOF-II spectrometer capable of positive and negative ion ESI source, using PPG or PEG as internal standards.

Synthesis of ΨGSH. To the tripeptide 1 (700 mg, 1.15 mmol) was added with stirring a mixture of CH$_2$Cl$_2$, TFA and anisole in a ratio of 2:2:1. The flask was flushed with argon and stirring was continued at ambient temperature for 3 h. The progress of the reaction was monitored by LC-MS. Upon consumption of starting material, the reaction mixture was concentrated to dryness and the residue was triturated with ether. The white precipitate (Ψ-GSH-S-StBu) was filtered, washed with ether and utilized in the following step without further purification.

A solution of Ψ-GSH-S-StBu (0.40 g, 1.01 mmol) in 15 mL of nPrOH:H$_2$O (2:1) was adjusted to pH=8.5 with 25% aq ammonia. nBu$_3$P (400 µL, 1.51 mmol) was then added and the reaction mixture was allowed to stir at ambient temperature for 2 h. The reaction mixture was then evaporated to dryness and the residue triturated with CHCl$_3$ (3×30 mL) to afford a clear oil. This oil was loaded on a column (15 g) of C-18 bound silica gel and the column was eluted with water. Relevant fractions were evaporated to dryness to obtain an oil that was triturated with methanol to afford Ψ-GSH as a white solid (180 mg, 58%). Mp 165-167° C.; $R_f$=0.50 (Butanol/Acetic acid/Water; 4:1.5:2); $[α]_D^{20}$ −16.1 (c 0.54, 1N HCl); $^1$H NMR (300 MHz, D$_2$O) δ ppm 4.60 (q, J=4.8, 8.4 Hz, 1H, α-CH:Cys), 4.48 (q, J=4.8, 7.8 Hz, 1H, α-CH:Dap), 4.17 (m, 2H, CH$_2$:Gly), 3.68-3.62, 3.41-3.34 (2 m, 2H, β-CH$_2$:Dap), 3.24-2.98 (m, 2H, β-CH$_2$:Cys); $^{13}$C NMR (75 MHz, CD$_3$OD-CF$_3$COOD)δ174.5, 172.6, 170.5, 159.2 (C=O), 52.4 (α-C: Cys), 49.1 (α-C: Dap), 44.3 (β-C:Dap), 42.6 (CH$_2$:Gly), 31.5 (β-C:Cys); ESI-HRMS m/z 309.0798 (M+H)$^+$; C$_9$H$_{16}$N$_4$O$_6$S+H$^+$ requires 309.0869; Reverse phase HPLC was run on Varian Microsorb column (C18, 5 µm, 4.6×250 mm) using two solvent systems with 0.5 mL/min flow rate and detected at 220 nm. Solvent system 1: 0.04 M TEAB (triethylammonium bicarbonate) in water/70% acetonitrile in water=1/1, $t_R$=7.70 min, purity=96.06%. Solvent system 2: 0.04 M TEAB in water/70% acetonitrile in water=20–100% B linear, $t_R$=13.67 min, purity=95.90%.

Cell Culture. The human neuroblastoma cell line, SH-SY-5Y was obtained from American Type Culture Collection (Manassas, Va.). The cells were maintained in MEM:F12 (1:1) medium supplemented with 10% FBS, 100 units/mL penicillin and 100 units/mL streptomycin and 1% NEAA (non-essential amino acid). Cells were grown at 37° C. in a humidified atmosphere with 5% CO2/95% air.

Glyoxalase I Enzyme Kinetics Assay. The glutathione analog, Ψ-GSH and asparthione were examined for their ability to act as substrates for the yeast glyoxalase I mediated reduction of MG. The commercial 40% methylglyoxal solution was distilled to remove polymerization products. Enzyme assays were performed (30° C., 0.05 M phosphate buffer (pH 6.6)) using a thermostated Beckman DU® 7400 spectrophotometer. Fresh solutions of GSH, Ψ-GSH and asparthione were prepared on the day of the assays with distilled, deionized water. In each assay, the cell contained a total volume of 3.0 mL which was no more than 6.0 mM with respect to methylglyoxal and 1.3 mM with respect to GSH or its analogs. Sufficient amounts of glyoxalase I, in the presence of 0.1% bovine serum albumin as a stabilizing agent, were employed so as to afford an easily measurable initial rate that was followed by an increase in absorption at 240 nm. MG, GSH or its analogs and buffer were added to a cuvette and allowed to stand for 6 min in the thermostated compartment of the spectrophotometer to allow complete equilibration of the substrates with the hemimercaptal 2. Hemimercaptal substrate concentrations were calculated from the concentrations of thiol peptide and methylglyoxal added, using a value of $3.1×10^{-3}$ M for the dissociation constant of the hemimercaptal at pH=6.6. Data were analyzed utilizing an Enzyme kinetics module of Sigmaplot 9.0 from Systat Software Inc.

γ-Glutamyltranspeptidase Assay. The stability of γ-GSH towards γ-GT mediated degradation was determined by incubating 100 µL of 10 mM solutions of GSH or Ψ-GSH (dissolved in 200 mM of 2-amino-2-methyl-1,3-propanediol buffer at pH 8.5) with 10 µL of 0.54 mg/100 µL of equine kidney γ-glutamyltranspeptidase in the above buffer in presence of 20 µL of acceptor dipeptide gly-gly (40 mM in the above buffer). After incubation for 1 hour at 37° C., compound from each tube was spotted on a silica gel TLC plate. The plates were developed alongside authentic predicted degradation products with the solvent system: 4:1.5:2; Butanol/Acetic acid/Water. Visual detection of TLC spots was performed under UV and also by iodine and fluorescamine staining solution.

Inhibition of Glutathione Uptake by Ψ-GS. The uptake experiment was performed under conditions described previously. Briefly, the cells were seeded in 24-well plates. After an overnight incubation, the cells were treated with 100 nM concentration of [$^3$H]-GSH in uptake buffer (128 mM NaCl, 4.73 mM KCl, 1.25 mM CaCl$_2$, 1.25 mM MgSO$_4$, and 5 mM HEPES, pH =7.4) in the presence or absence of Ψ-GSH at concentrations of 10, 100 and 1000 nM at 37° C. under 5% $CO_2$ for 30 min. At the end of incubation, the cellular uptake was terminated by washing three times with ice-cold PBS. Any remaining buffer was aspirated, and the cells were lysed with 1 ml of warm 0.1% SDS/0.1 N NaOH solution for a minimum of 45 min. Intracellular levels of radioactive GSH were determined using liquid scintillation counting. All resulting levels of GSH uptake were normalized to the total protein in each well using a BCA protein assay. All uptake experiments were performed in triplicate and statistically significant differences in uptake were evaluated using Graphpad Prism 5.1 (Graphpad, La Jolla, Calif.) using a one-way ANOVA followed by a Dunnett's post hoc test with a false discovery rate of 0.05.

Cytotoxicity Studies: Protection against β-amyloid 1-42 cytotoxicity in SH-SY-5Y cells was measured by standard MTT assays. SH-SY-5Y cells were seeded in 96-well plates at the density of 30,000 cells/well. After overnight incubation, the cells were exposed to GSH or Ψ-GSH at a concentration of 1 mM for 24 h at 37° C. After 24 h of incubation, the drug-containing medium was replaced with media containing 20 μM β-amyloid 1-42 peptide and the incubation was allowed to continue for additional 24 hours after the addition of the drugs. At the end of the incubation, 20 μL of MTT stock solution (5 mg/mL) was added to each well and incubated for 3 h at 37° C. The MTT reaction medium was discarded and the purple-blue MTT formazan crystals were dissolved by the addition of 100 μL of 0.1 N HCl in isopropanol. The optical density (OD), a reflection mitochondrial function of the viable cells, was read directly with a microplate reader (BioTek SynergyHT, VT, USA) at 580 nm and a reference wavelength of 680 nm. Concentration response graphs were generated for each drug using GraphPad Prism software (GraphPad Software, Inc., San Diego, Calif., USA). Results are expressed as mean percent inhibition of β-amyloid toxicity with the standard error of the mean. In another set of experiments, cells were preincubated with a glyoxalase I inhibitor, S-(p-bromobenzylglutathione) (1 mM) for 24 hours before addition of βamyloid1-42 peptide (20 μM).

Similar procedures were used for determining the protective effect of GSH and its analog against $H_2O_2$ cytotoxicity. After preincubation of cells with GSH or Ψ-GSH for 24 hours, cells were exposed to $H_2O_2$ (50 μM) for 30 min and the media was replaced with fresh media. Cells were incubated for an additional 24 h after which the cell viability was determined by the MTT assay as described earlier.

$H_2O_2$ and MG-Induced Cellular Oxidative Stress. SH-SY-5Y cells were cultured in 96-well black plates at the density of 10,000 cells/well and were allowed to reach confluence (~48 h). The cells were then treated with a solution of 2,7-dichlorofluorescin diacetate (DCFH-DA, 20 μM) in RPMI 1640 medium without FBS for 45 min. Extracellular DCFH-DA was removed by washing twice with PBS. To induce oxidative stress, the cells were treated with hydrogen peroxide (500 μM) or methylglyoxal (1 mM) in RPMI media without FBS in presence and absence of GSH or Ψ-GSH (250 μM) for 90 min or 180 min at 37° C. in the dark. The cells were washed with PBS and then lysed by adding 250 μl of 90% DMSO/10% PBS for 10 min in the dark at room temperature with shaking. The fluorescence intensity in each well was measured in the fluorescence plate reader (BioTek SynergyHT, VT, USA) at an excitation of 485 nm and an emission of 538 nm and normalized to the protein content in each well as determined by the BCA assay. (Wang et al., Free Radic. Res. 2008, 42, 435-441)

Determination of Intracellular MG Concentration. SHSY5Y cells were seeded in a T150 flask and allowed to grow for 24 h. The next day, cells were treated with glucose (50 mM) in the presence and the absence of GSH or Ψ-GSH (500 μM). Cells without glucose treatment were used as a control. After 3 days of treatment, the cell pellet was collected and sonicated in 1 mL of PBS buffer to obtain cell lysates, which were derivatized as follows: 1 mL of cell lysate+0.2 mL 5 M $HClO_4$+0.2 mL 10 mM 1,2 diaminobenzene+0.1 mL 1 μM 5-methylquinoxaline (internal std.)+0.5 mL water to 2 mL final volume. Samples were incubated at room temperature overnight and then centrifuged. The supernatant was passed through a C-18 SPE cartridge which had been prepared by flushing 2-4 mL of acetonitrile followed by 2-4 mL of 10 mM $KH_2PO_4$ (pH 2.4). After evaporation of the acetonitrile layer, the solid obtained was redissolved in 0.2 mL of 20% acetonitrile in 10 mM $KH_2PO_4$ (pH=2.4). The concentration of MG derivative, 2-methylquinoxaline, was measured using a Beckman Coulter Gold chromatography system. The column was Varian Microsorb-MV 300-5 25 cm C18 column (4.6 mm internal diameter and 5 μm particle diameter). The mobile phase was 80 vol % of 10 mM $KH_2PO_4$ and 20 vol % of HPLC grade acetonitrile. The analysis conditions were as follows: detector wavelength, 315 nm; mobile phase flow rate, 1.0 mL/min; typical injection volume, 20 μL). Duplicate injections of each sample were made. Samples were calibrated by comparison with a 2-methylquinoxaline standard. The average retention time of 2-methylquinoxaline was 7.35 min.

Data Analysis: Data were analyzed statistically by unpaired or paired Student t tests, as appropriate. Statistical significance was set at p<0.05.

EXAMPLE 2

Evaluation of Ψ-GSH

Short-term toxicity of Ψ-GSH was assessed by administration of Ψ-GSH i.p. 3×/week for two weeks with 2000 mg/Kg being the highest dose. Body weights and CBC were insignificantly affected. Unaffected ALT, AST, ALP, blood urea nitrogen (BUN) and creatinine levels suggest unaffected hepatic or renal function. Histopathology of lung, liver and kidney tissue reflected no significant difference between the Ψ-GSH treated and saline-treated mice.

Figure 7:
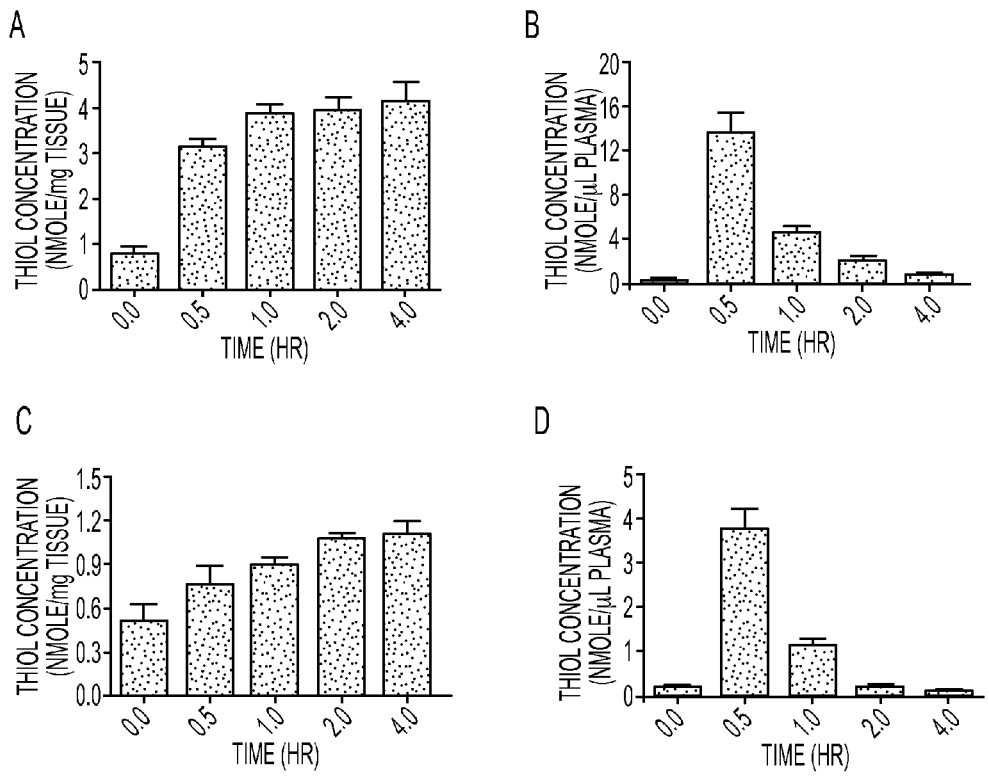
FIG. 7. Measurement of brain thiol concentration. Temporal dependence of the thiol concentrations in the brain and plasma of C57BL/6 mice following intraperitoneal (A and B) and oral (C and D) administration of 500 mg/Kg Ψ-GSH. Data is expressed as the mean±SEM, * p $<0.0001$, n=4. Plasma thiols reached maxima within 30 min of Ψ-GSH injection while brain concentrations plateaued within 2-4 hours.

The ability of Ψ-GSH to elevate brain thiol would reflect the former's ability to traverse the BBB (FIG. 7). Although the toxicity study suggested tolerance for far higher doses, it was decided to administer 500 mg/Kg i.p. since it was the minimum dose and route that caused reproducible and statistically significant changes in plasma and brain thiol levels. A single i.p. administration of Ψ-GSH (500 mg/Kg) elevated total plasma thiol 46-fold, from 0.29±0.05 nmol/μL to 13.55±0.73 nmol/μL within 30 minutes (FIG. 7B). This decreased to 15 fold over basal concentration within one hour and dropped to basal levels at 4 hours. Brain thiol levels, however, elevated 5-fold from 0.78±0.06 nmol/mg of tissue to 4.16±0.16 nmol/mg of tissue over two hours. This level was sustained until the experiment was discontinued at 4 hours (FIG. 7A). Oral administration of Ψ-GSH (500 mg/Kg) elevated plasma thiol levels from 0.21±0.05 nmol/pt to 3.68±0.480 nmol/μL over 30 minutes and reducing to basal levels over 2 hours (FIG. 7D). Corresponding brain thiol levels plateaued at 2.1-fold higher (1.10±0.04 nmol/mg of tissue) than basal levels (0.51±0.05 nmol/mg of tissue) at the 4-hour time point (FIG. 7C). Clearly, elevation of brain thiol levels caused by either i.p. or oral administration of Ψ-GSH is sustained for a duration far longer than that in plasma.

Figure 8:
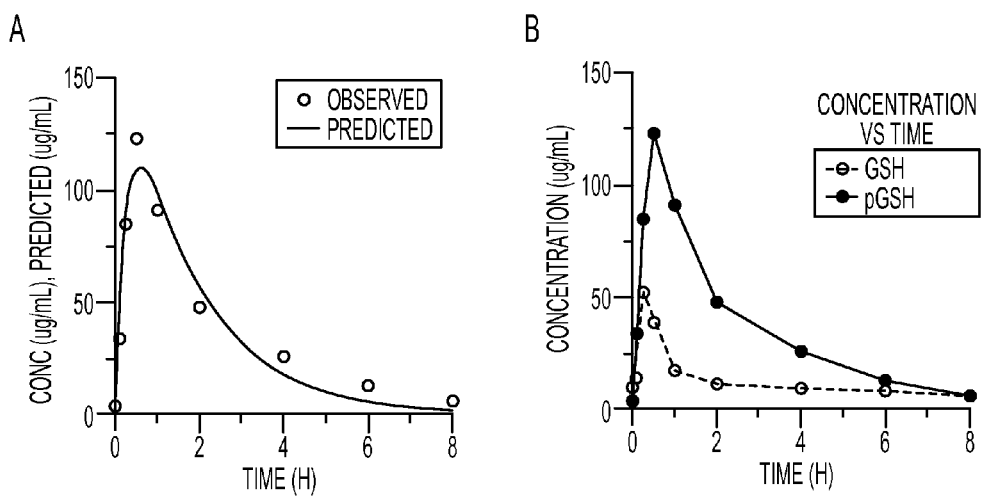
FIG. 8. (A) Non-linear pharmacokinetic estimation of Ψ-GSH (n=4 per time point). The observed (○) and predicted (−) plasma concentrations are plotted as a function of time for Ψ-GSH. Data were best fit by the initial one-compartment open model with first order absorption and elimination. (B) Concentrations of Ψ-GSH (closed circles) and GSH (open circles) in plasma after a single i.p. dose of 500 mg/kg. Each time point represents the mean of four animals.

In-vivo fates of Ψ-GSH and GSH were compared by administration to wild-type C57BL/6 mice followed by plasma sampling and DTNB-derivatization of samples before HPLC analysis. Following the peak in plasma levels upon administration, plasma concentrations of both declined in a logarithmically linear fashion. The plasma concentration-time curve fitted a one-compartment model with first-order absorption and elimination (FIG. 8). The Cmax of Ψ-GSH (109.7 µg/mL) was 2.5-fold higher than that of GSH (43.94 µg/mL), while its corresponding Tmax value (0.566 h) was 3-fold higher than that of GSH (0.336 h). Ψ-GSH was eliminated considerably slower (elimination half-life, $t_{1/2}$=1.227 h) than GSH ($t_{1/2}$=0.495 h). Combined with a lower $t_{1/2}$, the higher Cmax for Ψ-GSH resulted in a 5.3-fold higher AUC (267.4 h·µg/mL) when compared to GSH (50.22 h·µg/mL) (Table 1).

TABLE 1

Estimated pharmacokinetic parameters for Ψ-GSH and GSH

| PK Parameter | Ψ-GSH | GSH |
|---|---|---|
| Cmax (µg/mL) | 109.7 | 43.94 |
| Tmax (h) | 0.566 | 0.336 |
| AUC (h · µg/mL) | 267.4 | 50.22 |
| K01 absorption half life (h) | 0.171 | 0.127 |
| K10 elimination half life (h) | 1.227 | 0.495 |
| CL_F Clearance (mL/h/Kg) | 1869 | 9955 |

Figure 9:
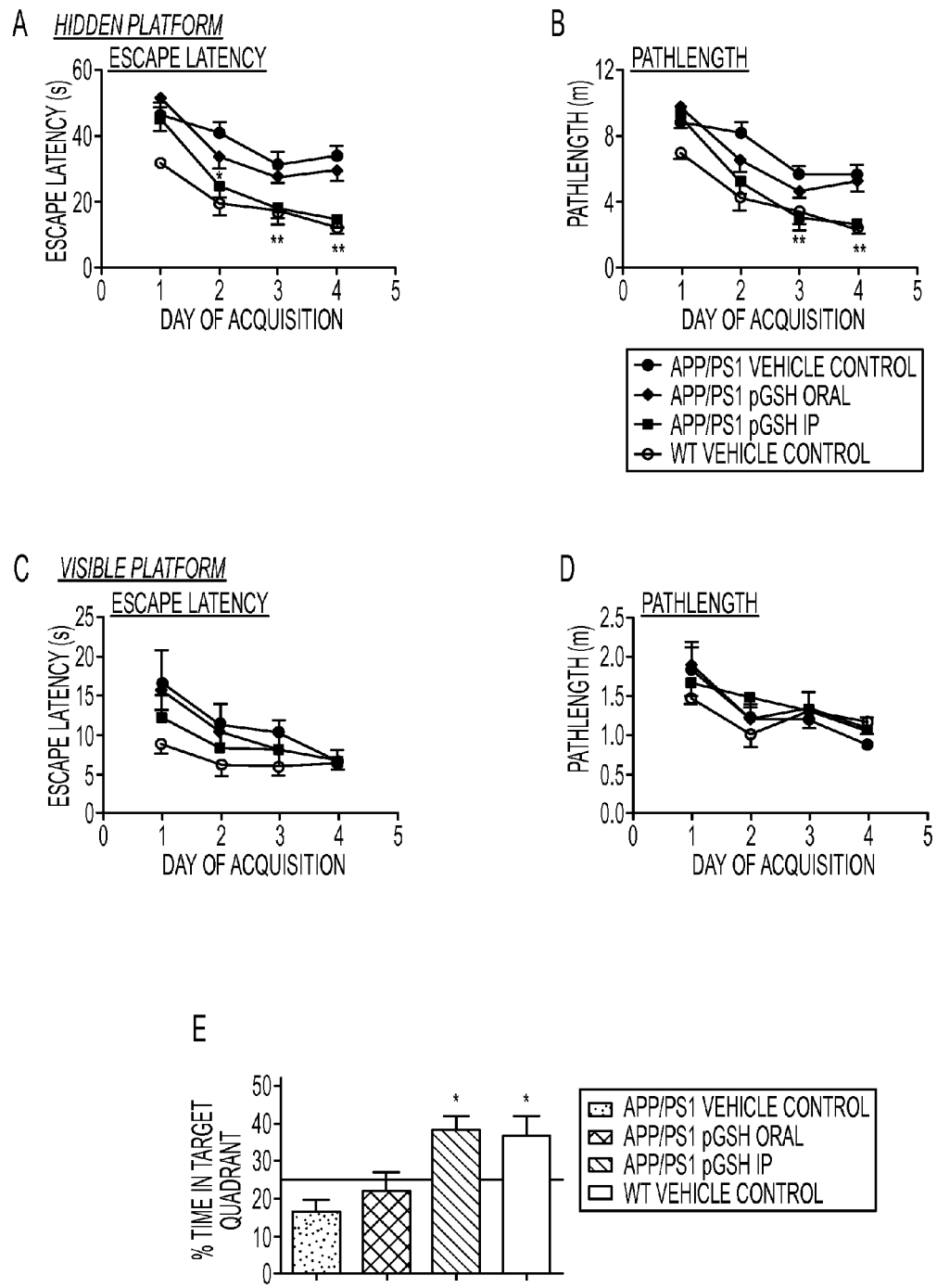
FIG. 9. Effect of Ψ-GSH administration on spatial reference memory in a Morris water maze. (A and B) Performance during acquisition was expressed as the mean (±SEM) latency and pathlength to locate a submerged platform from APP/PS1 saline, APP/PS1 Ψ-GSH i.p., APP/PS1 Ψ-GSH p.o., non-transgenic wild type (WT) saline groups, during four consecutive days of training (4 trials per day). (C and D) Results of visible platform trials executed at the end of hidden platform training and the probe trial are represented as escape latency and pathlength as well. Mice treated with Ψ-GSH exhibited an enhancement in memory when compared to corresponding saline controls. Retention of memory tested in the probe trial (E) 24 h after the hidden platform training, showed a greater bias of Ψ-GSH treated mice to spend time in the area previously containing the platform (* p<0.05; ** p<0.001; compared with APP/PS1 saline group).

The transgenic mouse model (APP-PS1) employed in this study expresses human APPswe and PS1-ΔE9 and develops elevated $Aβ^{1-42}$ levels at the age of 4 months with manifest plaque deposition a month hence (Trinchese et al., Ann. Neurol. 55, 801-814 (2004)). Ψ-GSH (500 mg/Kg i.p.) was administered to 3-month old APP-PS female mice 3×/week for 12 consecutive weeks. Non-transgenic, WT C57BL/6 mice were employed as negative controls. At 11 weeks of Ψ-GSH treatment, all groups were evaluated in the "Morris water maze" learning evaluation technique (FIG. 9). Mice treated i.p. with Ψ-GSH showed significant learned behavior inculcation during the first week of testing, while untreated transgenic mice did not (FIG. 9A). On days 3 and 4 of the training, escape latencies for mice treated with Ψ-GSH (day 3: 17.91±4.65 s; day 4: 14.64±2.61 s) were similar to those for WT saline-treated mice (day 3: 17.29±2.13 s; day 4: 12.42±2.18 s). The escape latency values for the i.p. Ψ-GSH treated APP-PS1 mice and those for saline-treated APP-PS1 mice were also significantly different (one-way ANOVA, p<0.001). Path lengths traversed by the Ψ-GSH treated APP-PS1 mice correlated well with corresponding escape latencies (FIG. 9B), thus, on the last day of training, shorter path lengths were traversed by APP-PS1 mice treated with Ψ-GSH (2.69±0.47 m) than saline-treated APP-PS1 mice (5.76±0.63 m). In fact, Ψ-GSH treated APP-PS1 mice traversed paths of lengths similar to saline-treated WT mice. Contributions of motor function improvement to these abilities were excluded as swim-speeds were similar across the groups.

Learned tasks retention and acquired memory were evaluated by a single probe trial 24 h following conclusion of training (FIG. 9E). APP-PS1 mice spent only 16.39±3.39% of the time in the target quadrant, while the APP-PS1 (i.p. Ψ-GSH) and non-transgenic vehicle controls retained significantly greater memory, spending 38.43±3.73% and 36.67±5.30%, respectively, in the target quadrant. The APP-PS1 mice treated with Ψ-GSH also entered the target quadrant with significantly higher frequency than did the untreated APP-PS1 mice. When the platform was rendered visible again (FIG. 9C), the escape latencies of all the treatment groups were similar at the end of four trials (APP/PS1/saline: APP/PS1/Ψ-GSH i.p: WT/saline, 6.64±1.58, 6.75±1.49, 6.53±0.75 s). Path lengths (FIG. 9D) and swimming speeds across various groups also were similar, indicating no effect of transgene with regard to reference memory.

Figure 10:
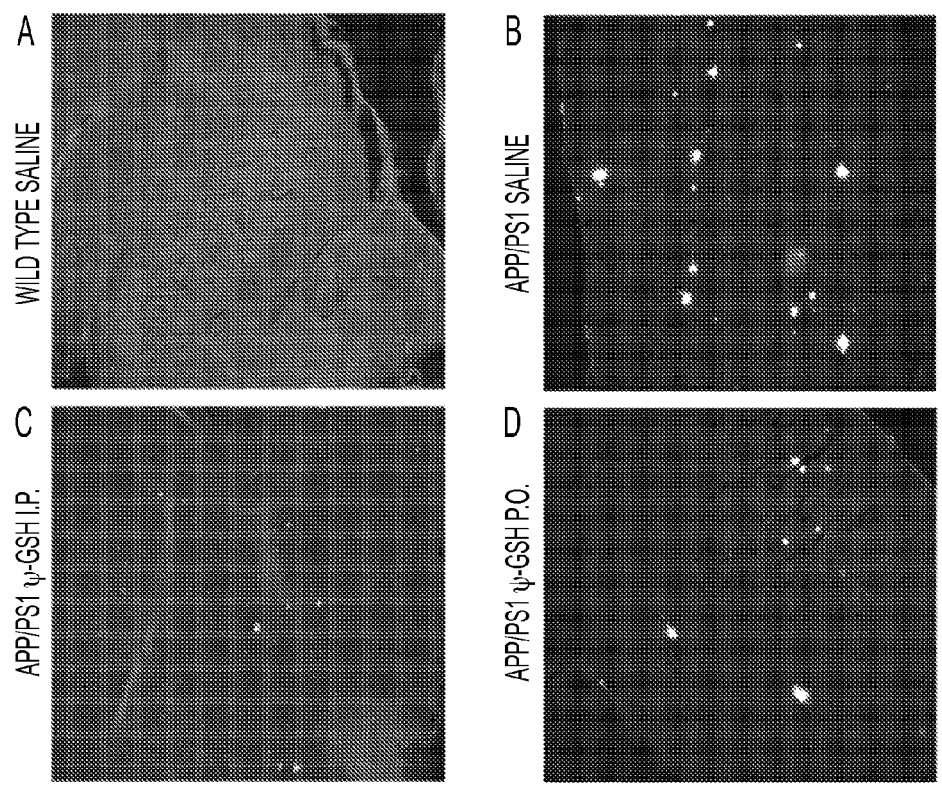
FIG. 10. Immunohistochemical detection of Aβ$^{1-42}$ in the mouse brain treated with Ψ-GSH. Magnification 10×. (A) wild type saline control; (B) APP/PS1 saline; (C) APP/PS1 Ψ-GSH i.p.; (D) APP/PS1 Ψ-GSH p.o. Amyloid plaques are observed as intensely yellow stained regions in sagital sections of brain. Mice treated with intraperitoneal Ψ-GSH showed dramatic reduction in size and number of plaques.
Figure 11:
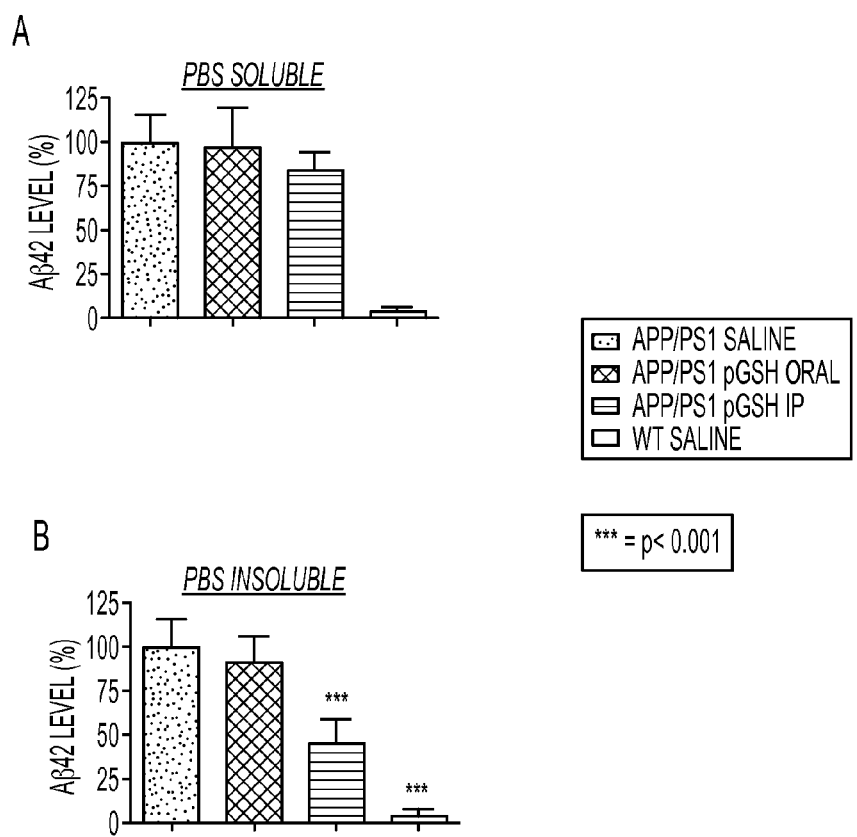
FIG. 11. Quantitation of the effect of Ψ-GSH treatment on amyloid load in APP/PS1 mice. Aβ$^{1-42}$ levels in the brain homogenate of mice treated with saline or Ψ-GSH (i.p. or p.o.) for twelve weeks were measured by ELISA as described in Materials and Methods. (A) PBS-soluble Aβ$^{1-42}$ levels were not different within treatments groups. (B) There was a significant reduction in PBS-insoluble (guanidine-soluble) Aβ$^{1-42}$ in the brains of APP/PS1 mice treated with intraperitoneal Ψ-GSH (*** p<0.0001) when compared to saline-treated controls. However, the difference did not reach statistical significance in oral Ψ-GSH treated mice.

Excised brain tissue was examined for AD pathology indicators. Aβ plaque deposits were estimated by immunostaining brain sections with Aβ-antibody (FIG. 10). Brain tissue sections of i.p. Ψ-GSH treated APP/PS1 mice had significantly lower Aβ load than the corresponding untreated mice. The number and size of Aβ plaques was drastically reduced in the Ψ-GSH treated group. $Aβ^{1-42}$-specific ELISA revealed PBS and guanidine-soluble Aβ levels in the brain homogenates (FIG. 11). Brain tissue of APP/PS1 mice treated i.p. with Ψ-GSH showed robust decrease in insoluble $Aβ^{1-42}$ (45.4±6.01% of vehicle-treated APP/PS1 mice; p<0.0001; FIG. 11A). Differences between levels of PBS-soluble Aβ were statistically insignificant across APP/PS1 mice groups (FIG. 11B).

Figure 12:
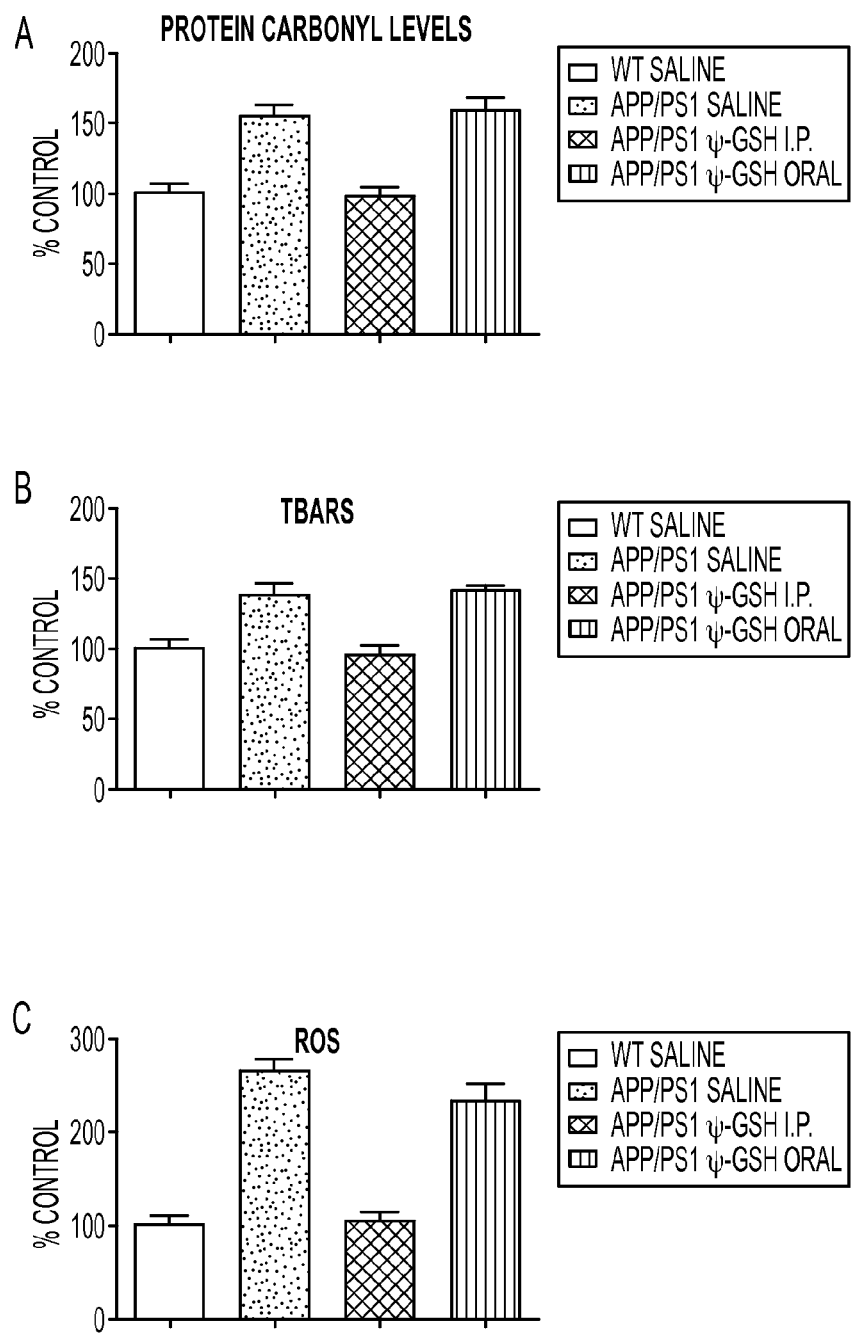
FIG. 12. Increased oxidative stress in the brains of APP/PS1 mice was decimated by Ψ-GSH treatment. Protein carbonyls (A), thiobarbituric acid reactive substances (TBARS), and ROS were measured as markers of oxidative stress as described in Materials and Methods. Results are shown as a percentage increase over levels of each oxidative marker in the brains of the non-transgenic (wild type) saline treated controls. Statistical significance was assessed by one-way ANOVA ( p<0.001, * p<0.0001 compared with APP/PS1 saline treated mice).
Figure 13:
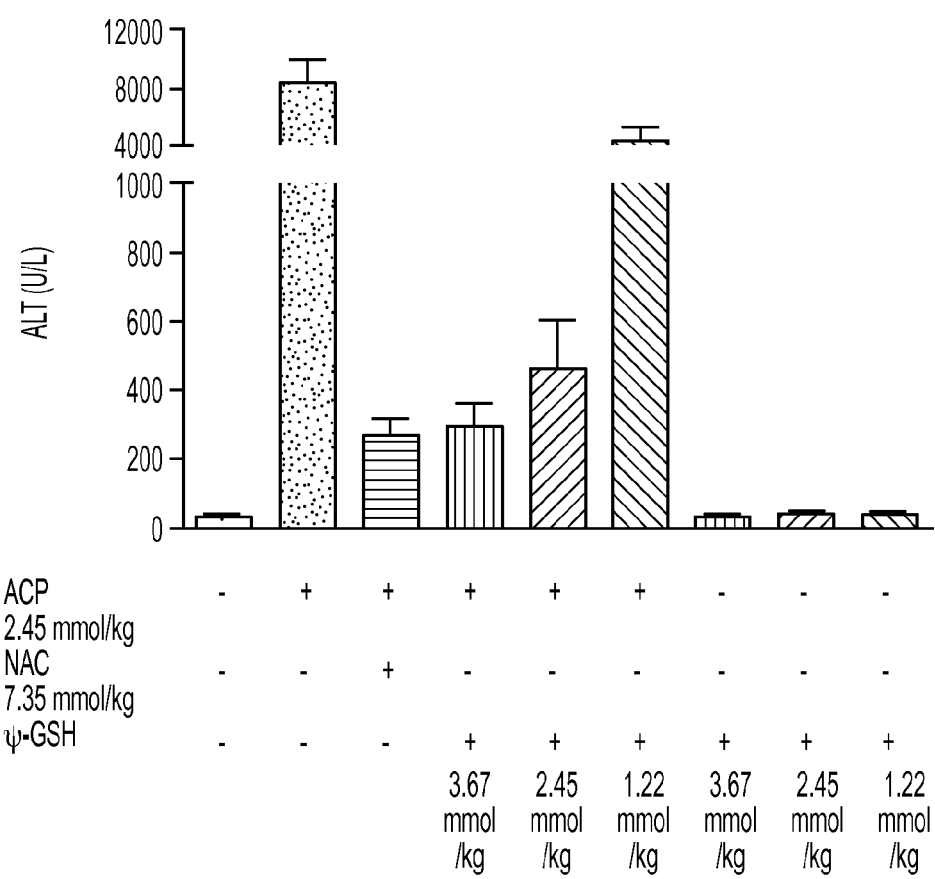
FIG. 13. Comparing Ψ-GSH and N-Acetylcysteine for ACP overdose rescue ability and evaluating the effects of Ψ-GSH on normal liver.

Levels of protein carbonyls, products of lipid peroxidation and raw ROS are hallmarks of incipient Aβ pathogenesis. FIGS. 12A and 12B show the protein carbonyl levels and the extent of lipid peroxidation Ψ-GSH treated and untreated APP/PS1 mice brains. The same were also measured in age-matched saline treated WT mice as controls and were considered 100%. Protein carbonyls (detected as 2,4-dinitrophenylhydrazones) were elevated significantly in untreated APP/PS1 mice (154±8.49%; p<0.0001) in relation to WT mice. Intraperitoneal Ψ-GSH treated APP/PS1 mice, however, had levels comparable to WT mice (97.8±6.30%; p>0.05; FIG. 12A). Estimation of thiobarbituric acid reactive substance (TBARS) provides an empirical measure of the extent of lipid peroxidation, particularly that of the production of the peroxidation end-product, malondialdehyde (FIG. 12B). APP/PS1 mice treated with saline had significantly elevated (137±9.58%; p<0.001) levels of TBARS when compared to WT controls. Treatment with Ψ-GSH i.p. reduced TBARS levels in APP/PS1 mice to extents comparable to WT mice (95.3±5.51%; p>0.05). Consistent with protein carbonylation and lipid oxidation levels, total brain ROS levels were also found to be elevated in APP/PS1 mice (266±11.78%; p<0.0001) when compared to WT mice (FIG. 12C). I.p. Ψ-GSH treatment lowered these levels to a statistically insignificant 6% (p>0.05) increase.

APP/PS1 mice were also treated orally with Ψ-GSH 3×/week for 3 months. Trends toward higher spatial memory development and lower escape latencies were noted relative to the saline-treated group, with the trends reaching significance (one-way ANOVA, p<0.05) on day 2, but diminishing in the following days. Path lengths traversed by APP-PS1 mice treated orally with Ψ-GSH and the saline-treated controls were insignificantly different and this correlated with recorded escape latencies. In the probe trial, orally treated APP/PS1 mice spent 21.76±5.36% in the target quadrant; similar to saline treated transgenic controls. Brains of orally treated APP/PS1 mice showed a modest decrease in Aβ plaques relative to controls, which correlated with its effect on insoluble $Aβ^{1-42}$ concentration (90.80±6.72% of vehicle treated APP/PS1 mice; p>0.05). The levels of protein carbonylation, lipid peroxidation and/or ROS were unaffected by oral Ψ-GSH in APP/PS1 mice.

The ability of a glutathione mimic, Ψ-GSH, of restoring spatial mnemonic function in a transgenic Alzheimer's mouse model is described herein. Immunohistochemical and biochemical assays indicate that Ψ-GSH acts, at least in part, due to reduction in brain oxidative stress that translates into lowered amyloid load.

Currently utilized antioxidants are relatively non-toxic, attributable to their being dietary nutrients or derivatives. The ureide linkage between the β-diaminopropanoic acid and the cysteinyl components of Ψ-GSH create a non-dietary component fragment. The safety of Ψ-GSH upon short-term administration in the present mouse model at a strikingly high dose of 2000 mg/Kg, with no apparent nephro-, hepato- or hematotoxicity is therefore encouraging, particularly for an entity being developed for chronic administration.

The in-vivo significance of the Ψ-GGT-resistant ureide isostere contained in Ψ-GSH is apparent from comparison of its pharmacokinetic profile with GSH, in particular, its 5.3-fold greater plasma retention. The ability of Ψ-GSH to permeate the blood-brain barrier has also been examined through utilization of the active-transport mechanism for GSH in in-vitro cell-monolayer experiments. The present finding that Ψ-GSH administration causes sustained elevation of brain thiol suggests that the aforementioned transport mechanism is of relevance in the intact animal.

Mild cognitive impairment (MCI) that precedes early AD (eAD) reflects synapse loss in the dentate gyrus of the hippocampal formation, with cognitive descent (expressed as lower spatial mnemonic and cued recall abilities) becoming tractable. The "Morris water maze" tool is a widely accepted modality for isolation of cognitive decline of hippocampal origin from unrelated behavioral impairment. In the hidden platform version of the Morris water-maze, increasing ability of a mouse to locate this platform and thereby "escape" the water during the training period indicates spatial memory acquisition. Specifically, lowering in the "escape latency," i.e., the time required for a mouse to locate the platform reflects the degree of place-cell development in the hippocampus and the firing of neurons of the postsubiculum to afford momentary directional heading. These regions of the hippocampal formation are known to be primary foci of AD, and thus, it is expected that hippocampal lesion would increase escape latency. The transgenic mouse model employed in this study (APP/PS1) develops elevated $A\beta^{1-42}$ levels, an harbinger of possible neuronal damage, at the age of 4 months. I.P. Ψ-GSH treatment in these mice appeared to foster spatial reference mnemonic capabilities similar to wild-type mice. The APP/PS1 mice treated i.p. with Ψ-GSH attained escape latencies as low as WT mice. The i.p. Ψ-GSH treated APP/PS1 mice, like the WT mice were clearly biased toward locating into the quadrant of the water-maze where the platform was previously placed. No such spatial bias or improved capabilities were recorded for the untreated APP/PS1 mice. Lower escape latencies could result also from higher motor function or higher visual acuity, both abilities being unrelated to hippocampus derived spatial-cognition. Similar swim-speeds across the groups exclude this possibility.

Histopathology lends biochemical and microscopical basis for the neuron-sparing effects of Ψ-GSH. The i.p. Ψ-GSH treated mice exhibited far lower insoluble Aβ loads. Insoluble AO plaques are the ultimate result of preponderant β-sheet conformation in Aβ populations, presence of Aβ-derived AGEs and their interactions with other glyco- and lipoproteins in the cytoplasm, the CSF or the IST. Ψ-GSH thus seems to have countered AGE-initiated or derived pathological processes. In contrast to Aβ plaques, PBS-soluble Aβ loads over all the groups of mice were not significantly different. Soluble unaggregated $A\beta^{1-42}$ is not toxic on its own accord, and higher levels of soluble $A\beta^{1-42}$ are expected in the APP/PS1 mouse due to the transgene. $A\beta^{1-42}$ aggregation orders are indeterminate through the ELISA utilized in this study. Behavioral results, however, allude to reduction of $A\beta^{1-42}$ aggregation to toxic soluble oligomers. Ψ-GSH is not designed to affect the formation of soluble Aβ, rather, it is designed to inhibit the misfolding/aggregation of A. Unaffected soluble Aβ levels are thence expected.

Protein carbonylation produces AGEs that foster further free-radical formation, particularly in the case of $A\beta^{1-42}$, where the carbonyl-modified products are more prone to amyloidogenesis. Excised brain tissue from untreated APP/PS1 mice showed elevated levels of protein carbonyls relative to age-matched WT mice. I.P. Ψ-GSH nullified this relative increase, lending credence to the premise that Ψ-GSH acts upstream in the oxidative damage process by culling early originators of free-radical formation. Lipid peroxidation is particularly concerning as it induces τ-hyperphosphorylation, furthering tauopathy, the second etiologic component of AD. Higher degrees of lipid peroxidation noted in APP/PS1 mice were reduced to WT control mice levels by i.p. Ψ-GSH. The concentrations of total ROS in APP/PS1 mice were found to be alarmingly elevated in this study. Ψ-GSH i.p. was able to abrogate these increases as well. The capability of Ψ-GSH to act on upstream, e.g., on the originators of ROS, is well-reflected in its ability to influence final ROS levels.

The present study has made apparent that the replacement the γ-glutamylcysteine linkage with a γ-GGT stable ureide isostere confers upon the resultant molecule unique properties that hold relevance in the intact animal. While thiol augmentation in the brain has been a long-sought goal, Ψ-GSH is the first known molecule that is specifically designed and now proven in these in-vivo studies to address all of the known catabolic and biosynthetic problems of GSH metabolism that exist in the degenerative environment created by AD pathogenesis. Ψ-GSH thus satisfies all of the pharmacodynamic and toxicologic criteria that need fulfillment in order for a molecule to be advanced into further drug-development.

Drugs and Reagents. All the chemicals including glutathione used in this study were obtained from Sigma (St. Louis, Mo.), unless stated otherwise. Ψ-GSH was synthesized using previously published synthetic method. Purity of Ψ-GSH was confirmed with elemental analysis upon combustion as well as through chromatographic separation on a HPLC and was found to be >96% pure. Amyloid-13 antibody (Cat. #2454) used for immunohistochemistry was obtained from Cell Signaling Technology International (Beverly, Mass.). DyLight® 594 conjugated donkey anti-Rabbit IgG H&L (Cat #ab96921, Abcam, Cambridge, Mass.) was used as a secondary antibody.

Animals. The C57BL/6 wild type and APP/PS1 double transgenic Alzheimer's mice (APPswe/PS1ΔE9) were used in the present study. The mice were acquired from the Jackson Laboratory (Bar Harbor, Me.) at the age of six to ten weeks. All experimental procedures and animal handling were executed in accordance with the national ethics guidelines, approved and complied with all protocol requirements at the University of Minnesota, Minneapolis, Minn. (IACUC). For all experiments, animals were housed 3 per cage, in a controlled environment (temperature 22° C., humidity 50-60%, and light from 07:00-19:00); food and water were available ad libitum.

Detection of Non-Protein Thiols in Plasma and Brain. Wild type C57BL/6 mice at the age of six to eight weeks (4 per group) were treated with Ψ-GSH i.p and orally. Mice were euthanized by overdose of ketamine and xylazine at the desired time-points from the administration of the drug (0, 0.5, 1, 2 and 4 hours after drug administration). Brain and plasma samples were collected. Brains were perfused with ice-cold 0.9% NaCl, and cut sagittally into left and right hemispheres. The right hemisphere was fixed in Zamboni's fixative as described under Immunohistochemistry. The left hemispehere was immediately frozen in liquid nitrogen and utilized in further biochemical analysis. Brain tissue was homogenized in ice-cold buffer (50 mM phosphate, pH 7.0, containing 1 mM EDTA containing protease inhibitors) containing 5% sulfosalicylic acid. After homogenization, samples were centrifuged at 8000×g for 10 min at 4° C. The clear supernatant was transferred to a new tube and used for analysis of free thiol concentration.

Blood was collected in heparin-coated tubes (Fisher, Pittsburgh, Pa.) and immediately centrifuged at 5000×g for 10 min at 4° C. The top plasma layer was transferred into a new tube and mixed with an equal volume of 5% sulfosalicylic acid in 50 mM potassium phosphate buffer containing 1 mM EDTA disodium salt (pH 7.5). This was followed by centrifugation of samples at 8000×g for 10 min at 4° C. and analysis of thiol concentration.

For analysis of thiol, DTNB (5,5'-dithio-bis-2-nitrobenzoic acid, Ellman's reagent) was used which liberated a yellow colored 5-thio-2-nitrobenzoic acid (TNB) upon reaction with thiol. The rate of TNB production is directly proportional to the concentration of free thiols in the sample. Total thiol concentration which was normalized to the weight of tissue or μL of plasma employed.

Assay Conditions: 150 μl of Tris.HCl, pH 8.9 (Trizma base, 0.2 M; EDTA 0.02 M)+20 μl of DTNB (1 mg/mL in methanol)+50 μl of supernatant from TCA precipitation. The changes in absorbance were measured at 412 nm after 10 mM incubation in dark at room temperature.

Dose Determination Study: Ψ-GSH was injected intraperitoneally and orally in wild type C57BL/6 mice (6-8 week old, 4/group) three times a week for two weeks. The doses of Ψ-GSH employed ranged from 100 mg/kg to 2000 mg/kg. Body weight (twice a week), complete blood count (CBC) analysis and liver, kidney and lung histology was considered to be indicative of toxicity from the drug treatment. Histological sections of tissue were analyzed by a board-certified pathologist at the Masonic Cancer Center-Comparative Pathology Shared Resource, University of Minnesota.

Pharmacokinetic Evaluation of Ψ-GSH. Eight weeks old C57BL/6 female mice (n=4 animals/time point) were given 500 mg/kg of GSH or Ψ-GSH in saline intraperitoneally. Blood samples were collected at 0, 5, 15, 30 mM, 1, 2, 4, 8, 24 hr after the drug administration through retro-orbital bleeding into heparin-coated tubes. Blood was immediately centrifuged at 5000×g for 10 min at 4° C. The top plasma layer was transferred into a new tube and mixed with an equal volume of 5% sulfosalicylic acid in 50 M potassium phosphate buffer containing 1 mM EDTA disodium salt (pH 7.2). This was followed by centrifugation of samples at 8000×g for 10 min at 4° C. and analysis of thiol concentration. The derivatization reaction was realized utilizing 130 μL of the supernatant, 500 μL of Tris-HCl buffer 0.5 M, pH 8.9 and 350 μL of DTNB 10 mM in of $K_2HPO_4$ (0.5 M, pH 8.0). After 5 min in an ice bath, the reaction mixture was acidified by addition of 100 μL $H_3PO_4$ 7 M and centrifuged at 3000×g for 10 min. Then, derivatized GSH or Ψ-GSH was filtered through a 0.22 μm membrane and 20 μL was injected in HPLC at 330 nm. HPLC analysis was carried out on a Beckman Coulter Gold HPLC system, controlled by a system controller (32 Karat workstation with PC). The HPLC conditions employed a Varian Microsorb column (C18, 5 μm, 4.6×250 mm) using solvent A [water containing 0.9% v/v formic acid] and solvent B [acetonitrile] with 1 mL/min flow rate and detected at 330 nm.

Solvent B was increased from 0 to 30% in 9 min, then to 80% in 7 min, and held at 80% for an additional 4 min. The retention time for derivatized Ψ-GSH was 11.8 minutes.

Efficacy Study Design. To determine the effect of intraperitoneal and oral Ψ-GSH treatment, the study was divided in four groups (10 mice/group). 1. APP/PS1 mice-vehicle control, 2. APP/PS1 mice-Ψ-GSH i.p. 500 mg/kg, 3. APP/PS1 mice-Ψ-GSH oral 500 mg/kg, 4. Non-transgenic wild type mice-vehicle control. All the animals in the above-said groups were treated with saline or Ψ-GSH three times a week for 12 weeks, starting at the age of three to four months. Eleven weeks after the start of the treatment, the animals were tested in the Morris water maze, and twelve weeks after the start of the treatment, the animals were sacrificed for histopathological analysis.

Behavior Study. Eleven weeks after the beginning of the treatment, the animals were tested for one week in an open field water maze. The maze consists of a white circular tank (120 cm diameter) of water (23±1° C.) rendered opaque with nontoxic crayola paint. The mice were placed in the water at the edge of the pool and allowed to swim in order to locate a hidden, but fixed escape platform, using extra-maze cues.

On Day 1, the mice were be placed in the pool and allowed to swim freely for 60 s. If an animal could not locate the hidden platform within that time, it was placed manually upon the platform and left there for 10 s. Each animal was tested in four trials per day. The inter-trial interval was 15 min. Each start position was used equally in a pseudorandom order, and the animals were always placed in the water facing the wall. The platform was placed in the middle of northeast quadrant of the pool (approximately 30 cm from the side of the pool). The mouse's task throughout the experiment was to find and climb onto the platform, escaping the water. Once the mouse learned the task (Day 4, Trial 16), a probe trial was conducted 24 hours after the last trial of acquisition on Day 4.

In the probe trial (i.e., Trial 17, day 5), the platform was removed from the pool and animals were allowed to swim for 60 s. Their ability to remember the location of the previously present escape platform was quantified in proportion to the residence time of the mouse in the quadrant previously containing the platform. Immediately following the probe trial, visible platform was reintroduced at a different location (i.e southeast quadrant) along with a visible flag. Mice were trained to locate this cued platform in 4 trials conducted in the aforementioned manner.

Immunohistochemistry. Mice were anesthetized, and their brains were removed, cut sagittaly. Following post-fixation of right hemisphere in Zamboni's fixative (4% paraformaldehyde and 15% picric acid in 0.25 M sodium phosphate, pH 7.5) for 48 h before being cryopreserved in a 30% (wt/vol) sucrose in phosphate-buffered saline solution. Brains were then were embedded in O.C.T. Tissue Tek Compound (Miles Scientific) and were cryosectioned at 10 μm thickness for immunohistochemistry, mounted on Superfrost™ microscope slides (Erie Scientific, Portsmouth N.H.) and stored at 20° C. until their utilization.

The brain sections were stained with a primary antibody against 0-amyloid peptide (Cell signaling, Cat. #2454) at a dilution of 1:200 in PBS. After an overnight incubation at 4° C., the sections were rinsed thrice for 10 min with PBS and then incubated for 2 h in donkey anti-rabbit IgG conjugated to Cy3 diluted to 1:1000 in PBS. The sections were rinsed in PBS thrice for 10 min, and stained with a nuclear stain DAPI before being dehydrated in graded ethanol series, and mounted in DPX prior to being coverslipped. Slides treated with the same technique but without incubation with the primary antibody were used as negative controls. Slides were observed under an Olympus microscope with confocal immunofluorescence.

Amyloid-β1-42 ELISA. Total $A\beta^{1-42}$ in the brain was quantified by sandwich ELISA (Invitrogen, Carlsbad, Calif.) according to the manufacturer's instructions. Wild type and transgenic Alzheimer's mice brains were Dounce homogenized in phosphate buffered saline (PBS), pH 7.2, containing a mixture of protease inhibitors. Brain homogenates were centrifuged and supernatants were assayed for soluble $A\beta^{1-42}$ per manufacturers' protocols. The pellets were suspended in guanidine buffer (5.0 M guanidine-HCl/50 mM Tris-HCl, pH 8.0) to dissolve all intra- and extracellular aggregates, incubated for 3 hr at room temperature, diluted with 1× Dulbecco's phosphate-buffered saline containing 5% BSA and protease inhibitors to reduce the concentration of guanidine-HCl to 0.5 M and centrifuged at 16,000×g for 20 min at 4° C. Supernatants were loaded into well-established commercially available anti-Aβ42 sandwich ELISA plates (Biosource International) and processed according to the manufacturer's instructions (Invitrogen). The concentration of both PBS soluble and insoluble (guanidine soluble) $A\beta^{1-42}$ was calculated from a standard curve of human $A\beta^{1-42}$ and was normalized to the weight of the tissue employed.

Protein Carbonyl Determination. Brains were homogenized in cold buffer (50 mM phosphate, pH 7.0, containing 1 mM EDTA containing protease inhibitors) and centrifuged at 10,000×g for 15 min at 4° C. The supernantent was mixed with 0.5 ml of 10 mM 2,4-dinitrophenylhydrazine (DNPH)/2 M HCL (or 2 M HCl alone for blanks). Samples were placed in a sample holder and incubated in the dark at room temperature for one hour vortexing intermittently. After incubation, proteins were precipitated with 0.5 mL of 20% TCA, centrifuged at 10,000×g for 10 min at 4° C. The pellet was washed with 1 mL of ethanol-ethyl acetate (1:1; v/v) to remove free DNPH reagent, and allowed to stand for 10 min on ice. The sample was centrifuged for 10 min at 10,000×g and the supernatant was discarded. The washing procedure was repeated two times for a total of three washes. The resulting protein pellet was resuspended in 6 M guanidine HCl. The samples were incubated at 37° C. for 15-30 min to aid dissolution of the protein. All samples were then centrifuged to remove any insoluble material remaining in suspension. The concentration of DNPH was determined at its maximum wavelength (360 nm) and the molar absorption coefficient of $22,000 \text{ M}^{-1} \text{ cm}^{-1}$ was used to quantify the levels of protein carbonyls. Total protein concentration was determined by BCA protein assay kit (Pierce, Rockford, Ill.). Protein carbonyl content was normalized to protein content and expressed as percent increase over saline treated transgenic mice.

Lipid Peroxidation Assay. The levels of lipid peroxidation were quantified by the thiobarbituric acid-reactive substances (TBARS) assay. Brain homogenate was treated with 2 ml of (1:1:1) ratio (TBA) thiobarbituric acid -(TCA) trichloroacetic acid -(HCl) chloridic acid reagent (TBA 0.37%, 0.25 N HCL and 15% TCA) and placed in water bath for 15 min, cooled and centrifuged and then clear supernatant was measured at 535 nm against reference blank. Protein was determined by the BCA protein assay kit. TBARS were normalized to the protein content in each sample and then expressed as percentage of the corresponding values in non-transgenic saline controls.

ROS Assay. ROS levels were quantified via the 2'-7'-dichlorofluorescein-diacetate (DCFH-DA) assay. The brain tissue was homogenized in 50 mM phosphate buffer containing 1 mM EDTA (pH 7.2) and centrifuged at 10,000 g for 15 min to sediment insoluble materials. DCFH-DA was then added to a portion of the homogenate to a final concentration of 100 μM and the reaction mixture was incubated for 30 min at 37 C. The reaction was then stopped by placing it on ice and the formation of oxidized fluorescent 2'-7'-dichlorofluorescein (DCF) was measured with a fluorescence plate reader (BioTek SynergyHT, VT, USA) using excitation and emission wavelengths at 488 and 525 nm, respectively. The final results were corrected for protein concentration and then expressed as percentage of the corresponding values in saline treated wild-type mice. All steps were performed in the dark and DCF formation was also monitored immediately after DCFH-DA was added to the homogenate (t=0 min) in order to subtract background autofluorescence.

EXAMPLE 3

Comparing Ψ-GSH and N-Acetylcysteine for ACP (Acetaminophen) Overdose Rescue Ability and Evaluating the Effects of Ψ-GSH on Normal Liver 36-Male Swiss Webster Mice (HSD) were fasted overnight and then brought to the lab at 8:00 am the following day and weighed. Food was kept out of the cages until after the final drug injection. Mice were divided into treatment groups as below in Table 2.

TABLE 2

| Treatment | Number of Mice |
| --- | --- |
| ACP + Ψ-GSH (3 doses) | 12 |
| ACP + NAC | 4 |
| Ψ-GSH only (3 doses) | 12 |
| ACP only | 4 |
| Saline | 4 |

Thirty minutes post overdose with 370 mg/kg ACP, the following were evaluated for the groups in Table 2:

N-acetylcysteine (NAC) at 7.35 mmol/kg;

Ψ-GSH at three different doses, 3.67, 2.45 and 1.22 mmol/kg; and examine effects of Ψ-GSH on normal liver at rescue doses.

Results were as follows:

ACP+Ψ-GSH; this compound, at the half molar equivalent of NAC produced decrease in ALT levels comparable to that caused by NAC;

Ψ-GSH given alone at the half molar equiv. of NAC and at lower doses was found to be safe and well tolerated in mice;

histopathological reports show absence of necrotic tissue in the liver of mice treated with ACP+Ψ-GSH, while ACP-only mice exhibited necrotic liver tissue; and ACP+NAC resulted in the death of half of the animals (50%) in the group.

The ability of Ψ-GSH to protect against ACP toxicity is supplemented by its relative lack of toxicity when compared to the currently utilized clinical rescue agent, NAC. While NAC rescue was found to be dose-limited, thereby introducing the risk of a rescue-agent overdose, Ψ-GSH would not carry this risk. Second, Ψ-GSH is found here to confer protection or rescue against ACP overdose/hepatotoxicity at substantially lower dosings. Since an ACP overdose rescue agent would be expected to be administered i.v., due to likely lack of consciousness on the victim's part, Ψ-GSH's lower dose and lack of a toxicity ceiling makes its administration far less susceptible to a clinical technician's errors.

EXAMPLE 4

Synthesis of Compounds 7, 8 and of Ψ-GSH

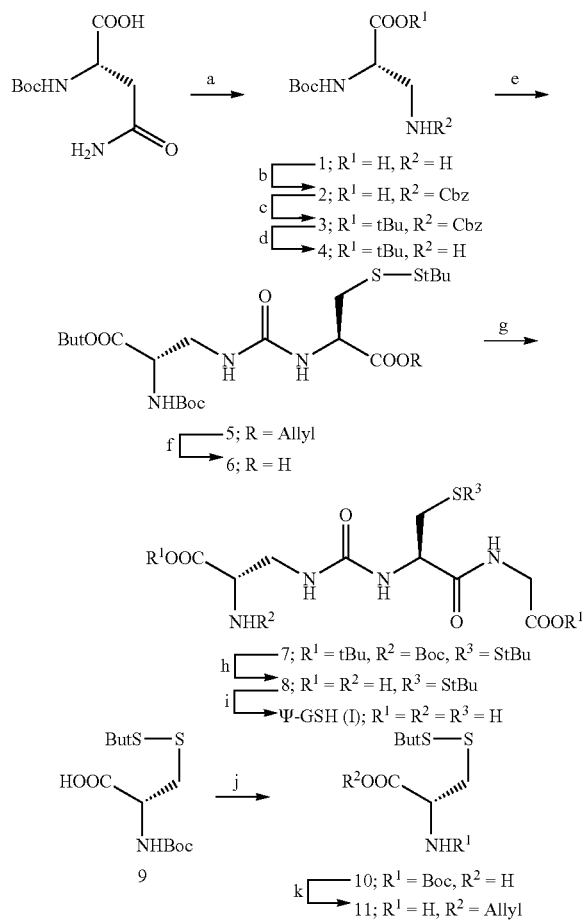

Reagents and conditions:
(a) PIDA, EtOAc/CH₃CN/H₂O (2:2:1), 62%;
(b) CbzCl, KOH, K₂CO₃, THF/H₂O (3:1), 94%;
(c) tBuOH, DCC, DMAP, CH₂Cl₂, 84%;
(d) H₂, 10% Pd/C, CH₃OH, 94%;
(e) 11, CDI, NMM, CH₂Cl₂, 67%;
(f) (PPh₃)₄Pd, morpholine, CH₂Cl₂, 80%;
(g) HCl·GlyOtBu, EDC, HOBt, NMM, CH₂Cl₂, 8%;
(h) THF/CH₂Cl₂ (1:1), 91%; (i) Bu₃P, nPrOH/H₂O, 94%;
(j) Allyl bromide, benzene, reflux, 86%; (k) 4N HCl/dioxane, quant.

Boc-Dap-OH (1). A slurry of N-Boc-L-asparagine (5.00 g, 21.5 mmol), EtOAc (24 mL), acetonitrile (24 mL), water (12 mL), and PIDA (8.32 g, 25.8 mmol) was cooled and stirred at 16° C. for 30 min. The temperature was then allowed to reach 20° C., and the reaction was stirred until completion (ca. 4 h). The mixture was cooled to 0° C. and filtered. The filter cake was washed with EtOAc (10 mL) and dried in vacuo to give 1 (2.73 g, 62% yield). $^1$H NMR (CD₃OD and a drop of TFA) δ4.05 (1H), 3.20-3.08 (2H), 1.45 (9H).

Boc-Dap(Cbz)-OH (2). A stirring mixture of the N-Boc-Dap-OH 1 (10.00 g, 49.02 mmol), THF (90 mL), water (30 mL), K₂CO₃ (13.53 g, 98.04 mmol) and KOH (2.75 g, 49.02 mmol) was cooled to −5° C. Cbz-Cl solution (50 wt % in toluene, 25 mL, 73.53 mmol) was then added dropwise over a period of an hour. The mixture was allowed to stir for 8 h before being concentrated under reduced pressure to remove the THF. The aqueous residue was extracted with diethyl ether (50 mL), acidified to pH 4 by solid citric acid and the resulting precipitate was extracted by CH₂Cl₂ (2 50 mL). Combined organic layers were dried (Na₂SO₄) and evaporated to furnish the free acid 2 (15.57 g, 94% yield) as a gummy white solid which was used without further purification. $^1$H NMR (300 MHz, CDCl₃) δ10.76 (1H), 7.25 (5H), 6.24, 5.67 (2H), 5.85 (1H), 5.08, 5.02 (2H), 4.36-4.23 (1H), 3.63-3.35 (2H), 1.38 (9H); $^{13}$C NMR (75 MHz, CDCl₃)δ 173.5, 157.5, 156.2, 136.4, 128.6, 128.2, 80.6, 67.3, 54.4, 42.9, 28.6.

Boc-Dap(Cbz)-OtBu (3). To an ice-cold CH₂Cl₂ (60 mL) solution of DCC (9.78 g, 47.34 mmol), t-BuOH (17.54 g, 0.24 mol) and DMAP (0.29 g, 2.37 mmol); a CH₂Cl₂ (40 mL) solution of 2 (16.00 g, 47.34 mmol) was added slowly over 20 min. Then reaction mixture was allowed to stir 1 h at 0° C. and 10 h at 20° C. Precipitated urea was then filtered off and the filtrate evaporated in vacuo. The residue was taken up in CH₂Cl₂, and if necessary, filtered free of any further precipitated urea. The CH₂Cl₂ solution was washed twice with 10% citric acid solution and with saturated NaHCO₃ solution, and then dried over Na₂SO₄. The residue obtained after evaporation of CH₂Cl₂ was purified by column chromatography to obtain the product as a clear viscous oil (15.67 g, 84% yield). $^1$H NMR (300 MHz, CDCl₃) δ7.26 (5H), 5.53 (1H), 5.45 (1H), 5.02 (2H), 4.26-4.18 (1H), 3.59-3.46 (2H), 1.38 (9H), 1.37 (9H); $^{13}$C NMR (75 MHz, CDCl₃) δ 169.9, 156.8, 155.8, 136.6, 128.7, 128.3, 82.8, 80.1, 66.9, 54.7, 43.3, 28.5, 28.1; ESI-LRMS m/z 395.2 (M+H)⁺, 417.2 (M+Na)⁺.

Boc-Dap-OtBu (4). A solution of 3 (5.00 g, 12.69 mmol) in methanol (50 mL) was placed in a Parr hydrogenation bottle and purged with argon. Palladium on Carbon (10%, 500 mg) was added under a stream of argon. The bottle was evacuated and refilled with hydrogen (3 times), pressurized to 60 psi of hydrogen and shaken for 45 minutes before being evacuated and poured into 200 mL of CH₂Cl₂. The suspension was filtered through a fine-porosity filter paper and then through a 45 μm PFTE filter. The resulting clear solution was evaporated under reduced pressure to a colorless oil (5) (3.10 g, 94% yield). $^1$H NMR (300 MHz, CDCl₃) δ5.52 (1H), 4.08-4.01 (1H), 2.93-2.80 (2H), 1.95 (2H), 1.35 (9H), 1.32 (9H); $^{13}$C NMR (75 MHz, CDCl₃) δ170.6, 155.8, 82.3, 79.9, 56.8, 44.4, 28.5, 28.2.

Boc-γ-Gla[-Cys(StBu)-OAll]-OtBu (5). An ice-cold CH₂Cl₂ solution of carbonyl diimidazole (0.63 g, 3.84 mmol) was stirred under argon for 5 min before being added via cannula to a CH₂Cl₂ solution of 11 (1.00 g, 3.49 mmol) and 0.77 mL of N-methylmorpholine (6.99 mmol) over 20 min. The reaction mixture was stirred further for a 15 min at 0° C. Then a second CH₂Cl₂ solution of 4 (1.37 g, 5.25 mmol) and 0.77 mL of NMM was added to reaction mixture in one portion. The reaction mixture was then allowed to stir at it overnight before being washed with 10% citric acid solution (2 20 mL) and brine. Organic layer was then dried over Na₂SO₄, evaporated and the residue obtained was purified by silica gel chromatography using (3:2) EtOAc/hexanes, to obtain product 5 as a colorless oil (1.26 g, 67% yield) with 20% yield of homourea of Cys(StBu)-OAll. $^1$H NMR (300 MHz, CDCl₃)δ6.03 (1H), 5.94 (2H), 5.84-5.71 (1H), 5.22-5.07 (2H), 4.61 (1H), 4.49 (2H), 4.14 (1H), 3.48-3.20 (2H), 3.03 (2H), 1.46 (9H), 1.44, 1.31 (18H); $^{13}$C NMR (75 MHz, CDCl₃)δ171.6, 170.4, 157.7, 156.1, 131.8, 118.8, 80.3, 79.9, 66.4, 55.5, 53.1, 48.2, 43.5, 42.4, 29.9, 28.5, 28.1; ESI-HRMS m/z 558.2488 (M+Na)$^+$; $C_{23}H_{41}N_3O_7S_2$+Na$^+$ requires 558.2464.

Boc-γ-Gla[-Cys(StBu)-OH]—OtBu (6). (Ph$_3$P)$_4$Pd (0.21 g, 10 mol %) was added under nitrogen to a solution of allyl ester 5 (1.00 g, 1.87 mmol) in CH$_2$Cl$_2$ (20 mL) at room temperature and the resulting mixture was treated dropwise with (1.63 mL, 18.69 mmol) morpholine. After completion of the reaction (1 h) as judged by TLC, solvent was removed in vacuo. The residue was redissolved in CH$_2$Cl$_2$ (20 mL) and the resulting solution was washed with 1N HCl (15 mL) and water (15 mL). The organic layer was dried over Na$_2$SO$_4$ and evaporated in vacuo. The crude product was purified by flash column chromatography using CH$_2$Cl$_2$-methanol (0.74 g, 80% yield). Rotamers were seen in proton and carbon NMR. $^1$H NMR (300 MHz, CDCl$_3$)δ9.36 (1H), 6.69-6.56 (1H), 6.06 (1H), 4.68 (1H), 4.31, 4.12 (1H), 3.79-3.47 (2H), 3.19-3.06 (2H), 1.44 (9H), 1.39, 1.33 (9H); $^{13}$C NMR (75 MHz, CDCl$_3$) δ175.6, 175.0, 174.5, 171.9, 171.5, 159.3, 159.1, 157.0, 155.9, 81.8, 80.6, 56.5, 54.7, 53.7, 53.2, 48.5, 48.4, 42.7, 40.9, 31.2, 31.1, 30.2, 28.7.

Boc-γ-Gla[-Cys(StBu)-Gly-OtBu]-OtBu (7). EDC (0.23 g, 1.21 mmol), HOBt (0.16 g, 1.21 mmol) and NMM (0.33 mL, 3.03 mmol) were added to a ice-cold solution of 6 (0.50 g, 1.01 mmol) and HCl.Gly-OtBu (0.25 g, 1.51 mmol) in CH$_2$Cl$_2$ (20 mL). The solution was allowed to stir for 12 h before being poured into water (20 mL). The dichloromethane layer was washed with 10% citric acid solution (25 mL), sodium bicarbonate solution (2 20 mL) and brine; dried over Na$_2$SO$_4$; filtered and the residue obtained after evaporation of CH$_2$Cl$_2$ was purified by column chromatography using 50% EtOAc/hexanes to isolate product as a colorless oil (0.47 g, 78% yield). $^1$H NMR (300 MHz, CDCl$_3$)δ7.13 (1H), 6.02-5.47 (3H), 4.61 (1H), 4.22 (1H), 3.91 (2H), 3.54 (2H), 3.10 (2H), 1.45, 1.43, 1.32 (36H); $^{13}$C NMR (75 MHz, CDCl$_3$)δ171.6, 170.3, 168.7, 158.1, 155.9, 82.5, 80.1, 55.4, 53.8, 48.2, 43.0, 42.6, 42.5, 30.2, 28.7, 28.4, 28.3; ESI-LRMS m/z 609.3 (M+H)$^+$, 631.3 (M+Na)$^+$; ESI-HRMS m/z 609.3011 (M+H)$^+$; $C_{27}H_{49}N_3O_8S_2$+H$^+$ requires 609.3039.

γ-Gla-Cys-Gly-OH (Ψ-GSH, I). To the tripeptide 7 (700 mg, 1.15 mmol) was added with stirring a mixture of CH$_2$Cl$_2$, TFA and anisole in a ratio of 2:2:1. The flask was flushed with argon and stirring was continued at ambient temperature for 3 h. The progress of the reaction was monitored by LC-MS. Upon consumption of starting material, the reaction mixture was concentrated to dryness and the residue was triturated with ether. The white precipitate (Ψ-GSH-S-StBu) was filtered and triturated with 5:1 ether-EtOH (20 mL). The process was repeated until the supernatent was colorless. The mixture was filtered and the solid thus obtained was suspended in 30 mL of water. The mixture was evaporated. The water co-evaporation was repeated four times. The residue this obtained was dried in air to afford γ-Gla-Cys(StBu)Gly (8) as a white solid (420 mg, 92% yield). $^1$H NMR (300 MHz, D$_2$O+TFA) δ4.69 (1H), 4.32 (1H), 4.03 (2H), 3.57 (2H), 3.10 (2H), 1.43 (9H SC(CH$_3$)$_3$), $^{13}$C NMR (75 MHz, D$_2$O+TFA) δ172.1, 172.0, 164.2, 158.3, 155.8, 54.8, 53.6, 48.3, 43.3, 42.1, 41.6, 30.1. ESI-APCI (mixed mode) 395.1 (M–H)$^-$.

A solution of γ-Gla-Cys(StBu)Gly (8) (0.40 g, 1.01 mmol) in 15 mL of nPrOH:H$_2$O (2:1) was adjusted to pH=8.5 with 25% aq ammonia. nBu$_3$P (400 μL, 1.51 mmol) was then added and the reaction mixture was allowed to stir at ambient temperature for 2 h. The reaction mixture was then evaporated to dryness and the residue triturated with CHCl$_3$ (3×30 mL) to afford a clear oil. This oil was loaded on a column (15 g) of C-18 bound silica gel and the column was eluted with water. Relevant fractions were evaporated to dryness to obtain an oil that was triturated with methanol to afford Ψ-GSH (I) as a white solid (180 mg, 58% yield). $^1$H NMR (300 MHz, D$_2$O) δppm 4.60 (11-1), 4.48 (1H), 4.17 (2H), 3.68-3.62, 3.41-3.34 (2H), 3.24-2.98 (2H); $^{13}$C NMR (75 MHz, CD$_3$OD-CF$_3$COOD)δ174.5, 172.6, 170.5, 159.2, 52.4, 49.1, 44.3, 42.6, 31.5; ESI-HRMS m/z 309.0798 (M+H)$^+$; $C_9H_{16}N_4O_6S$+H$^+$ requires 309.0869; Reverse phase HPLC was run on Varian Microsorb column (C18, 5 μm, 4.6×250 mm) using two solvent systems with 0.5 mL/min flow rate and detected at 220 nm. Solvent system 1: 0.04 M TEAB (triethylammonium bicarbonate) in water/70% acetonitrile in water=1/1, t$_R$=7.70 min, purity=96.06%. Solvent system 2: 0.04 M TEAB in water/70% acetonitrile in water=20–100% B linear, t$_R$=13.67 min, purity=95.90%.

Boc-Cys(StBu)-OAll (10). Hünig's base (5.6 mL, 32.31 mmol) was added to a solution of Boc-Cys(StBu)-OH (9) (5.0 g, 16.16 mmol) in dry benzene-allyl bromide (1:1, 50 mL), and the mixture was heated at reflux for 3 h. The residue obtained after evaporation of benzene was dissolved in EtOAc (200 mL); washed with 10% aqueous citric acid (3 50 mL), 5% aqueous NaHCO$_3$ (3 50 mL), brine, dried (Na$_2$SO$_4$) and concentrated in vacuo. The residue was dissolved in EtOAc/hexanes (1:2, 50 mL) and passed through a short silica gel plug (10 g). The plug was eluted further with a 100 mL of the same solvent mixture. Combined eluents were evaporated to give 4.40 g (86% yield) of 10 as a colorless oil. $^1$H NMR (300 MHz, CDCl$_3$) δ 5.96-5.83 (1H), 5.37 (1H), 5.26 (2H), 4.62 (1H), 4.58 (11-1), 3.14 (2H), 1.42 (9H), 1.29 (9H); $^{13}$C NMR (75 MHz, CDCl$_3$)δ170.5, 155.1, 131.7, 119.0, 80.3, 66.5, 53.6, 48.4, 43.0, 30.1, 28.6; ESI-LRMS m/z 372.1 (M+Na)$^+$.

HCl.NH$_2$—Cys(StBu)-OAll (11). The Boc-protected amine 10 (2.0 g, 5.73 mmol) was dissolved in 4N HCl in dioxane (12 mL) and stirred at room temperature for 1 hour. After removal of all volatiles at reduced pressure, the residue was triturated with Et$_2$O (3×10 mL) providing the hydrochloride salt 11 (1.63 g, 100% yield). $^1$H NMR (300 MHz, CDCl$_3$) δ7.78 (1H), 5.96-5.83 (1H), 5.39-5.31 (2H), 4.73 (1H), 4.54 (1H), 3.36-3.18 (2H), 1.34 (9H); $^{13}$C NMR (75 MHz, CDCl$_3$) δ167 0.6, 130.1, 120.8, 68.5, 53.4, 49.7, 38.8, 29.9; ESI-LRMS m/z 250.1 (M+H)$^+$.

EXAMPLE 5

Synthesis of Compounds 14, 15, 16 and II

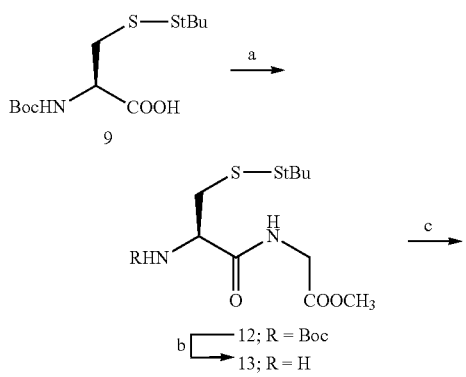

-continued

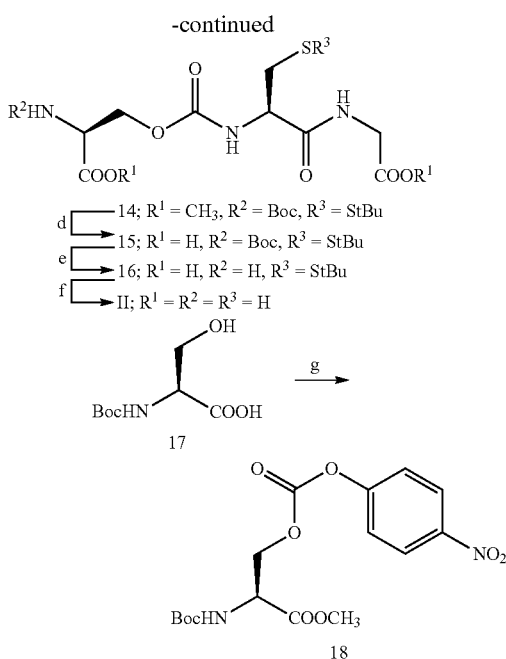

14; R[1] = CH₃, R[2] = Boc, R[3] = StBu
15; R[1] = H, R[2] = Boc, R[3] = StBu
16; R[1] = H, R[2] = H, R[3] = StBu
II; R[1] = R[2] = R[3] = H

Reagents and conditions:
(a) HCl·H₂N-Gly-OCH₃, EDCNMM, CH₂Cl₂, 89%;
(b) TFA, CH₂Cl₂;
(c) 18, dioxane, reflux, 60%;
(d) LiOHM THF/H₂O, 32%;
(e) 4N HCl/dioxane, 90%;
(f) Bu₃P, nPrPH/H₂O, 85%;
(g) p-nitrophenyl chloroformate, pyridine, 40° C., 10 h, 70%.

Boc-Cys(StBu)-Gly-OCH₃ (12). N-Boc-Cys(StBu)-OH 9 (1.00 g, 3.23 mmol) was dissolved in dry dichloromethane (25 mL) followed by the addition of EDC (0.75 g, 3.87 mmol), HOBt (0.53 g, 3.87 mmol), NMM (1.77 mL, 16.15 mmol) and glycine methyl ester hydrochloride (0.61 g, 4.84 mmol) at 0° C. under argon. The reaction mixture was then allowed to warm to room temperature and stirred overnight. After evaporation of solvent, the residue obtained was taken in EtOAc (35 mL), washed with 20% citric acid solution (2 30 mL), sat. NaHCO₃ (20 mL), brine and dried over MgSO₄. The EtOAc layer was evaporated in vacuo and resulting crude product was purified by flash silica gel column chromatography to get the dipeptide product 12 as white foam (1.09 g, 89% yield). ¹H NMR (300 MHz, CDCl₃) δ7.35, 5.81 (2H), 4.44 (1H), 3.82 (2H), 3.61 (3H), 3.02-2.83 (2H), 1.43, 1.28 (18H); ¹³C NMR (75 MHz, CDCl₃) δ171.2, 169.9, 155.5, 80.0, 53.5, 52.3, 48.0, 41.4, 37.9, 30.0, 28.5; ESI-LRMS m/z 380.5 (M+H)⁺.

TFA.H₂N-Cys(StBu)-Gly-OCH₃ (13). The dipeptide 12 (0.90 g, 2.36 mmol) was dissolved in dry dichloromethane (10 mL) followed by dropwise addition of trifluoroacetic acid (10 mL, 5 equiv.). The solution was stirred at rt for 3 h. The reaction mixture was evaporated to dryness to get brown oil which was triturated twice with freshly distilled ether to obtain amine 13 (0.93 g, 100% yield) which was used in the next reaction without further purification. ¹H NMR (300 MHz, CDCl₃) δ8.0 (1H), 4.6 (1H), 4.21-3.96 (2H), 3.80 (3H), 3.24 (2H), 1.3 (9H); ¹³C NMR (75 MHz, CDCl₃) δ170.3, 168.3, 117.0, 113.2, 53.8, 53.3, 49.5, 42.9, 40.4, 29.7.

Boc-γ-Glo[-Cys(StBu)-Gly-OCH₃]—OCH₃ (14). The N-deprotected dipeptide 13 (2.69 g, 6.83 mmol) was dissolved in dioxane (15 mL) and a solution of carbonate 18 (2.63 g, 6.83 mmol) in dioxane (15 mL) was added. After 24 h at 80° C., the reaction mixture was evaporated under vacuum and the residue was taken up in CHCl₃ (50 mL). The organic layer was washed with 0.5 N HCl (2 30 mL), sat. Na₂CO₃ solution (25 mL) and brine; dried over MgSO₄. The residue obtained after evaporation of CHCl₃ was purified by silica gel column chromatography to give the carbamate tripeptide 14 as viscous oil (2.10 g, 60% yield). ¹H NMR (300 MHz, CDCl₃) δ7.15, 5.82, 5.64 (3H), 4.64-4.46 (4H), 4.01 (2H), 3.83 (6H), 3.24 (2H), 1.45 (9H), 1.35 (9H); ¹³C NMR (75 MHz, CDCl₃) δ170.7, 170.4, 170.1, 155.6, 155.4, 80.0, 65.4, 54.7, 53.4, 52.8, 52.7, 48.6, 42.3, 41.6, 30.1, 28.6; ESI-LRMS m/z 548.2 (M+Na)⁺; ESI-HRMS m/z 548.1688 (M+Na)⁺; C₂₀H₃₅N₃O₉S₂+Na⁺ requires 548.1706.

γ-Glo-Cys-Gly-OH (II). To a solution of Boc-γ-Glo[-Cys(StBu)-Gly-OCH₃]—OCH₃ (14) (200 mg, 0.38 mmol) in dioxane-H₂O (4 mL) at 0° C. was added a precooled 1N aqueous solution of NaOH (0.2 mL) and LiCl (10 mg, catalytic). The mixture was stirred for not more than 30 minutes at 0° C. and immediately acidified to pH=7.0 with 10% aqueous acetic acid. (NOTE: the starting material is prone to base-decomposition and this step should not be carried out for more than 30 minutes) The mixture was evaporated and the residue was suspended in anisole (1 mL) and treated with TFA (4 mL). After stirring for 12 h, the reaction mixture was co-evaporated repeatedly with degassed water (5 mL) portions each, 4 times. The resulting residue was dissolved in THF-water (1:1, 4 mL) and treated with Bu₃P (1 mL, excess). After stirring for 4 h, the mixture was co-evaporated with toluene (10 mL) and the residue was triturated with CH₂Cl₂-Et₂O (5 mL, 10 times). The resulting solid was dried under high vacuum to afford 31 mg (24% yield) of the title compound. ¹H NMR (300 MHz, D₂O). δ ppm 4.54 (1H), 4.40 (1H), 4.32 (2H), 3.62-3.54, 3.40-3.31 (2H), 3.32-2.87 (2H); ¹³C NMR (75 MHz, D₂O) δ173.1, 172.6, 171.2, 164.2, 54.4, 51.0, 44.2, 41.4, 36.1. ESI-APCI (mixed mode) 309.1 [M]⁺

Boc-Ser(p-nitrophenyloxycarbonyl)-OCH₃ (18). To a stirred solution of Boc-serine(OH)—OCH₃ (17) (5.10 g, 23.26 mmol) in anhydrous pyridine (44 mL), p-nitrophenyl chlorofomate (4.60 g, 23.26 mmol) was added at room temperature. After 10 h at 40° C., the reaction mixture was evaporated in vacuo and the residue obtained was taken up in CHCl₃ (100 mL). The residue was repeatedly washed with ice-cold 1N KHSO₄ (3 50 mL), sat. Na₂CO₃ solution (75 mL) and brine; dried over MgSO₄. The residue obtained after evaporation was purified by silica gel column chromatography using 1% methanol—CHCl₃ as eluant to get carbonate 18 as oil (6.25 g, 70% yield). ¹H NMR (300 MHz, CDCl₃) δ8.2, 7.4 (4H), 5.45 (1H), 4.65 (1H), 4.53 (2H), 3.8 (3H), 1.4 (9H); ¹³C NMR (75 MHz, CDCl₃) δ169.7, 155.4, 155.2, 154.2, 145.6, 125.4, 121.8, 76.9, 68.8, 53.3, 52.9, 28.5.

EXAMPLE 6

Synthesis of Compounds 22, 23, 24 and III

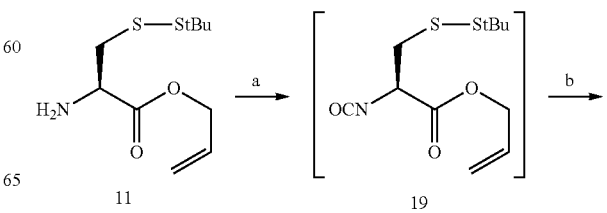

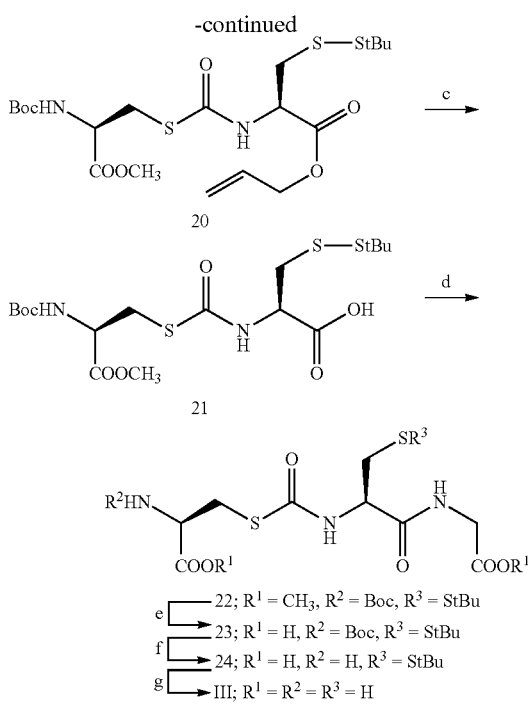

22; R¹ = CH₃, R² = Boc, R³ = StBu
23; R¹ = H, R² = Boc, R³ = StBu
24; R¹ = H, R² = H, R³ = StBu
III; R¹ = R² = R³ = H

Reagents and conditions:
(a) triphosgene, NaHCO₃, CH₂Cl₂;
(b) Boc-Cys-OCH₃, DIPEA, CH₂Cl₂, 56% over 2 steps;
(c) Pd(PPh₃)₄, morpholine, CH₂Cl₂, 76%
(d) HCl·H₂N-Gly-OCH₃, EDC, HOBt, NMM, CH₂Cl₂, 81%;
(e) LiOH, THF/H₂O, 22%;
(f) 4N HCl/dioxane, 91%;
(g) Bu₃P, nPrPH/H₂O, 87%;

Boc-γ-Glt[-Cys(StBu)-OAll]-OCH₃ (20). Amine 11 (1.00 g, 2.75 mmol) was dissolved in dichloromethane (10 mL) followed by addition of 10 mL of saturated NaHCO₃ solution. This biphasic system was cooled at 0° C. and then triphosgene (0.28 g, 0.94 mmol) was added in one portion. After stirring the reaction mixture for 30 min at 0° C., it was poured in separating funnel and the dichloromethane layer was separated. Then aqueous layer was washed twice with dichloromethane (10 mL) and combined dichloromethane layers were dried over MgSO₄; evaporated to dryness to slight yellow oil as isocyanate 19 (assumed to be 100% conversion).

The dichloromethane solution of thiol of Boc-Cys-OCH₃ (0.78 g, 3.30 mmol) and diisopropylethylamine (0.43 mL, 3.30 mmol) was added to the dichloromethane (5 mL) solution of isocyanate 19 and then solution was allowed to stir at room temperature overnight. The viscous oil obtained after evaporation of solvent was taken in EtOAc and washed with 20% citric acid solution, sat. NaHCO₃, and brine, dried over MgSO₄ and evaporated to dryness to get crude product which was purified by silica gel chromatography to obtain thiocarbamate dipeptide 20 (0.786 g, 56% yield).

¹H NMR (300 MHz, CDCl₃) δ6.61 (1H), 5.92-5.80 (1H), 5.52 (1H), 5.33-5.21 (2H), 4.80 (1H), 4.63 (2H), 4.41 (1H), 3.65 (3H), 3.44-3.06 (4H), 1.42, 1.29 (18H); ¹³C NMR (75 MHz, CDCl₃) δ171.0, 169.5, 166.6, 155.2, 131.4, 119.2, 80.1, 66.7, 54.0, 54.0, 52.8, 48.5, 42.2, 32.2, 30.0, 28.6; ESI-LRMS m/z 533.1 (M+Na)⁺.

Boc-γ-Glt[-Cys(StBu)-OH]—OCH₃ (21). To a solution of dipeptide 20 (1.00 g, 1.96 mmol)) in dry CH₂Cl₂, morpholine (1.72 mL, 19.61 mmol) and catalytic tetrakis(triphenylphosphine)palladium (0.23 g, 10 mol %) was added and the reaction mixture was allowed to stir at room temperature protected from light under argon until the disappearance of starting material 20 (~4 h). The reaction mixture was then evaporated to dryness to get a sticky solid, which was taken in 10% Na₂CO₃ solution (20 mL) and washed with ether (20 mL). The aqueous layer was neutralized by 1 N HCl to pH 3-4 and precipitated dipeptide acid 21 was extracted with CHCl₃ (2 30 mL). Combined CHCl₃ layers were washed with brine, dried over MgSO₄ and evaporated in vacuo to obtain acid 21 as a sticky solid (0.70 g, 76% yield). ¹H NMR (300 MHz, CD₃OD) δ4.74 (1H), 4.62 (1H), 3.78 (3H), 3.68-2.93 (4H), 1.42, 1.28 (18H); ¹³C NMR (75 MHz, CD₃OD) δ174.1, 171.4, 159.2, 156.3, 80.1, 66.7, 55.0, 52.4, 52.8, 48.5, 42.2, 32.2, 30.0, 28.6.

Boc-γ-Glt[-Cys(StBu)-Gly-OCH₃]—OCH₃ (22). To a solution of the dipeptide acid 21 (0.70 g, 1.48 mmol) in CH₂Cl₂ (15 mL) were added EDC (0.34 g, 1.78 mmol), HOBt (0.24 g, 1.78 mmol), NMM (0.49 mL, 4.46 mmol) and glycine methyl ester hydrochloride (0.28 g, 2.23 mmol) at 0° C. The reaction mixture was then allowed to warm to it and stirred overnight. After evaporation of dichloromethane, the residue obtained was taken up in EtOAc (30 mL), washed with 20% aqueous citric acid (2 20 mL), sat. NaHCO₃ solution (15 mL), brine, dried over MgSO₄ and evaporated to dryness. The crude product obtained was purified by silica gel column chromatography to get the thiocarbamate tripeptide 22 as oil (0.66 g, 81% yield). ¹H NMR (300 MHz, CDCl₃) δ6.15 (1H), 4.82, 4.75 (21-1), 4.04 (2H), 3.68 (6H), 3.54-3.01 (4H), 1.40, 1.26 (18H); ¹³C NMR (75 MHz, CDCl₃) δ172.7, 171.4, 169.1, 159.6, 156.4, 79.8, 54.7, 52.4, 52.8, 47.6, 41.3, 38.1, 31.3, 30.1, 28.8; ESI-LRMS m/z 564.2 (M+Na)⁺; ESI-HRMS m/z 564.1512 (M+Na)⁺; C₂₀H₃₅N₃O₈S₃+Na⁺ requires 564.1484.

γ-Glt-Cys-Gly-OH (III). To a solution of Boc-γ-Glt[-Cys(StBu)-Gly-OCH₃]—OCH₃ (22) (200 mg, 0.36 mmol) in dioxane-H₂O (4 mL) at 0° C. was added a precooled 1N aqueous solution of NaOH (0.2 mL) and LiCl (10 mg, catalytic). The mixture was stirred for not more than 30 minutes at 0° C. and immediately acidified to pH=7.0 with 10% aqueous acetic acid. (NOTE: the starting material is prone to base-decomposition and this step should not be carried out for more than 30 minutes) The mixture was evaporated and the residue was suspended in anisole (1 mL) and treated with TFA (4 mL). After stirring for 12 h, the reaction mixture was co-evaporated repeatedly with degassed water (5 mL) portions each, 4 times. The resulting residue was dissolved in THF-water (1:1, 4 mL) and treated with Bu₃P (1 mL, excess). After stirring for 4 h, the mixture was co-evaporated with toluene (10 mL) and the residue was triturated with CH₂Cl₂Et₂O (5 mL, 10 times). The resulting solid was dried under high vacuum to afford 20 mg (17% yield) of the title compound. ¹H NMR (300 MHz, D₂O). δ ppm 4.63 (1H), 4.48 (1H), 4.22 (2H), 3.61-3.40, 3.37-3.32 (2H), 3.12-2.61 (2H); ¹³C NMR (75 MHz, D₂O) δ172.1, 172.0, 171.9, 167.1, 52.1, 52.0, 43.1, 41.6, 35.0. ESI-APCI (mixed mode) 325.1 [M]⁺

EXAMPLE 7

Synthesis of Compounds 25 and IV

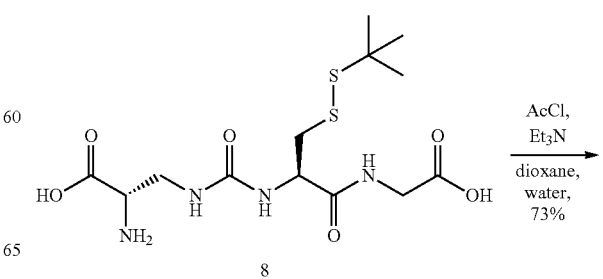

8

-continued

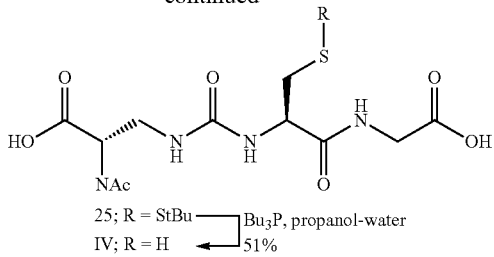

25; R = StBu  
IV; R = H

Bu₃P, propanol-water  
51%

N-acetyl-γ-Gla-Cys(S-StBu)-Gly-OH (25). To a solution of HCl.γ-Gla-Cys(S-StBu)-Gly-OH (8) (200 mg, 0.5 mmol) in dioxane-water (4:1) was added Et₃N (1 mL, excess) and acetic anhydride (0.5 mL, excess). The mixture was stirred at ambient temperature for 24 h and evaporated to dryness. Degassed water (10 mL) was added and the mixture was heated to 60° C. for 20 minutes, and then evaporated to dryness again. The residue obtained was coevaporated with degassed water (10 mL) thrice before finally being triturated with dry ether to obtain a hygroscopic white crystalline solid (163 mg, 73% yield). ¹H NMR (400 MHz, CD₃OD) δ ppm 4.94-4.80 (1H), 4.62-4.56 (1H), 4.02-3.90 (2H), 3.62 (2H), 3.04-2.82 (br, 2H), 2.06 (3H), 1.46 (9H). ¹³C NMR (100 MHz, CD₃OD) δ ppm 174.2, 174.1, 171.5, 168.4, 163.0, 88.3, 76.6, 72.4, 59.3, 50.8, 47.2, 32.4, 23.8. ESI-MS (negative mode) 436.1 (M−H)⁻ (No peak in positive mode ESI).

N-acetyl-γ-Gla-Cys-Gly-OH (IV). To N-acetyl-γ-Gla-Cys(S-StBu)-Gly-OH (25) (100 mg, 0.23 mmol) in n-PrOH—H₂O (3:1, 1 mL) was added Bu₃P (300 μL, excess). After stirring the mixture at ambient temperature overnight, it was evaporated to an oily residue that was co-evaporated with degassed water (5 mL). The residue thus obtained was stirred in dry ether (5 mL) for an hour to precipitate a white solid. This mixture was filtered very quickly under a stream of dry argon and the product was dried under high vacuum at room temperature overnight to afford a deliquescent pale yellow crystalline solid (41 mg, 51% yield). ¹H NMR (600 MHz, CD₃OD) 4.57-4.28 (2H), 3.92-3.84 (2H), 3.32-2.91 (2H), 2.31-2.16 (2H), 2.12 (3H). ¹³C NMR (125 MHz, CD₃OD) 173.1, 173.0, 171.6, 168.0, 163.2, 78.2, 72.1, 70.4, 58.0, 51.3, 45.2, 24.2. ESI-MS (negative mode) 348.1 (M−H)⁻ (No peak in positive mode ESI).

EXAMPLE 8

Synthesis of Compound V

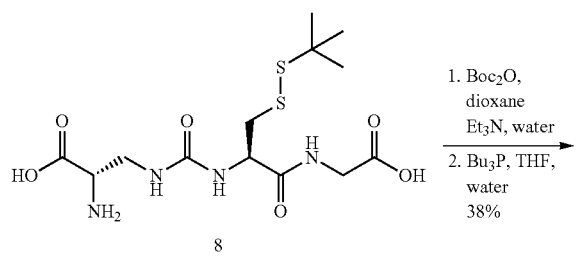

1. Boc₂O, dioxane Et₃N, water
2. Bu₃P, THF, water
38%

Boc-γ-Gla-Cys-Gly-OH (V). To 8 (100 mg, 0.22 mmol) in dioxane-water (1:1, 2 mL) was added Boc anhydride (100 mg, excess) and Et₃N (1 mL, excess) at ambient temperature. After stirring overnight, the reaction was partitioned between water (5 mL) and ether (5 mL). The aqueous layer was washed with another portion of ether and then evaporated to afford a gummy residue that was dissolved in THF-H₂O (1:1, 2 mL). Bu₃P (1 mL, excess) was added and the mixture stirred overnight. Evaporation of the reaction mixture was followed by trituration with CH₂Cl₂-Ether (1:1, 5 mL, 3×) to afford a white solid (42 mg, 38% yield). ¹H NMR (400 MHz, CD₃OD) 4.63-4.42 (1H), 4.30-4.18 (1H), 4.03-3.92 (2H), 3.43-3.30 (2H), 2.76-2.51 (2H). ¹³C NMR (100 MHz, CD₃OD) 176.3, 173.0, 171.3, 171.0, 161.0, 89.3, 76.2, 74.9, 66.0, 54.7, 51.2, 28.8. ESI-MS (negative ion mode) 406.1 (M−H)⁻ (no peak visible in positive ion mode).

EXAMPLE 9

Synthesis of Compound VI

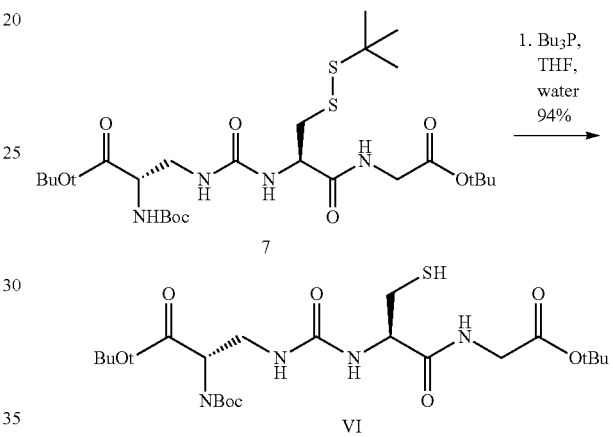

Boc-γ-Gla(OtBu)-Cys-Gly-OtBu. To Boc-γ-Gla(OtBu)-Cys(S-StBu)-Gly-OtBu (7) (0.25 g, 0.41 mmol) in THF (10 mL) was added water (1 mL) and tributylphosphine (0.17 mL, 0.82 mmol) followed by stirring for 2 h under argon after which the TLC indicated complete disappearance of the starting material. The mixture was diluted with CH₂Cl₂ (30 mL) and dried over Na₂SO₄, concentrated, and purified by flash silica gel chromatography using EtOAc/hexane (7:3) as the eluent. The title compound was obtained as a colorless oil (0.20 g, 94% yield). ¹H NMR (400 MHz, CD₃OD) δ ppm 4.44-4.31 (1H), 4.20-4.08 (1H), 4.03-3.90 (2H), 3.64-3.51 (2H), 2.50-2.37 (2H), 1.42 (9H, rotamers), 1.40+1.38 (18H, rotamers), 1.20 (9H). ¹³C NMR (100 MHz, CD₃OD). 177.3, 173.4, 172.0, 171.4, 163.2, 91.3, 90.0. 88.1, 75.3, 73.2, 70.0, 63.2, 57.3, 30.15, 30.10, 28.1. ESI+APCI mixed mode-MS (positive ion mode) 520.2 (M+H)⁺.

EXAMPLE 10

Synthesis of Compound VIII

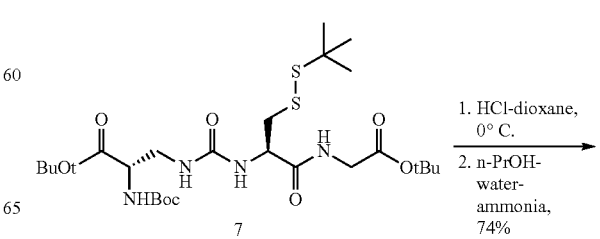

1. HCl-dioxane, 0° C.
2. n-PrOH-water-ammonia, 74%

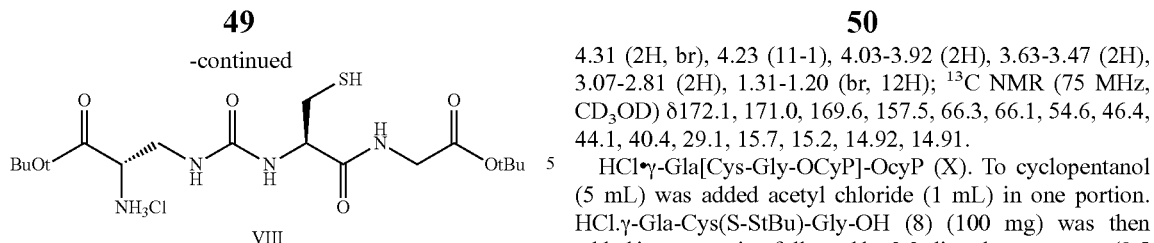

HCl•γ-Gla[-Cys-Gly-OtBu]-OtBu (VIII). Compound 7 (304 mg, 0.5 mmol) was added in one portion to a chilled (0° C.) solution of HCl in dioxane (4 M) with vigorous stirring. The ice-bath was removed and the solution was allowed to stir at ambient temperature for 20 minutes and immediately evaporated in high vacuum. The resulting pale yellow solid was triturated with Et$_2$O-EtOH (9:1), 4 mL, to precipitate a colorless solid that was dissolved in n-PrOH—H$_2$O- liquor NH$_3$ (4:1:0.5, 2 mL). Bu$_3$P (0.5 mL, excess) was added and the mixture was stirred overnight under argon. The resulting clear biphasic mixture was evaporated to a pale yellow oil that was coevaporated with degassed water (5 mL) twice. The residue was then triturated with dry ether (5 mL) under argon until the oil converted to a white solid. Filtration of this mixture afforded the title compound (168 mg, 74% yield). $^1$H NMR (400 MHz, CD$_3$OD). δ ppm $^1$H NMR (300 MHz, CD$_3$OD) δ4.67 (1-1), 4.13 (1H), 4.06-3.94 (2H), 3.70 (2H), 3.06-2.77 (2H), 1.23 (9H), 1.20 (9H); $^{13}$C NMR (75 MHz, CD$_3$OD) δ172.0, 171.3, 169.4, 157.6, 89.3, 88.1, 54.4, 46.7, 43.7, 40.6, 28.9, 31.3, 29.8. ESI-MS mixed APCI positive mode 421.2 (M+H)$^+$

EXAMPLE 11

Synthesis of Compound IX and X

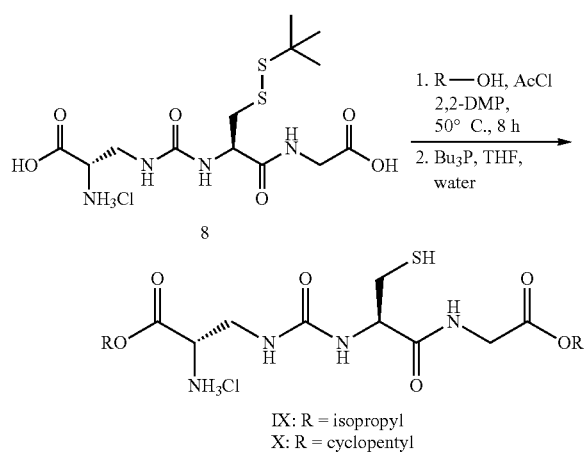

HCl•γ-Gla[Cys-Gly-OiPr]-OiPr (IX). To i-PrOH (10 mL) was added TMS-Cl (2 mL) dropwise at ambient temperature. HCl.γ-Gla-Cys(S-StBu)-Gly-OH (8) (100 mg) was then added in one portion followed by 2,2-dimethoxypropane (0.5 mL), and the mixture was heated to 50° C. for 8 h. Evaporation of the reaction mixture afforded a gummy solid that was dissolved in THF-water (1:1, 2 mL) and treated with Bu$_3$P (1 mL). The mixture was stirred overnight and then evaporated to a gummy residue which was triturated vigorously with ether to afford the title compound as a white solid (95 mg, 87% yield). $^1$H NMR (300 MHz, CD$_3$OD) δ4.64 (1H), 4.46-4.31 (2H, br), 4.23 (11-1), 4.03-3.92 (2H), 3.63-3.47 (2H), 3.07-2.81 (2H), 1.31-1.20 (br, 12H); $^{13}$C NMR (75 MHz, CD$_3$OD) δ172.1, 171.0, 169.6, 157.5, 66.3, 66.1, 54.6, 46.4, 44.1, 40.4, 29.1, 15.7, 15.2, 14.92, 14.91.

HCl•γ-Gla[Cys-Gly-OCyP]-OcyP (X). To cyclopentanol (5 mL) was added acetyl chloride (1 mL) in one portion. HCl.γ-Gla-Cys(S-StBu)-Gly-OH (8) (100 mg) was then added in one portion followed by 2,2-dimethoxypropane (0.5 mL), and the mixture was heated to 50° C. for 8 h. The mixture was admixed with xylenes (5 mL) and evaporated. The xylenes procedure was repeated 4 times to remove maximal quantity of cyclopentanol and the residue was then triturated with ether to yield a gum that was dissolved in THF-water (1:1, 2 mL) and treated with Bu$_3$P (1 mL). The mixture was stirred overnight and then evaporated to a gummy residue which was triturated vigorously with ether to afford the title compound as a pale yellow white solid (82 mg, 68% yield). $^1$H NMR (300 MHz, CD$_3$OD) δ4.71 (11-1), 4.53-4.40 (2H), 4.22-3.96 (3H), 3.64-3.49 (2H), 3.02-2.79 (2H), 2.05-1.73 (8H), 1.63-1.30 (8H); $^{13}$C NMR (75 MHz, CD$_3$OD) δ172.2, 171.1, 169.5, 156.9, 73.1, 73.0, 54.5, 46.4, 43.1, 40.1, 32.4, 31.0, 30.6, 30.4, 29.2, 26.1, 25.3, 25.1, 24.6 ESI/APCI mixed mode 445.2 (M+H)$^+$

EXAMPLE 12

Synthesis of Compound XI

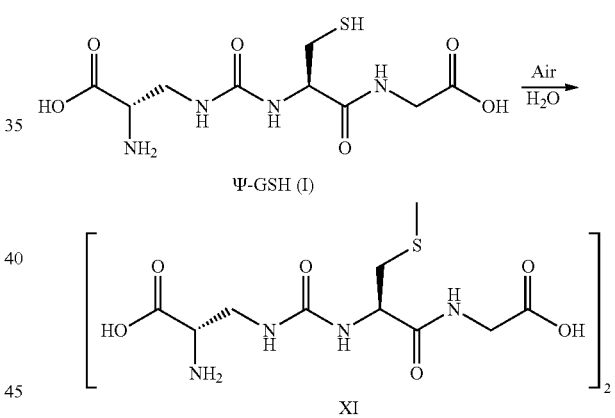

[γ-Gla-Cys-Gly-OH]$_2$ (XI) An aqueous solution of Ψ-GSH (I) (60 mg, 0.2 mmol) was stirred vigorously in a wide vial open to air for 7 days. The reaction was monitored by LC-MS for consumption of Y-GSH. After 7 days, the mixture was evaporated to gum that was washed thoroughly while triturating on a frit (no vacuum applied) with ether and dried in air to afford the title compound as a nonhygroscopic white solid (53 mg, 88% yield). $^1$H NMR (300 MHz, D$_2$O) δ ppm 4.59 (1H), 4.39 (1H), 4.13 (2H), 3.62-3.54, 3.40-3.31 (2H), 3.32-2.87 (2H); $^{13}$C NMR (75 MHz, D$_2$O) δ174.3, 171.6, 170.2, 159.9, 51.2, 48.3, 44.8, 41.0, 36.5. ESI/APCI mixed mode (negative mode) 613.2 (M–H)$^{-1}$

EXAMPLE 13

Biological Testing of Compounds of the Invention

Protection against β-amyloid$^{1-42}$ cytotoxicity in SH-SY-5Y cells was measured by standard MTT assays. SH-SY-5Y cells were seeded in 96-well plates at the density of 30,000 cells/well. After overnight incubation, the cells were exposed to GSH, Ψ-GSH or its analogs at a concentration of 1 mM for 24 h at 37° C. After 24 h of incubation, the drug-containing medium was replaced with media containing 20 μM β-amyloid$^{1-42}$ peptide and the incubation was allowed to continue for additional 24 hours after the addition of the drugs. At the end of the incubation, 20 μl, of MTT stock solution (5 mg/mL) was added to each well and incubated for 3 h at 37° C. The MTT reaction medium was discarded and the purple-blue MTT formazan crystals were dissolved by the addition of 100 μL of 0.1 N HCl in isopropanol. The optical density (OD), a reflection mitochondrial function of the viable cells, was read directly with a microplate reader (BioTek SynergyHT, VT, USA) at 580 nm and a reference wavelength of 680 nm. Concentration response graphs were generated for each drug using GraphPad Prism software (GraphPad Software, Inc., San Diego, Calif., USA). Results are expressed as mean percent inhibition of β-amyloid toxicity with the standard error of the mean.

| Compound | % Inhibition of Cell Growth | |
|---|---|---|
| (1 mM) | without Aβ$^{1-42}$ | with Aβ$^{1-42}$ |
| control | 0 | 52 |
| GSH | 0 | 12 |
| Ψ-GSH (I) | 0 | 4 |
| II | 1 | 56 |
| III | 2 | 55 |
| IV | 0 | 3 |
| V | 1 | 10 |
| VI | 2 | 18 |
| 7 | 0 | 41 |
| VIII | 1 | 50 |
| IX | 0 | 31 |
| X | 0 | 27 |
| XI | 1 | 24 |

EXAMPLE 14

The following illustrate representative pharmaceutical dosage forms, containing a compound of formula I ('Compound X'), for therapeutic or prophylactic use in humans.

| (i) Tablet 1 | mg/tablet |
|---|---|
| Compound X = | 100.0 |
| Lactose | 77.5 |
| Povidone | 15.0 |
| Croscarmellose sodium | 12.0 |
| Microcrystalline cellulose | 92.5 |
| Magnesium stearate | 3.0 |
| | 300.0 |

| (ii) Tablet 2 | mg/tablet |
|---|---|
| Compound X = | 20.0 |
| Microcrystalline cellulose | 410.0 |
| Starch | 50.0 |
| Sodium starch glycolate | 15.0 |
| Magnesium stearate | 5.0 |
| | 500.0 |

| (iii) Capsule | mg/capsule |
|---|---|
| Compound X = | 10.0 |
| Colloidal silicon dioxide | 1.5 |
| Lactose | 465.5 |
| Pregelatinized starch | 120.0 |
| Magnesium stearate | 3.0 |
| | 600.0 |

| (iv) Injection 1 (1 mg/ml) | mg/ml |
|---|---|
| Compound X = (free acid form) | 1.0 |
| Dibasic sodium phosphate | 12.0 |
| Monobasic sodium phosphate | 0.7 |
| Sodium chloride | 4.5 |
| 1.0N Sodium hydroxide solution (pH adjustment to 7.0-7.5) | q.s. |
| Water for injection | q.s. ad 1 mL |

| (v) Injection 2 (10 mg/ml) | mg/ml |
|---|---|
| Compound X = (free acid form) | 10.0 |
| Monobasic sodium phosphate | 0.3 |
| Dibasic sodium phosphate | 1.1 |
| Polyethylene glycol 400 | 200.0 |
| 1.0N Sodium hydroxide solution (pH adjustment to 7.0-7.5) | q.s. |
| Water for injection | q.s. ad 1 mL |

| (vi) Aerosol | mg/can |
|---|---|
| Compound X = | 20.0 |
| Oleic acid | 10.0 |
| Trichloromonofluoromethane | 5,000.0 |
| Dichlorodifluoromethane | 10,000.0 |
| Dichlorotetrafluoroethane | 5,000.0 |

EXAMPLE 14

The following illustrates a representative dermatological formulation containing a compound of formula I ('Compound X'), for therapeutic or prophylactic use in humans.

Cream: 2-12% Active ingredients (Compound X) and 88-98% Inactive ingredients

| Inactive Ingredients | % (w/w) |
|---|---|
| Water | 64.90 |
| Hexadecan-1-ol ($C_{16}H_{34}O$, Cetyl alcohol) | 3.0 |
| Octadecan-1-ol ($C_{18}H_{38}O$, Stearyl alcohol) | 8.5 |
| Isopropyl myristate ($C_{17}H_{34}O_2$) | 1.0 |
| Glycerine | 0.2 |
| Propylene glycol | 20.0 |
| Polysorbate 20 (TWEEN 20) | 2.0 |
| Isopropyl palmitate | 0.2 |
| Benzoic Acid | 0.2 |
| Total for inactive ingredients | 100.00 |

The above formulations may be obtained by conventional procedures well known in the pharmaceutical art.

All publications, patents, and patent documents are incorporated by reference herein, as though individually incorporated by reference. The invention has been described with

What is claimed is:
1. A compound of formula I:

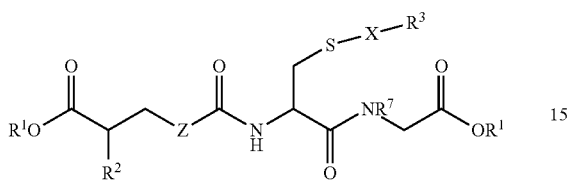
(I)

wherein:
each $R^1$ is independently H, $(C_1-C_6)$alkyl, $(C_3-C_8)$cycloalkyl, aryl$(C_1-C_6)$alkyl, or heteroaryl$(C_1-C_6)$alkyl;
each $R^{1a}$ is independently H, $(C_1-C_6)$alkyl, $(C_3-C_8)$cycloalkyl, aryl$(C_1-C_6)$alkyl, or heteroaryl$(C_1-C_6)$alkyl;
$R^2$ is OH, $NH_2$, —O—C(=O)—$R^{1a}$, —NH—C(=O)—$R^{1a}$ or —NH—C(=O)O—$R^{1a}$;
Z is —NH—, —O—, or —S—;
X is —S— or absent, $R^3$ is H, —$(CH_2)CH(NHR^6)CO_2H$ or

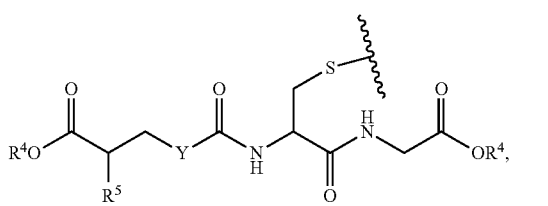

and $R^7$ is H; or X is absent, and $R^3$ and $R^7$ together with the atoms to which they are attached form a heterocycle, wherein the heterocycle is optionally substituted with one or more groups selected from oxo (=O), $(C_1-C_6)$alkyl, $(C_3-C_8)$cycloalkyl, aryl$(C_1-C_6)$alkyl and heteroaryl$(C_1-C_6)$ alkyl;
each $R^4$ is independently H, $(C_1-C_6)$alkyl, $(C_3-C_8)$cycloalkyl, aryl$(C_1-C_6)$alkyl, or heteroaryl$(C_1-C_6)$alkyl;
$R^5$ is OH, $NH_2$, —O—C(=O)—$R^{1a}$, —NH—C(=O)—$R^{1a}$ or —NH—C(=O)O—$R^{1a}$;
$R^6$ is H, $(C_1-C_6)$alkyl or —C(=O)—$R^1$; and
Y is —$CH_2$—, —S— or NH;
or a salt thereof;
provided the compound of formula I is not a compound of formula:

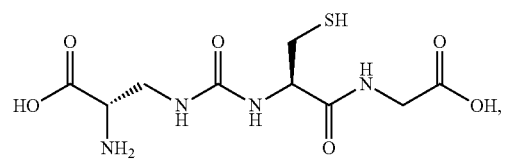

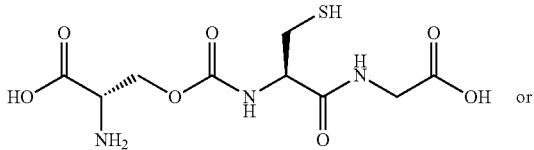

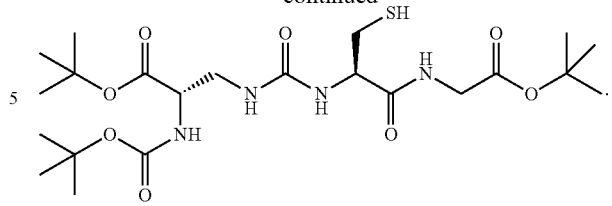

2. The compound of claim 1, which is a compound of formula I':

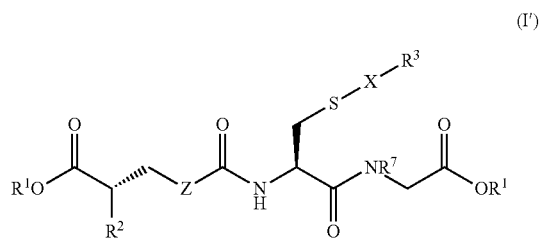
(I')

wherein:
each $R^1$ is independently H, $(C_1-C_6)$alkyl, $(C_3-C_8)$cycloalkyl, aryl$(C_1-C_6)$alkyl, or heteroaryl$(C_1-C_6)$alkyl;
each $R^{1a}$ is independently H, $(C_1-C_6)$alkyl, $(C_3-C_8)$cycloalkyl, aryl$(C_1-C_6)$alkyl, or heteroaryl$(C_1-C_6)$alkyl;
$R^2$ is OH, $NH_2$, —O—C(=O)—$R^{1a}$, —NH—C(=O)—$R^{1a}$ or —NH—C(=O)O—$R^{1a}$;
Z is —NH—, —O—, or —S—;
X is —S— or absent, $R^3$ is H, —$(CH_2)CH(NHR^6)CO_2H$ or

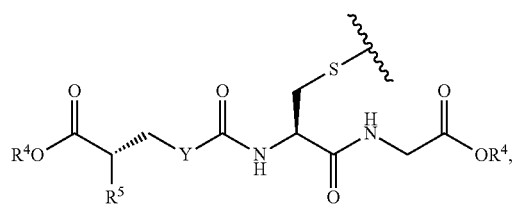

and $R^7$ is H; or X is absent, and $R^3$ and $R^7$ together with the atoms to which they are attached form a heterocycle, wherein the heterocycle is optionally substituted with one or more groups selected from oxo (=O), H, $(C_1-C_6)$alkyl, $(C_3-C_8)$cycloalkyl, aryl$(C_1-C_6)$alkyl and heteroaryl$(C_1-C_6)$ alkyl;
each $R^4$ is independently H, $(C_1-C_6)$alkyl, $(C_3-C_8)$cycloalkyl, aryl$(C_1-C_6)$alkyl, or heteroaryl$(C_1-C_6)$alkyl;
$R^5$ is OH, $NH_2$, —O—C(=O)—$R^{1a}$, —NH—C(=O)—$R^{1a}$ or —NH—C(=O)O—$R^{1a}$;
$R^6$ is H, $(C_1-C_6)$alkyl or —C(=O)—$R^1$; and
Y is —$CH_2$—, —S— or NH;
or a salt thereof;
provided the compound of formula I' is not a compound of formula:

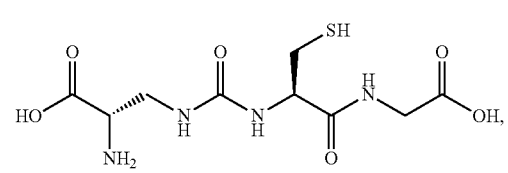

-continued

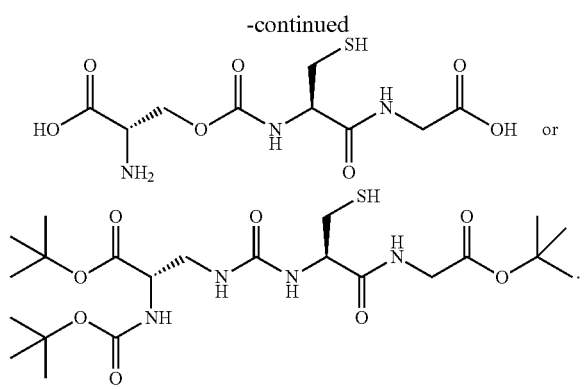

3. The compound of claim 1, wherein $R^3$ is H or

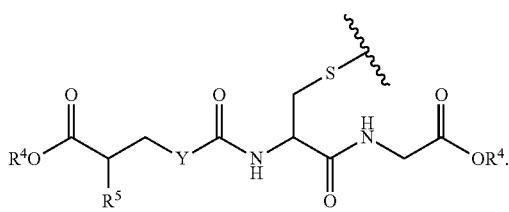

4. The compound of claim 1, which is a compound of formula Ia:

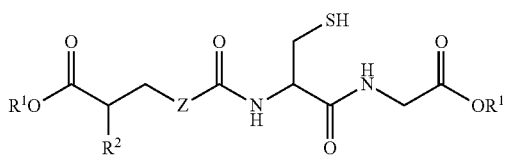
(Ia)

or a salt thereof.

5. The compound of claim 1, which is a compound of formula Ia':

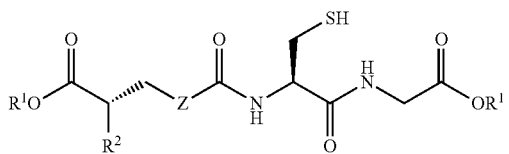
(Ia')

or a salt thereof.

6. The compound of claim 1, wherein $R^4$ is H, $(C_1-C_6)$alkyl or $(C_3-C_8)$ cycloalkyl; $R^5$ is $NH_2$, —NH—C(=O)—$R^{1a}$ or —NH—C(=O)O—$R^{1a}$; and Y is —NH— or —S—.

7. The compound of claim 1, wherein each $R^1$ is independently H, $(C_1-C_6)$alkyl or $(C_3-C_8)$cycloalkyl.

8. The compound of claim 1, wherein $R^2$ is $NH_2$, —NH—C(=O)—$R^{1a}$ or —NH—C(=O)O—$R^{1a}$.

9. The compound of claim 1, wherein Z is —NH— or —O—.

10. The compound of claim 1, wherein Z is —NH—.

11. The method of claim 1, wherein Y is —S— or —NH—.

12. The compound of claim 1, which is a compound of formula:

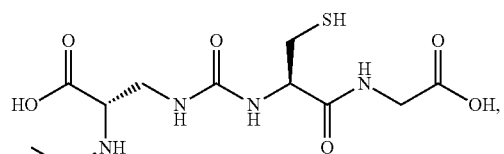

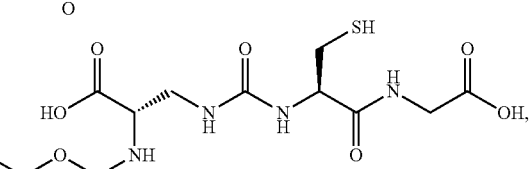

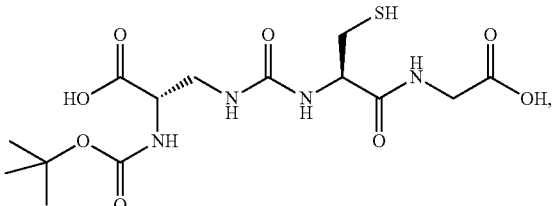

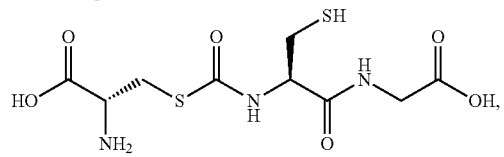

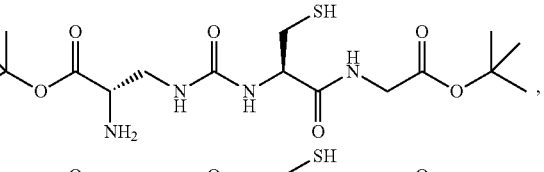

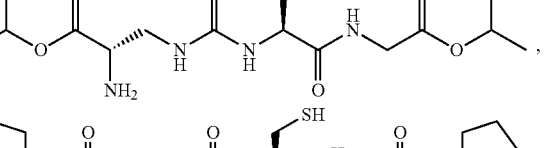

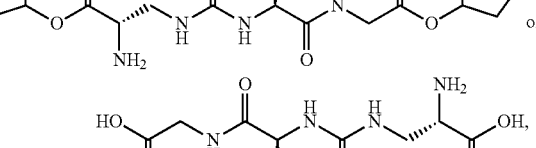

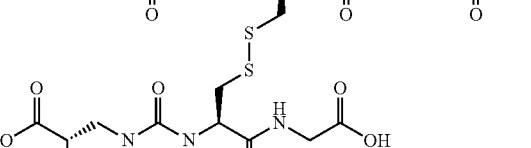

or a salt thereof.

13. A pharmaceutical composition comprising a compound of formula I as described in claim 1, or a pharmaceutically acceptable salt thereof, and a pharmaceutically acceptable diluent or carrier.

14. A method for treating Alzheimer's Disease, Parkinson's disease, amyotrophic lateral sclerosis (ALS), diabetes, acetaminophen toxicity or stroke in a mammal, comprising administering a compound of formula I as described in claim 1, or a pharmaceutically acceptable salt thereof, to the mammal.

15. The method of claim 14 for treating acetaminophen toxicity.

16. A method for treating Alzheimer's Disease, Parkinson's disease, amyotrophic lateral sclerosis (ALS), diabetes, acetaminophen toxicity or stroke in a mammal, comprising administering a compound of formula (I):

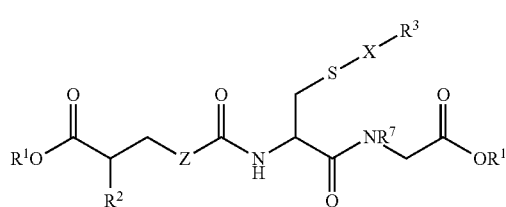
(I)

wherein:
each $R^1$ is independently H, $(C_1$-$C_6)$alkyl, $(C_3$-$C_8)$cycloalkyl, aryl$(C_1$-$C_6)$alkyl, or heteroaryl$(C_1$-$C_6)$alkyl;
each $R^{1a}$ is independently H, $(C_1$-$C_6)$alkyl, $(C_3$-$C_8)$cycloalkyl, aryl$(C_1$-$C_6)$alkyl, or heteroaryl$(C_1$-$C_6)$alkyl;
$R^2$ is OH, $NH_2$, —O—C(=O)—$R^{1a}$, —NH—C(=O)—$R^{1a}$ or —NH—C(=O)O—$R^{1a}$;
Z is —NH—, —O—, or —S—;
X is —S— or absent, $R^3$ is H, $(C_1$-$C_6)$alkyl, —$(CH_2)$CH$(NHR^6)CO_2H$ or

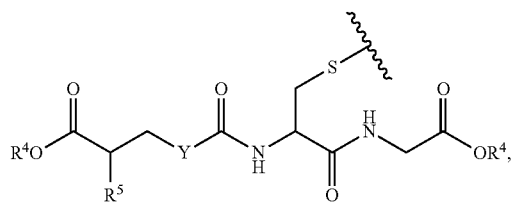

and $R^7$ is H; or X is absent, and $R^3$ and $R^7$ together with the atoms to which they are attached form a heterocycle, wherein the heterocycle is optionally substituted with one or more groups selected from oxo (=O), H, $(C_1$-$C_6)$alkyl, $(C_3$-$C_8)$cycloalkyl, aryl$(C_1$-$C_6)$alkyl and heteroaryl$(C_1$-$C_6)$ alkyl;
each $R^4$ is independently H, $(C_1$-$C_6)$alkyl, $(C_3$-$C_8)$cycloalkyl, aryl$(C_1$-$C_6)$alkyl, or heteroaryl$(C_1$-$C_6)$alkyl;
$R^5$ is OH, $NH_2$, —O—C(=O)—$R^{1a}$, —NH—C(=O)—$R^{1a}$ or —NH—C(=O)O—$R^{1a}$;
$R^6$ is H, $(C_1$-$C_6)$alkyl or —C(=O)—$R^1$; and
Y is —$CH_2$—, —O—, —S— or NH;
or a pharmaceutically acceptable salt thereof to the mammal.

17. The method of claim 16, wherein the compound of formula I is a compound of formula I':

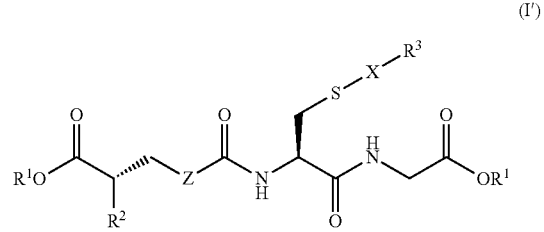
(I')

wherein:
each $R^1$ is independently H, $(C_1$-$C_6)$alkyl, $(C_3$-$C_8)$cycloalkyl, aryl$(C_1$-$C_6)$alkyl, or heteroaryl$(C_1$-$C_6)$alkyl;
$R^2$ is OH or $NH_2$, or O—C(=O)—$R^1$ or NH—C(=O)—$R^1$
X is —S— or absent;
Z is —NH—, —O—, or —S—;
$R^3$ is H or:

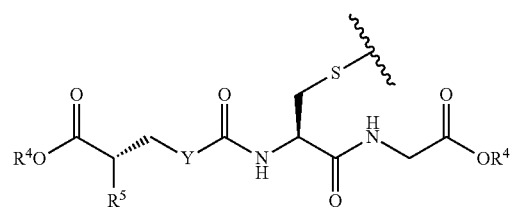

each $R^4$ is independently H, $(C_1$-$C_6)$alkyl, $(C_3$-$C_8)$cycloalkyl, aryl$(C_1$-$C_6)$alkyl, or heteroaryl$(C_1$-$C_6)$alkyl;
$R^5$ is OH or $NH_2$, or O—C(=O)—$R^1$ or NH—C(=O)—$R^1$; and
Y is —$CH_2$—, —O—, or —S—;
or a pharmaceutically acceptable salt thereof, to the mammal.

18. The method of claim 16 for treating acetaminophen toxicity.

19. The method of claim 14 for treating Alzheimer's Disease, Parkinson's disease, amyotrophic lateral sclerosis (ALS), diabetes or stroke.

20. The method of claim 16 for treating Alzheimer's Disease, Parkinson's disease, amyotrophic lateral sclerosis (ALS), diabetes or stroke.

21. The compound of claim 1, wherein $R^2$ is OH, —O—C(=O)—$R^{1a}$, —NH—C(=O)—$R^{1a}$ or —NH—C(=O)O—$R^{1a}$.

22. The compound of claim 1, wherein $R^2$ is —NH—C(=O)—$R^{1a}$ or —NH—C(=O)O—$R^{1a}$.

23. The compound of claim 1, wherein each $R^1$ is independently $(C_1$-$C_6)$alkyl, $(C_3$-$C_8)$ cycloalkyl, aryl$(C_1$-$C_6)$alkyl, or heteroaryl$(C_1$-$C_6)$alkyl.

* * * * *